(12) United States Patent
Navascuez Lominchar et al.

(10) Patent No.: US 12,427,109 B2
(45) Date of Patent: Sep. 30, 2025

(54) NATURAL ORIGIN STABILIZER FOR OIL IN WATER EMULSIONS

(71) Applicant: FUNDACIÓN CIDETEC, Donostia-San Sebastián (ES)

(72) Inventors: Marcos Navascuez Lominchar, Donostia-San Sebastián (ES); Iraida Loinaz Bordonabe, Donostia-San Sebastián (ES); Damien Dupin, Donostia-San Sebastián (ES); Jordi Llop Roig, San Sebastián (ES); Fernando López-Gallego, Donostia-San Sebastián (ES)

(73) Assignee: FUNDACIÓN CIDETEC, Donostia-San Sebastián (ES)

( * ) Notice: Subject to any disclaimer, the term of this patent is extended or adjusted under 35 U.S.C. 154(b) by 480 days.

(21) Appl. No.: 17/785,391

(22) PCT Filed: Dec. 17, 2020

(86) PCT No.: PCT/EP2020/086700
§ 371 (c)(1),
(2) Date: Jun. 14, 2022

(87) PCT Pub. No.: WO2021/122942
PCT Pub. Date: Jun. 24, 2021

(65) Prior Publication Data
US 2023/0102859 A1    Mar. 30, 2023

(30) Foreign Application Priority Data
Dec. 18, 2019   (EP) .................................... 19383134

(51) Int. Cl.
| | |
|---|---|
| *A61K 8/06* | (2006.01) |
| *A61K 8/73* | (2006.01) |
| *A61K 9/107* | (2006.01) |
| *A61K 9/51* | (2006.01) |
| *A61K 49/18* | (2006.01) |
| *A61Q 5/00* | (2006.01) |
| *A61Q 19/00* | (2006.01) |
| *C08B 37/02* | (2006.01) |
| *C08B 37/08* | (2006.01) |

(52) U.S. Cl.
CPC .............. *A61K 9/107* (2013.01); *A61K 8/062* (2013.01); *A61K 8/732* (2013.01); *A61K 8/735* (2013.01); *A61K 8/736* (2013.01); *A61K 9/5161* (2013.01); *A61K 49/1806* (2013.01); *A61Q 5/00* (2013.01); *A61Q 19/00* (2013.01); *C08B 37/0021* (2013.01); *C08B 37/003* (2013.01); *C08B 37/0072* (2013.01); *A61K 2800/52* (2013.01)

(58) Field of Classification Search
CPC ........ A61K 9/107; A61K 8/062; A61K 8/732; A61K 8/735; A61K 8/736; A61K 9/5161; A61K 49/1806; A61K 2800/52; A61K 9/1075; A61K 9/5138; A61K 47/36; A61K 2800/54; A61Q 5/00; A61Q 19/00; C08B 37/0021; C08B 37/003; C08B 37/0072; C08L 5/02; C08L 5/08
See application file for complete search history.

(56) References Cited

FOREIGN PATENT DOCUMENTS

| | | | |
|---|---|---|---|
| EP | 3015482 A1 | 5/2016 | |
| WO | WO-2008109935 A1 * | 9/2008 | ........... A61K 8/0208 |

OTHER PUBLICATIONS

Busatto. Oil-in-microgel strategy for enzymatic-triggered release of hydrophobic drugs. Journal of Colloid and Interface Science. Jan. 10, 2017. (Year: 2017).*
Bencherif. Influence of the degree of methacrylation on hyaluronic acid hydrogels properties. Biomaterials. 2008 (Year: 2008).*
International Search Report and Written Opinion mailed Mar. 24, 2021 for International Application No. PCT/EP2020/086700, 17 pages.
Drelich et al., "Measurement of interfacial tension in fluid-fluid systems", Encyclopedia of Surface and Colloid Science 2002; pp. 3152-3166.
Macy, "Surface Tension by the Ring Method/ Applicability of the DU NUOY Apparatus", Journal of Chemical Education; Dec. 1935; vol. 12(12), pp. 573-576.
Moller et al., "Dextran and hyaluronan methacrylate based hydrogels as matrices for soft tissue reconstruction", Biomolecular Engineering 2007; vol. 24, pp. 496-504.
Qin et al., "Enzymatic Synthesis of hyaluronic acid vinyl esters for two-photon microfabrication of biocompatible and biodegradable hydrogel constructs", Polymer Chemistry 2014, vol. 5, pp. 6523-6533.
Academic Press Dictionary of Science and Technology 1992, p. 531.
A Terminological Dictionary of the Pharmaceutical Sciences 2007, pp. 190-191.
Shen et al., "Bacterial imprinting at Pickering Emulsion Interfaces", Angewandte Chemie, International Edition ; Aug. 11, 2014 ; vol. 53(40), pp. 10687-10690; XP055637662.

* cited by examiner

*Primary Examiner* — Michael G. Hartley
*Assistant Examiner* — Samantha L Mejias
(74) *Attorney, Agent, or Firm* — Squire Patton Boggs (US) LLP

(57) ABSTRACT

The present invention relates to the use of a methacrylate or acrylate modified polysaccharide; or a single-chain polysaccharide methacrylate or acrylate-based nanoparticle, having a surface tension measured by Du Noüy Ring method equal to or lower than 63 mN/m, as oil-in-water emulsion stabilizer; and an oil-in-water emulsion stabilizer composition, and an oil-in-water emulsion containing them. It also relates to processes for their preparation, and their uses.

18 Claims, 4 Drawing Sheets

NATURAL ORIGIN STABILIZER FOR OIL IN WATER EMULSIONS

CROSS-REFERENCE

The present application is a national-phase filing under 35 U.S.C. § 371 of International Application No. PCT/EP2020/086700 (filed Dec. 17, 2020), which claims the benefit of European Patent Application 19383134.4 (filed Dec. 18, 2019), both of which applications are incorporated herein by reference in their entirety.

The present invention relates to the field of oil-in-water emulsion stabilizer. In particular to the use of amphiphilic methacrylate or acrylate modified polysaccharide; or a single-chain polysaccharide methacrylate or acrylate-based nanoparticle as oil-in-water emulsion stabilizer having an esterase enzyme response. The present invention also relates to oil-in-water emulsion stabilizer composition, and an oil-in-water emulsion containing them, as well as processes for their preparation and their uses in therapy, diagnosis and cosmetics.

BACKGROUND ART

Polysaccharides are the most abundant macromolecules in the biosphere. They have many reactive groups, a wide range of molecular weight, varying chemical composition, which contribute to their diversity in structure and in property.

It has been disclosed in the state of the art that the modification of the backbone of the polysaccharides allows the hydrophilic nature of the polysaccharides to be modified. The amphiphilic nature imparted upon polysaccharides after modification gives them a wide and interesting application spectrum, for instance as rheology modifiers, emulsion stabilizers and/or surface modifiers. Recently, the hydrophobic modification of polysaccharides has received increasing attention because they can form self-assembled nanoparticles for biomedical uses. In the aqueous phase, the hydrophobic cores of polymeric nanoparticles are surrounded by hydrophilic outer shells. Thus, the inner core can serve as a container for hydrophobic drugs. However, the degree and kinetic degradation of these systems is crucial for the appropriate delivery of the drugs. Therefore, this has been widely studied for their biomedical application.

Thus, it is disclosed that the modification of the amphiphilic nature of dextran (polysaccharide) after the introduction of ether or phenoxy moieties in the backbone of the polysaccharide allows their use as emulsion emulsifier. However, as these modified polysaccharides with ether or phenoxy groups do not have enzyme responsiveness other than dextranase, which is not heavily present in the body, thus they are not useful as drug delivery vehicles.

Furthermore, polylactic modified dextran have been also disclosed in the state of the art as emulsion emulsifier having dextranase activity response. Dextranase hydrolyses the α-1,6-glycosidic linkage in dextran polymers, cleaving the linkages within the dextran molecule and releases shorter isomalto-saccharides. Unfortunately, dextranase are enzymes that are not present in human or animal body becoming these PLA modified polysaccharides inappropriate as drug delivery systems.

Therefore, from what is known in the art, it is derived that there is still the need of providing an efficient polysaccharide-based emulsion stabilizer useful in biomedical applications.

SUMMARY OF INVENTION

Inventors have found modified polysaccharides and nanoparticles containing them useful as oil-in water emulsion stabilizer and also as materials for a new encapsulation technology of active molecules. In particular, the inventors have surprisingly found that polysaccharides modified by the introduction of methacrylate or acrylate groups which have a surface tension equal to or lower than 63 mN/m have the appropriate amphiphilic nature for being use as oil-in water emulsion stabilizers with esterase enzyme response.

As it is shown in the experimental section, only the polysaccharides or nanoparticles of the present invention which have the claimed surface tension have interfacial activity and also esterase enzyme responsive. Nevertheless, the comparative methacrylate modified dextran polysaccharide having a surface tension higher than the claimed range (about 66 mN/m) does not show any interfacial activity as phase separation stabilizer.

Without being bound to any theory, it seems that the modification of natural polysaccharides with hydrophobic but reactive functional groups confer interfacial activity to produce stable oil-in-water emulsions. In fact, the presence of the methacrylate or acrylate modified polysaccharides or nanoparticles containing them having the reactive groups at the surface of the emulsion droplet allows an easy functionalization of polysaccharide to add active molecules or other biorelevant functionality. In particular, a lipophilic drug is dissolved into the oil phase of the oil-in-water emulsion having the methacrylate or acrylate modified polysaccharides or nanoparticles containing them in the interface's surface, ensuring that the totality of the encapsulated active lipophilic compound remains protected and any undesired leakage is avoided.

Furthermore, the formation of an ester bond between the carboxy group of the methacrylate or acrylate moieties and the hydroxyl group of the polysaccharide allows destabilizing the emulsion in the presence of esterase enzymes. In fact, the inventors has surprisingly found that only the presence of the relatively short methacrylate or acrylate group was sufficient to allow destabilizing the emulsion in the presence of esterase enzymes. Thus, the hydrolysis of the ester group allows releasing their cargo (active lipophilic compounds) in the target site. Therefore, the methacrylate or acrylate modified polysaccharides or nanoparticles containing them of the present invention offer an esterase enzyme-responsive emulsion stabilizer with biological applications. For example, the polysaccharides and nanoparticles of the present invention could be used for the treatment of diseases that involve an overexpression of esterase enzyme such as most of the inflammation diseases or disorders.

Besides, the destabilization of the emulsion containing the polysaccharide or nanoparticle of the present invention by the hydrolysis of the ester bond also allows recovering the entire polysaccharide, maintaining their biological activity. Thus, the emulsions of the invention have a double biological action, a first biological activity linked to the active compound encapsulated inside the emulsion and a second biological activity related to the biological activity of the natural polysaccharide. It is advantageous, because the polysaccharide thus release has a low or null degree of substitution and then, it is well-tolerated and biocompatible with the human or animal body. For example, in the case of oil-in-water emulsions comprising the methacrylate or acrylate modified hyaluronic acid or the nanoparticles containing them, in addition to the activity belonging to the active compounds encapsulated inside, an anti-inflammatory activity belonged to the released hyaluronic acid from the emulsion is observed.

Finally, the stability of the oil-in-water emulsions containing the polysaccharides or the nanoparticles of the present invention and their destabilization kinetics (which conditioned the release kinetics of the active compounds contained inside) in the presence of esterase enzyme can be adjusted by cross-linking the polysaccharides or the nanoparticles present at the oil/water interface of the emulsion droplet by the use of an interfacial crosslinker. In this way, it was demonstrated that the emulsions of the present invention were stable for months (up to 1 year according to accelerated stability test) in any physiologically relevant medium. Nevertheless, in the presence of esterase enzymes, the emulsion was also destabilized, and the release kinetics of the encapsulated compound could be prolonged significantly thanks to the presence of the interfacial cross-linker compared to emulsion without any cross-linker. Therefore, the cross-linking of the polysaccharide or the nanoparticles located at the oil/water interface allows having a more stable emulsion using nearly any oily phase without occurring its destabilization (increased versatility).

Thus, the first aspect of the invention relates to an use of a methacrylate or acrylate modified polysaccharide; or alternatively, a single-chain polysaccharide methacrylate or acrylate-based nanoparticle, having a surface tension measured by Du Noüy Ring method equal to or lower than 63 mN/m, as oil-in-water emulsion stabilizer.

The second aspect of the invention relates to an oil-in-water emulsion stabilizer according to an oil-in-water emulsion stabilizer composition comprising: a methacrylate or acrylate modified polysaccharide as defined in the first aspect of the invention; or alternatively, a single-chain polysaccharide methacrylate or acrylate-based nanoparticle as defined in the first aspect of the invention; and one or more appropriate excipients or carriers.

The third aspect of the invention relates to an oil-in-water emulsion to an oil-in-water emulsion comprising:
(a) the external water phase (W) comprising:
(a1) a solvent selected from the group consisting water, glycol and a mixture thereof; and
(a2) optionally, one or more hydrophilic compounds selected from the group consisting of: (a2') hydrophilic active agent and (a2") hydrophilic excipients or carriers;
(b) the internal oily phase (O) comprising one or more lipophilic compounds selected from the group consisting of:
(b1) lipophilic active agents, and
(b2) lipophilic excipients or carriers;
and
(c) an interfacial layer (IL) between the external water phase (W) and the internal oily phase (O) comprising:
(c1) one or more emulsion stabilizer selected from the group consisting of:
(c1') methacrylate or acrylate modified polysaccharides as defined in the first aspect of the invention;
(c1") single-chain polysaccharide methacrylate or acrylate-based nanoparticles as defined in the first aspect of the invention;
(c1''') interfacial crosslinked methacrylate or acrylate modified polysaccharides obtainable by reacting the methacrylate or acrylate modified polysaccharides as defined in the first aspect of the invention with an interfacial crosslinking agent, wherein the interfacial crosslinked methacrylate or acrylate modified polysaccharides has an interfacial crosslinking degree from 25 to 100% of the methacrylate or acrylate groups of the polysaccharide; or alternatively,
(c1'''') interfacial crosslinked single-chain polysaccharide methacrylate or acrylate based nanoparticles obtainable by reacting the single-chain polysaccharide methacrylate or acrylate-based nanoparticles as defined in the first aspect of the invention with an interfacial crosslinking agent, wherein the interfacial crosslinked single-chain polysaccharide methacrylate or acrylate based nanoparticles has an interfacial crosslinking degree from 25 to 100% of the methacrylate or acrylate groups of the nanoparticles; and
c2) optionally, one or more hydrophilic active agents.

The fourth aspect of the invention relates to the use of the oil-in-water emulsion according to the third aspect of the invention, as a carrier.

The fifth aspect of the invention relates to the oil-in-water emulsion according to the third aspect of the invention, for use in therapy, diagnosis and cosmetics.

It is also a part of the invention processes for the preparation of the oil-in-water emulsion stabilizer composition of the second aspect of the invention and the oil-in-water emulsion of the fourth aspect of the invention.

DETAILED DESCRIPTION OF THE INVENTION

Figure 1:
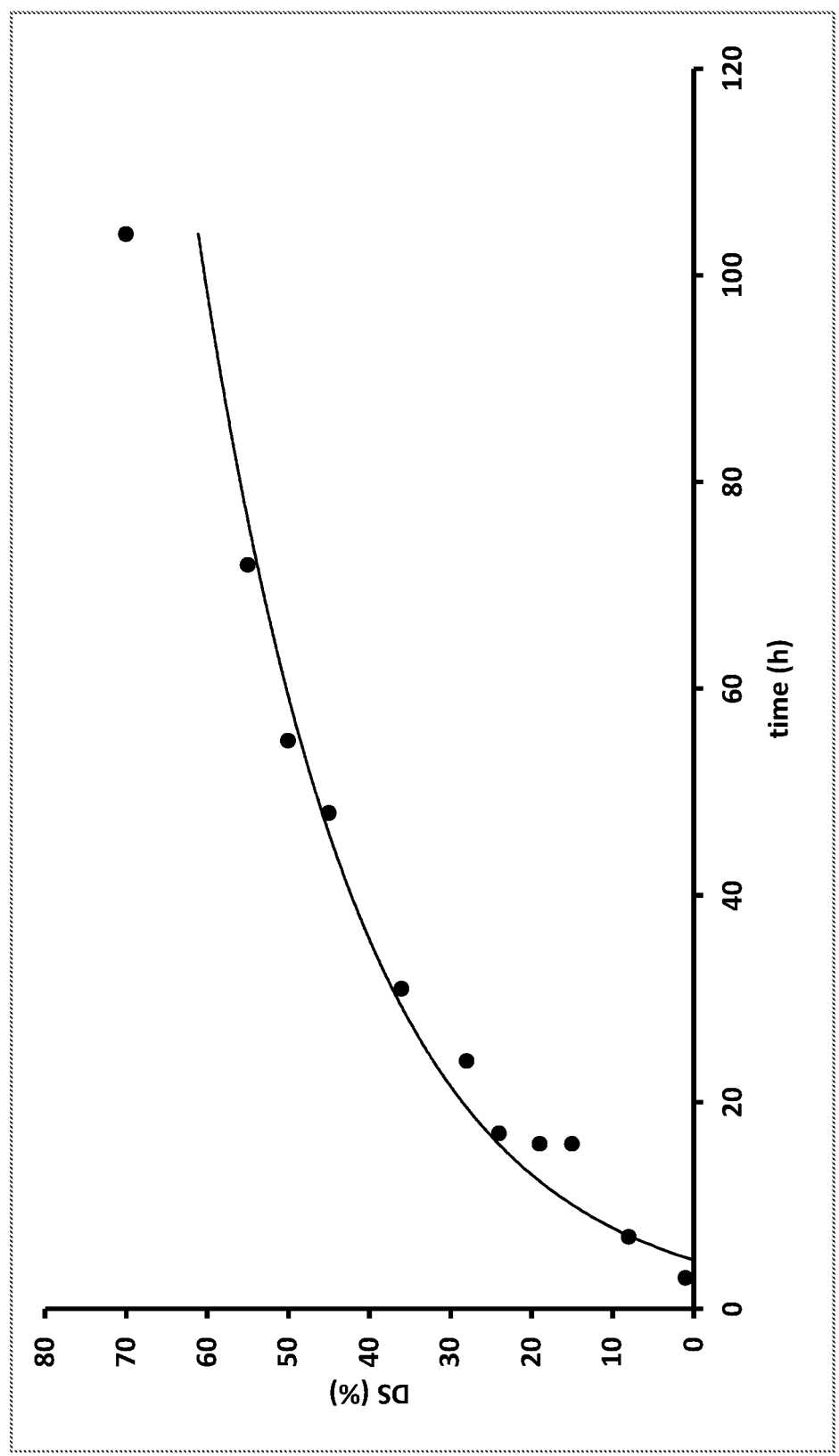
FIG. 1 shows the kinetics of the methacrylate modified dextran polysaccharide of the present invention. Comparison of the methacrylic (MA) substitution degree (DS) depending on the reaction time.
Figure 2:
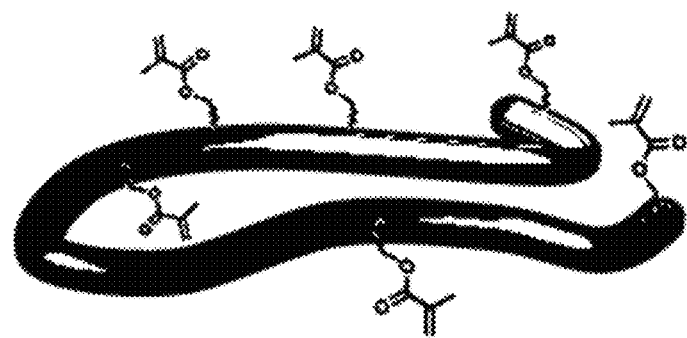
FIG. 2 shows a schematic representation of the physicochemical structure of a methacrylate modified polysaccharide of the present invention.
Figure 3:
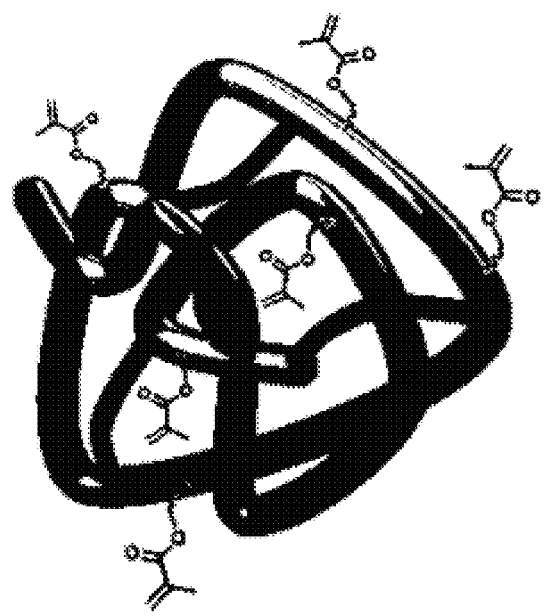
FIG. 3 shows a schematic representation of the physicochemical structure of single-chain polysaccharide methacrylate-based nanoparticle of the present invention.
Figure 4:
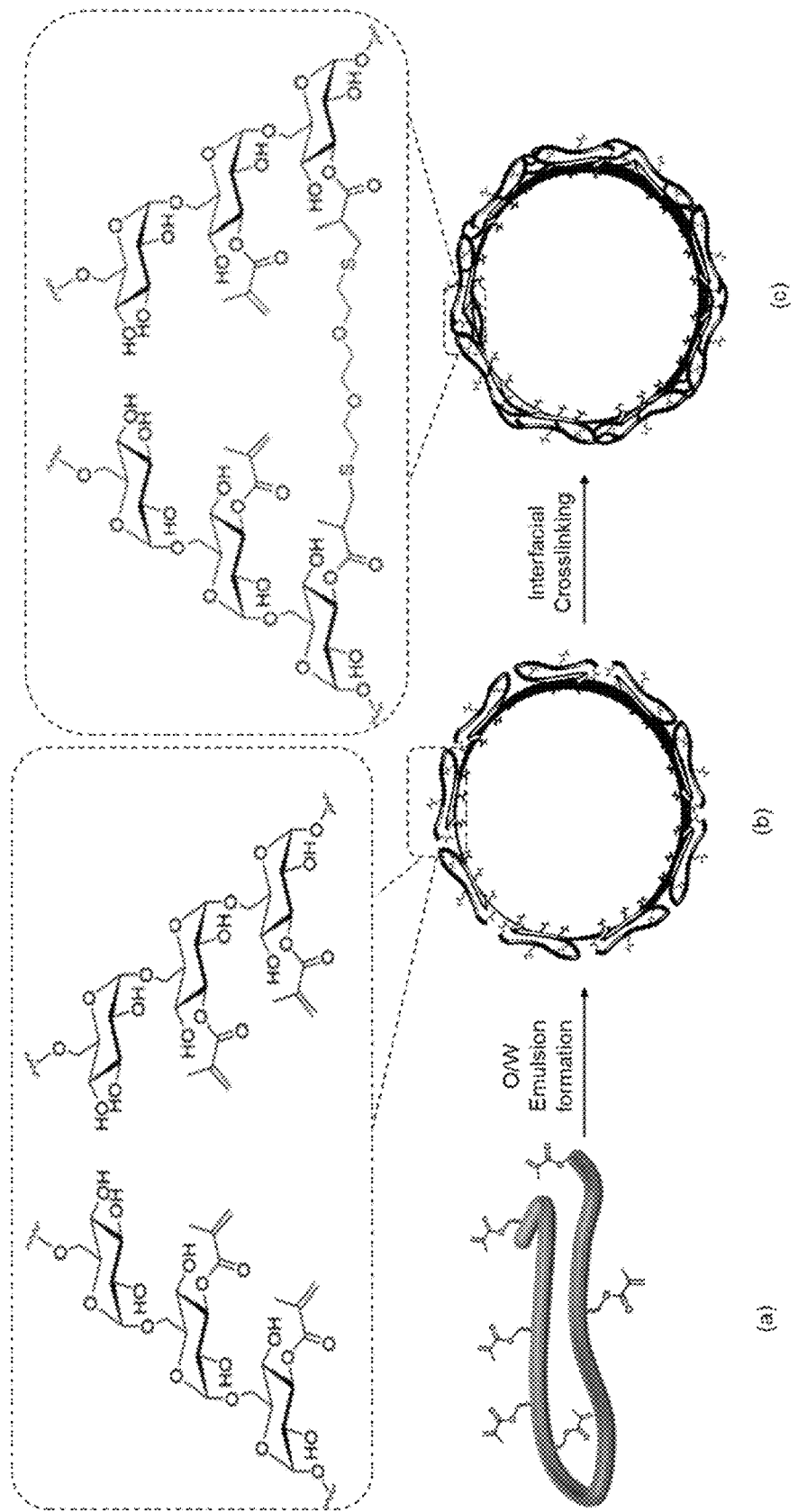
FIG. 4 shows a schematic representation of a process for the preparation of an oil-in-water emulsion of the present invention comprising a methacrylate modified dextran of the present invention in the interfacial layer (IL) of the emulsion (b) from a methacrylate modified dextran of the present invention (a); and the subsequent interfacial crosslinking step with DODT as interfacial crosslinker to obtain an oil-in-water emulsion of the present invention comprising an inter-crosslinked methacrylate modified dextran in the interfacial layer (IL) of the emulsion (c).
Figure 5:
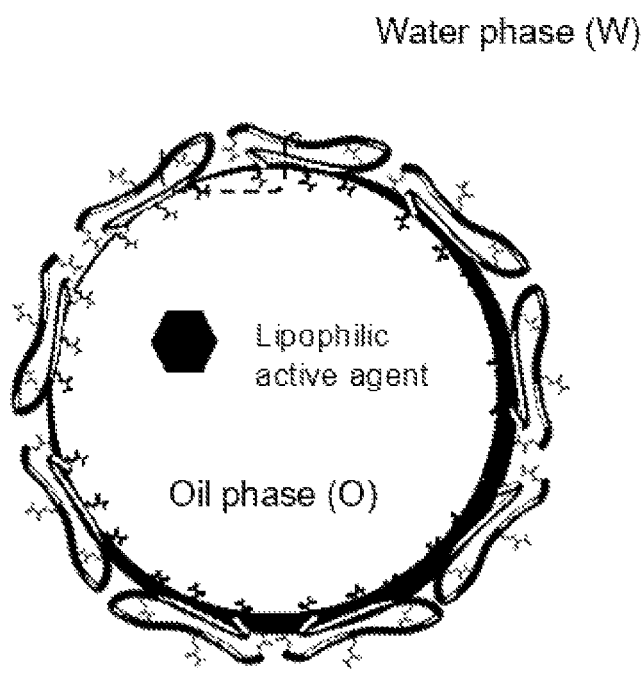
FIG. 5 shows a schematic representation of an oil-in-water emulsion of the present invention comprising a methacrylate modified polysaccharide in the interfacial layer (IL) and a lipophilic active encapsulated in the oil phase (O).
Figure 6:
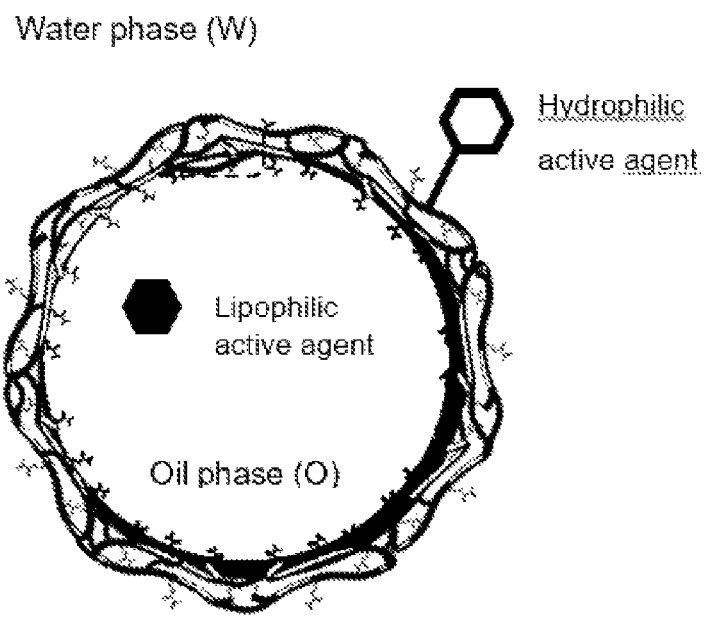
FIG. 6 shows a schematic representation of an oil-in-water emulsion of the present invention comprising a interfacial crosslinked methacrylate modified polysaccharide in the interfacial layer (IL), a lipophilic active agent encapsulated in the oil phase (O) and a hydrophilic active agent linked to the external surface of the interfacial crosslinked methacrylate modified polysaccharide.

All terms as used herein in this application, unless otherwise stated, shall be understood in their ordinary meaning as known in the art. Other more specific definitions terms as used in the present application are as set forth below and are intended to apply uniformly throughout the specification and claims unless an otherwise expressly set out definition provides a broader definition.

For the purposes of the present invention, any ranges given include both the lower and the upper endpoints of the range. Ranges given, such as temperatures, times, weights, and the like, should be considered approximate, unless specifically stated.

The terms "percentage (%) by weight", "weight/weight %" and "w/w %" have the same meaning and are used interchangeably. They refer to the percentage of one ingredient in relation to the total weight of a composition or mixture. As it is mentioned above, the first aspect of the invention relates to the use of a methacrylate or acrylate modified polysaccharide; or alternatively, a single-chain polysaccharide methacrylate or acrylate-based nanoparticle, having a surface tension measured by Du Noüy Ring method equal to or lower than 63 mN/m, as oil-in-water emulsion stabilizer.

The term "polysaccharide" refers to a polymeric carbohydrate having a plurality of repeating units, at least 4, comprised of simple sugars. For the purpose of the invention, the term "simple sugars" refers to monosaccharides or disaccharides. In an embodiment, the polysaccharide is selected from the group consisting of dextran, hyaluronic acid, alginate, gellan gum, cellulose and derivative thereof, glycogen, and chitosan. In an embodiment, the polysaccharide is dextran. In an embodiment, the polysaccharide is hyaluronic acid. In an embodiment, the polysaccharide is alginate. In an embodiment, the polysaccharide is gellan gum. In an embodiment, the polysaccharide is cellulose and derivative thereof; particularly hydroxyl ethyl cellulose and methyl cellulose. In an embodiment, the polysaccharide is glycogen. In an embodiment, the polysaccharide is chitosan. For the purpose of the present invention, all the aspects and embodiments (taken them alone or in combination with other embodiments disclosed above or below) disclosed in the invention with any one of the polysaccharides taken separately forms also part of the invention.

The terms "single-stranded nanoparticles", "single-chain nanoparticles" and the abbreviature "SCNPs" have the same meaning and are used interchangeable. They refer to three-dimensional "crosslinked" nanoparticle which comprises the modified polysaccharides of the present invention. The SCNPs are usually prepared by reacting a crosslinkable group of the modified polysaccharide with a crosslinking agent.

As used herein, the term "nanoparticle" refers to particles having nanoscale dimensions, i.e., having a diameter from about 1 to about 1000 nanometres. The particle size of the nanoparticles of the invention can be measured by any method disclosed in the state of the art. In particular, the method used in the present invention for measuring the particle size is Dynamic light scattering (DLS) to measure particles in solution and Atomic force microscopy (AFM) or transmission electron microscopy (TEM) to measure particles in dry state. The term "crosslinked" refers to nanoparticle that have three-dimensional crosslink network wherein the network is formed by a single-chain of the starting methacrylate or acrylate polysaccharide that has been collapsed by one or more intramolecular crosslinking agents. The term "crosslinking" refers in the polymer science field to the use of cross-links to promote a difference in the physical properties of the polymers. The term "crosslink" refers to bonds that link one methacrylate or acrylate reactive group of the polysaccharide with a crosslinkable group of the crosslinking agent by hydrolysable covalent bonding. For example, the bond that link one methacrylate or acrylate reactive groups of the polysaccharide with a crosslinkable group of the crosslinking agent is a hydrolysable covalent bond. The term "crosslinker" or "crosslinking agent" which is herein used interchangeably refers to compound having the ability to cross-link polymer chain(s). The term "homo-bifunctional crosslinking agent" refers to those crosslinking agents that contain two identical reactive sites (i.e. two identical crosslinkable groups), which can react with the reactive groups of the methacrylate or acrylate groups of polysaccharide.

The terms "polysaccharide methacrylate or acrylate based" and "methacrylate or acrylate modified polysaccharide" have the same meaning and are used interchangeably. They refer to a polysaccharide formed by a polysaccharide that includes esters of methacrylate or acrylate in the structure.

The terms "single-chain polysaccharide methacrylate or acrylate-based nanoparticle" or "single-chain methacrylate or acrylate modified polysaccharide-based nanoparticle" have the same meaning and are used interchangeably. They refer to a nanoparticles formed by a single-chain formed by a polysaccharide that include esters of methacrylate or acrylate in the structure.

The term "ester" refers to the chemical group —CO—O—. For the purpose of the invention, the ester group is formed by the covalent bond of the carbon atom of the group —CO— of the methacrylate or acrylate moiety to the oxygen atom of the OH— moiety of the polysaccharide.

The amount of methacrylate or acrylate groups present in the polysaccharide chain can be measured by Nuclear Magnetic Resonance (NMR) spectroscopy. Particularly by proton nuclear magnetic resonance spectroscopy.

In an embodiment, the methacrylate or acrylate modified polysaccharide comprises a degree of substitution of methacrylate or acrylate groups from 1 to 100% of modified repeating units of the polysaccharide. In an embodiment, the degree of substitution of the polysaccharide with the methacrylate or acrylate groups is from 5 to 100% of modified repeating units of the polysaccharide. In an embodiment, the degree of substitution of the polysaccharide with the methacrylate or acrylate groups is from 10 to 100% of modified repeating units of the polysaccharide. In an embodiment, the degree of substitution of the polysaccharide with the methacrylate or acrylate groups is from 10 to 70% of modified repeating units of the polysaccharide.

In an embodiment, the polysaccharide is dextran and the degree of substitution of the polysaccharide with the methacrylate or acrylate groups is from 1 to 100% of modified repeating unit of the polysaccharide. In an embodiment, the polysaccharide is dextran and the degree of substitution of the polysaccharide with the methacrylate or acrylate groups is from 5 to 100% of modified repeating unit of the polysaccharide. In an embodiment, the polysaccharide is dextran and the degree of substitution of the polysaccharide with the methacrylate or acrylate groups is from 10 to 100% of modified repeating unit of the polysaccharide. In an embodiment, the polysaccharide is dextran and the degree of substitution of the polysaccharide with the methacrylate or acrylate groups is from 10 to 70% of modified repeating unit of the polysaccharide.

In an embodiment, the single-chain polysaccharide methacrylate or acrylate-based nanoparticles comprises a degree of substitution of methacrylate or acrylate groups from 1% to 98% of modified repeating units of the nanoparticles. In an embodiment, the degree of substitution of the single-chain polysaccharide methacrylate or acrylate-based nanoparticles with the methacrylate or acrylate groups is from 5 to 98% of modified repeating units of the nanoparticles. In an embodiment, the degree of substitution of the single-chain polysaccharide methacrylate or acrylate-based nanoparticles with the methacrylate or acrylate groups is from 10 to 98% of modified repeating units of the nanoparticles. In an embodiment, the degree of substitution of the single-chain polysaccharide methacrylate or acrylate-based nanoparticles with the methacrylate or acrylate groups is from 10 to 70% of modified repeating units of the nanoparticles.

In an embodiment, the polysaccharide is dextran and the degree of substitution of the single-chain dextran methacrylate or acrylate-based nanoparticles with the methacrylate or acrylate groups is from 1 to 98% of modified repeating unit of the nanoparticles. In an embodiment, the polysaccharide is dextran and the degree of substitution of the single-chain dextran methacrylate or acrylate-based nanoparticles with the methacrylate or acrylate groups is from 5 to 98% of modified repeating unit of the nanoparticles. In an embodiment, the polysaccharide is dextran and the degree of substitution of the single-chain dextran methacrylate or acrylate-based nanoparticles with the methacrylate or acrylate groups is from 10 to 98% of modified repeating unit of the nanoparticles. In an embodiment, the polysaccharide is dextran and the degree of substitution of the single-chain dextran methacrylate or acrylate-based nanoparticles with the methacrylate or acrylate groups is from 1 to 70% of modified repeating unit of the nanoparticles.

The terms "degree of substitution", "substitution degree" and the abbreviature "DS" have the same meaning and are used interchangeable. In the case of the methacrylate or acrylate polysaccharide, the degree of substitution is expressed as the percent of modified repeating unit of the polysaccharide assuming that only one hydroxyl group per repeating unit is modified; and it is measured by Nuclear Magnetic Resonance (NMR) spectroscopy; particularly by proton nuclear magnetic resonance (H-NMR; cf. the characterization method of the experimental section of the application). Thus, for example, a methacrylate or acrylate modified dextran having a degree of substitution of 80% of repeating units implies that the 80% of the repeating units of the dextran (i.e. 80% of the glucose units of the dextran) have been modified by a methacrylate or acrylate group, assuming that only one hydroxyl group per repeating unit is modified. In the case of the single-chain polysaccharide methacrylate or acrylate-based nanoparticles, the degree of substitution is expressed as the percent of modified repeating unit of the nanoparticles assuming that only one hydroxyl group per repeating unit is modified; and it is measured by Nuclear Magnetic Resonance (NMR) spectroscopy; particularly by proton nuclear magnetic resonance (H-NMR; cf. the characterization method of the experimental section of the application). Thus, for example, single-chain dextran methacrylate or acrylate-based nanoparticles having a degree of substitution of 80% of repeating units implies that the 80% of the repeating units of the dextran nanoparticles (i.e. 80% of the glucose units of the dextran nanoparticles) have been modified by a methacrylate or acrylate group, assuming that only one hydroxyl group per repeating unit is modified.

In particular, the methacrylate esters are usually prepared by transesterification by treating the polysaccharide with glycidyl methacrylate (GMA) and the acrylate esters are usually prepared from a slightly modified procedure which implies treating the polysaccharide with vinyl acrylate (VA), or glycidyl acrylate, acryloyl chloride.

For the purpose of the invention, the term "emulsion stabilizer" refers to compounds that stabilize, emulsify, prevent phase separation and/or change the viscosity of the compositions in such a way that reduce the interfacial tension by reducing the energy necessary to maintain the interfaces between the droplets in the external phase surrounding them. Particularly, the polysaccharide and nanoparticles of the invention can align themselves at hydrophilic/hydrophobic or polar/non-polar interface reducing the interfacial tension.

As it is mentioned above, the methacrylate or acrylate modified polysaccharide; or alternatively, the single-chain polysaccharide methacrylate or acrylate-based nanoparticle of the present invention has the appropriate amphiphilic properties for being used as oil-in-water emulsion stabilizer having esterase enzyme response. Particularly, they have a surface tension measured by Du Noüy Ring method equal to or lower than 63 mN/m. The measurement of the surface tension was performed by the Du Noüy Ring method is commonly known by a skilled person in the art. This method brings a platinum ring in contact with the surface or interface. First the ring is fully submerged and then slowly lifted to form a meniscus-like. During the process, the force of the meniscus pulling on the ring is measured. Prior to the meniscus tearing, the meniscus will exert a maximum force. This maximum force is used in determining the surface tension (cf. Rudolph Macy, "Surface tension by the ring method. Applicability of the du Noüy apparatus". *J. Chem. Educ.* 1935, vol. 12(12), pp. 573 and the characterization method of the experimental section of the application).

In an embodiment, the surface tension measured by Du Noüy Ring method is equal to or lower than 60 mN/m. In an embodiment, the polysaccharide is selected from the group consisting of dextran, hyaluronic acid, alginate, gellan gum, cellulose and derivative thereof, glycogen, and chitosan and the surface tension is equal to or lower than 60 mN/m measured by Du Noüy Ring method. In an embodiment, the polysaccharide is selected from the group consisting of dextran, hyaluronic acid and chitosan and the surface tension is equal to or lower than 60 mN/m measured by Du Noüy Ring method. In an embodiment, the polysaccharide is dextran and the surface tension is equal to or lower than 60 mN/m measured by Du Noüy Ring method.

In an embodiment, the use of the invention relates to the use of a methacrylate or acrylate modified polysaccharide having a surface tension measured by Du Noüy Ring method equal to or lower than 63 mN/m, particularly a surface tension measured by Du Noüy Ring method equal to or lower than 60 mN/m, as oil-in-water emulsion stabilizer. In an embodiment, the use of the invention relates to the use of a methacrylate modified polysaccharide having a surface tension measured by Du Noüy Ring method equal to or lower than 63 mN/m, particularly a surface tension measured by Du Noüy Ring method equal to or lower than 60 mN/m, as oil-in-water emulsion stabilizer. In an embodiment, the use of the invention relates to the use of an acrylate modified polysaccharide having a surface tension measured by Du Noüy Ring method equal to or lower than 63 mN/m, particularly a surface tension measured by Du Noüy Ring method equal to or lower than 60 mN/m, as oil-in-water emulsion stabilizer.

The term "dextran" or "dextran chain" have the same meaning and are used interchangeably. They refer to a complex branched glucan (polysaccharide derived from the condensation of glucose). IUPAC defines dextran as "branched poly-α-d-glucosides of microbial origin having glycosidic bonds predominantly C-1→C-6". Dextran chains are of varying molecular weights (from 3 to 2000 kilodaltons). The polymer main chain of dextran consists of α-1,6 glycosidic linkages between glucose monomers, with branches from α-1,3 linkages.

The terms "dextran methacrylate or acrylate based" and "methacrylate or acrylate modified dextran" have the same meaning and are used interchangeably. They refer to a polysaccharide or nanoparticle formed by a dextran that includes esters of methacrylate or acrylate in the structure.

In particular, the methacrylate esters are usually prepared by transesterification by treating the dextran with glycidyl methacrylate (GMA) under such reaction conditions to form an ester bond from a hydroxyl group of the glucose monomer and the carbonyl group of the GMA (cf. van Dijk-Wolthuis et al., Biomolecular Engineering, 2007, vol. 24, pp. 496-504) as it is summarized in the scheme below:

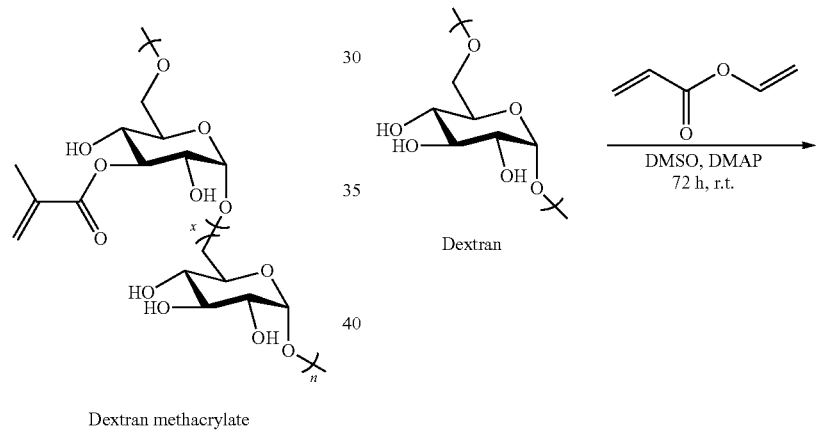

The acrylate esters are usually prepared from a slightly modified procedure which implies treating the dextran with glycidyl acrylate (GA) under such reaction conditions to form an ester bond from a hydroxyl group of the glucose monomer and the carbonyl group of the GA (cf. van Dijk-Wolthuis et al., Biomolecular Engineering, 2007, vol. 24, pp. 496-504) as it is summarized in the scheme below:

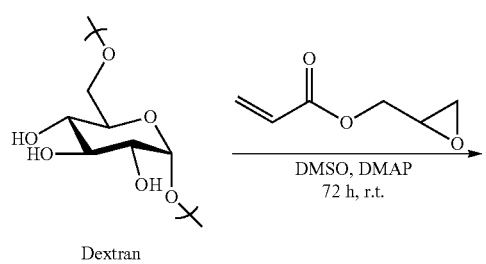

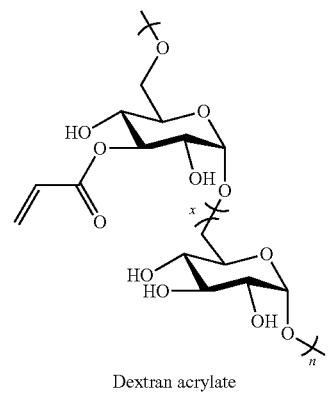

Or alternatively, the acrylate esters are usually prepared from a slightly modified procedure which implies treating the dextran with vinyl acrylate (VA) under such reaction conditions to form an ester bond from a hydroxyl group of the glucose monomer and the carbonyl group of the VA (cf. L. Ferreira et al., Biomaterials, 2002, vol. 23, pp. 3957-3967) as it is summarized in the scheme below:

In an embodiment, the methacrylate or acrylate modified polysaccharide is selected from the group consisting of a methacrylate modified dextran having a degree of substitution of the methacrylate groups from 1% to 100% of modified repeating units of the dextran and comprising repeating units of formula (I)

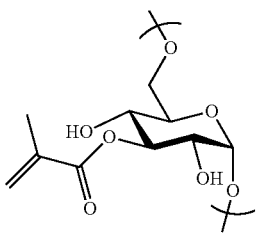

(I)

and an acrylate modified dextran having a degree of substitution of the acrylate groups from 1% to 100% of modified repeating units of the dextran and comprising repeating units of formula (II);

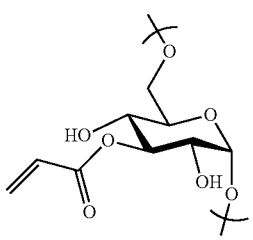

(II)

In an embodiment, the methacrylate or acrylate modified polysaccharide is selected from the group consisting of a methacrylate modified dextran comprising repeating units of formula (I) and having a degree of substitution of the methacrylate groups from 1% to 100% of repeating units of the dextran; and an acrylate modified dextran comprising repeating units of formula (II) and having a degree of substitution of the acrylate groups from 1% to 100% of repeating units of the dextran; particularly methacrylate modified dextran comprising repeating units of formula (I). In an embodiment, the methacrylate or acrylate modified polysaccharide is selected from the group consisting of a methacrylate modified dextran comprising repeating units of formula (I) and having a degree of substitution of the methacrylate groups from 5% to 100% of repeating units of the dextran; and an acrylate modified dextran comprising repeating units of formula (II) and having a degree of substitution of the acrylate groups from 5% to 100% of repeating units of the dextran; particularly methacrylate modified dextran comprising repeating units of formula (I). In an embodiment, the methacrylate or acrylate modified polysaccharide is selected from the group consisting of a methacrylate modified dextran comprising repeating units of formula (I) and having a degree of substitution of the methacrylate groups from 10% to 100% of repeating units of the dextran; and an acrylate modified dextran comprising repeating units of formula (II) and having a degree of substitution of the acrylate groups from 10% to 100% of repeating units of the dextran; particularly methacrylate modified dextran comprising repeating units of formula (I). In an embodiment, the methacrylate or acrylate modified polysaccharide is selected from the group consisting of a methacrylate modified dextran comprising repeating units of formula (I) and having a degree of substitution of the methacrylate groups from 10% to 70% of repeating units of the dextran; and an acrylate modified dextran comprising repeating units of formula (II) and having a degree of substitution of the acrylate groups from 10% to 70% of repeating units of the dextran; particularly methacrylate modified dextran comprising repeating units of formula (I).

For the purpose of the present invention, the term "Hyaluronic acid", "hyaluronan" and the abbreviation "HA" have the same meaning and are used interchangeable. They refer to the natural, non-sulphated anionic form of glycosaminoglycan having the CAS number 9004-61-9, being composed of several repeated disaccharide units of N-acetyl-D-glucosamine and D-glucuronic. Its chemical structure corresponds to the following formula:

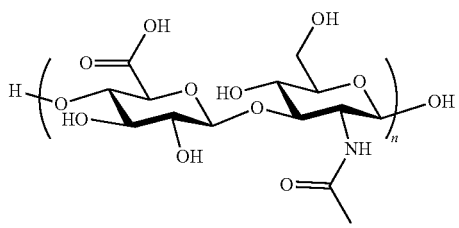

For the purpose of the invention, the term "hyaluronic" encompasses an appropriate salt of hyaluronic acid. There is no limitation on the type of hyaluronic acid salt that can be used, as long as they are pharmaceutically, cosmetically or diagnostically acceptable when used for therapeutic, cosmetic or diagnostic purposes respectively. Hyaluronic acid and a salt thereof may differ in some physical properties, but they are equivalent for the purposes of the present invention and their properties of hyaluronic acid are extensible to a pharmaceutically, cosmetically and diagnostically acceptable salt. The preparation of acceptable salts of hyaluronic acid can be carried out by methods known in the technique. Non-limiting examples of pharmaceutical, cosmetically or diagnostically acceptable salts of hyaluronic acid appropriate for the present invention include inorganic salts such as sodium hyaluronate, magnesium hyaluronate, potassium hyaluronate, zinc hyaluronate and cobalt hyaluronate, as well as organic salts such as tetrabutylammonium hyaluronate. In an embodiment, the pharmaceutically, cosmetically or diagnostically acceptable salt of hyaluronic acid is a salt of a selected alkaline metal of sodium salt (CAS No: 9067-32-7) or potassium salt (CAS No: 31799-91-4). In an embodiment, the hyaluronic acid or a salt thereof (for instance sodium hyaluronate) has a molecular weight of 50 kDa or more. In an embodiment, the hyaluronic acid or a salt thereof (for instance sodium hyaluronate) has a molecular weight from 50 kDa to 5000 kDa.

The terms "hyaluronic methacrylate or acrylate based" and "methacrylate or acrylate modified hyaluronic acid" have the same meaning and are used interchangeably. They refer to a polysaccharide or nanoparticle formed by a hyaluronic acid that includes esters of methacrylate or acrylate in the structure.

In an embodiment, the methacrylate or acrylate modified polysaccharide is selected from the group consisting of a methacrylate modified hyaluronic acid having a degree of substitution of the methacrylate groups from 1% to 100% of modified repeating units of the hyaluronic acid.

In an embodiment, the methacrylate or acrylate modified polysaccharide is selected from the group consisting of a methacrylate modified hyaluronic acid having a degree of substitution of the methacrylate groups from 1% to 100% of modified repeating units of the hyaluronic acid and comprising repeating units of formula (IV);

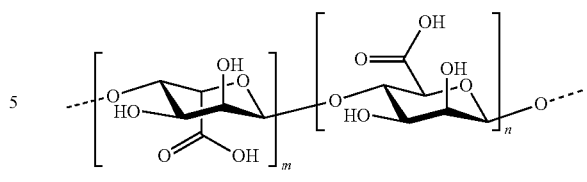

(IV)

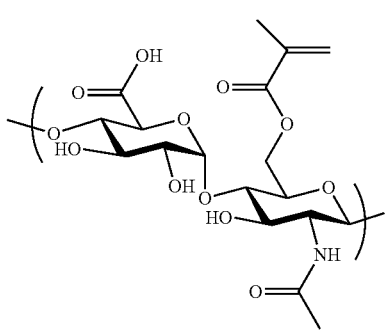

and an acrylate modified hyaluronic acid having a degree of substitution of the acrylate groups from 1% to 100% of modified repeating units of the hyaluronic acid and comprising repeating units of formula (V).

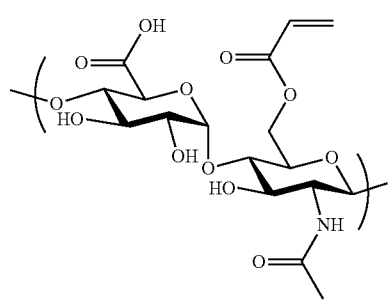

(V)

In a particular embodiment, the methacrylate or acrylate modified polysaccharide is an acrylate modified hyaluronic acid comprising repeating units of formula (V) and having a degree of substitution of the methacrylate groups from 1% to 100% of the modified repeating units of the hyaluronic acid; particularly acrylate modified hyaluronic acid comprising repeating units of formula (V).

For the purpose of the present invention, the term alginic acid is a linear copolymer with homopolymer blocks of (1-4)-linked β-D-mannuronate (M) and its C-5 epimer α-L-guluronate (G) residues, respectively, covalently linked together in different sequences or blocks having the CAS number 9005-32-7. Its chemical structure corresponds to the following formula:

For the purpose of the invention, the term "alginic acid" encompasses an appropriate salt of alginic acid. There is no limitation on the type of alginic acid salt that can be used, as long as they are pharmaceutically, cosmetically or diagnostically acceptable when used for therapeutic, cosmetic or diagnostic purposes respectively. The preparation of acceptable salts of alginic acid can be carried out by methods known in the technique. Non-limiting examples of pharmaceutical, cosmetically or diagnostically acceptable salts of alginic acid appropriate for the present invention include alkali metal salts of alginate such as sodium alginate and calcium alginate.

In an embodiment, the methacrylate or acrylate modified polysaccharide is selected from the group consisting of a methacrylate modified alginate having a degree of substitution of the methacrylate groups from 1% to 100% of modified repeating units of alginate; and an acrylate modified alginate having a degree of substitution of the acrylate groups from 1% to 100% of modified repeating units of alginate.

For the purpose of the present invention, the term "gellan gum" refers to a polysaccharide having the CAS number 71010-52-1 having a tetra saccharide repeating unit, which consists of two residues of D-glucose and one of each residues of L-rhamnose and D-glucuronic acid. The tetra saccharide repeat has the following structure: [D-Glc(β1→4)D-GlcA(β1→4)D-Glc(β1→4)L-Rha(α1→3)]n of formula:

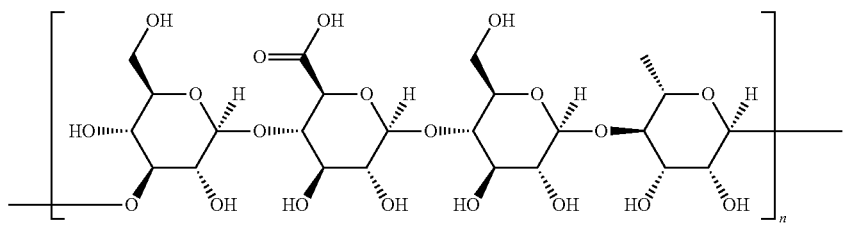

In an embodiment, the methacrylate or acrylate modified polysaccharide is selected from the group consisting of a methacrylate modified gellan gum having a degree of substitution of the methacrylate groups from 1% to 100% of modified repeating units of gellan gum; and an acrylate modified gellan gum having a degree of substitution of the acrylate groups from 1% to 100% of modified repeating units of gellan gum.

For the purpose of the present invention, the term "cellulose" refers to a polysaccharide formed by a linear chain of repeating units β(1→4) linked D-glucose units having the CAS number 9004-34-6. Its chemical structure corresponds to the following formula:

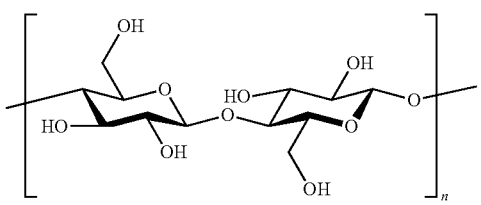

Furthermore, for the purpose of the present invention the term "cellulose derivatives" encompasses alkyl celluloses, hydroxyalkyl celluloses and carboxyalkyl celluloses. "Hydroxyalkyl cellulose" refers to an ether derivative of a cellulose compound having a hydroxyalkyl group. Examples of hydroxyalkyl cellulose include hydroxypropyl cellulose, hydroxyethyl cellulose, hydroxyethylmethyl cellulose or ethyl hydroxyethyl cellulose, hydroxypropyl methyl cellulose. "Alkyl cellulose" refers to an ether derivative of a cellulose compound having an alkyl group. Examples of alkyl cellulose include methyl cellulose, ethyl cellulose or methyl cellulose. "Carboxyalkyl cellulose" refers to an ether derivative of a cellulose compound having a carboxyl alkyl group and their salts. Examples of carboxyalkyl cellulose include carboxymethyl cellulose. In an embodiment, the polysaccharide is a cellulose selected from the group consisting of hydroxyethylcellulose and methyl cellulose. In an embodiment, the polysaccharide is hydroxyethylcellulose. In an embodiment, the polysaccharide is methylcellulose.

In an embodiment, the methacrylate or acrylate modified polysaccharide is a methacrylate modified cellulose selected from methacrylate modified hydroxyethylcellulose and methacrylate modified methylcellulose having a degree of substitution of the methacrylate groups from 1% to 100% of modified repeating units of hydroxyethylcellulose or methylcellulose; and an acrylate modified cellulose selected from acrylate modified hydroxyethylcellulose and acrylate modified methylcellulose having a degree of substitution of the acrylate groups from 1% to 100% of modified repeating units of hydroxyethylcellulose or methylcellulose.

For the purpose of the present invention, the term "glycogen" refers to a multibranched polysaccharide of glucose. Particularly, the glycogen is a branched biopolymer consisting of linear chains of glucose residues with an average chain length of approximately 8-12 glucose units. Glucose units are linked together linearly by α(1→4) glycosidic bonds from one glucose to the next. Branches are linked to the chains from which they are branching off by α(1→6) glycosidic bonds between the first glucose of the new branch and a glucose on the stem chain.

In an embodiment, the methacrylate or acrylate modified polysaccharide is selected from the group consisting of a methacrylate modified glycogen having a degree of substitution of the methacrylate groups from 1% to 100% of modified repeating units of glycogen; and an acrylate modified glycogen having a degree of substitution of the acrylate groups from 1% to 100% of modified repeating units of glycogen.

For the purpose of the present invention, the term "chitosan" refers to a linear polysaccharide composed of randomly distributed β-(1→4)-linked D-glucosamine (deacetylated unit) and N-acetyl-D-glucosamine (acetylated unit). It is made by treating the chitin shells of shrimp and other crustaceans with an alkaline substance, like sodium hydroxide. Therefore, In the context of the present invention, the term "chitosan" refers to an at least partially deacetylated product derived from chitin having the CAS number 9012-76-4. Its chemical structure corresponds to the following formula:

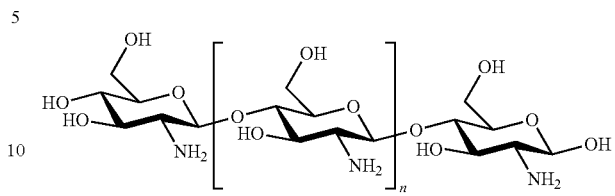

The degree of deacetylation may vary, and the term "chitosan" is not limited to a specific degree of deacetylation. In the context of the application, the term "degree of deacetylation" refers to the proportion of acetylamino groups in the 2-position of the carbohydrate units comprising the chitosan which have been converted to free amino groups, or salts thereof.

The term "chitosan" also encompasses chitosan salts thereof. Examples of chitosan salts include hydrochloride, chitosan hydrobromide, chitosan phosphate, chitosan formate, chitosan acetate, chitosan propionate, chitosan chloroacetate, chitosan hydroxy acetate, chitosan butyrate, chitosan isobutyrate, chitosan acrylate, or mixtures thereof.

In an embodiment, the methacrylate or acrylate modified polysaccharide is selected from the group consisting of a methacrylate modified chitosan having a degree of substitution of the methacrylate groups from 1% to 100% of the repeating units of chitosan and comprising repeating units of formula (VII);

(VII)

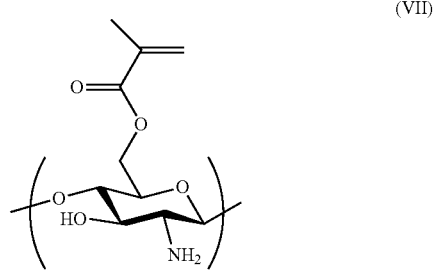

and an acrylate modified chitosan having a degree of substitution of the acrylate groups from 1% to 100% of the repeating units of chitosan and comprising repeating units of formula (VIII);

(VIII)

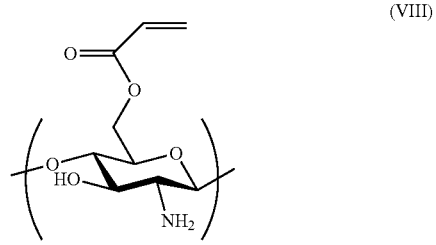

The methacrylate or acrylate modified hyaluronic acid, alginate, gellan gum, cellulose and derivative thereof, glycogen and chitosan disclosed in the present invention can be prepared following the general procedure disclosed for the methacrylate or acrylate modified dextran using as starting material the appropriate polysaccharide.

In an embodiment, the use of the invention relates to the use of a single-chain polysaccharide methacrylate or acrylate-based nanoparticle having a surface tension measured by Du Noüy Ring method equal to or lower than 63 mN/m, particularly a surface tension measured by Du Noüy Ring method equal to or lower than 60 mN/m, as oil-in-water emulsion stabilizer. In an embodiment, the use of the invention relates to the use of a single-chain polysaccharide methacrylate-based nanoparticle having a surface tension measured by Du Noüy Ring method equal to or lower than 63 mN/m particularly a surface tension measured by Du Noüy Ring method equal to or lower than 60 mN/m, as oil-in-water emulsion stabilizer. In an embodiment, the use of the invention relates to the use of a single-chain polysaccharide acrylate-based nanoparticle having a surface tension measured by Du Noüy Ring method equal to or lower than 63 mN/m particularly a surface tension measured by Du Noüy Ring method equal to or lower than 60 mN/m, as oil-in-water emulsion stabilizer.

In an embodiment, the single-chain polysaccharide methacrylate or acrylate-based nanoparticle of the present invention comprises a percentage of intra-molecular crosslinking from 1 to 60 molar % of the total amount of monomer units present in the polysaccharide methacrylate or acrylate chain. In an embodiment, the single-chain polysaccharide methacrylate or acrylate-based nanoparticle of the present invention comprises a percentage of intra-molecular crosslinking from 1 to 50 molar % of the total amount of monomer units present in the polysaccharide methacrylate or acrylate chain.

The term "molar %" as used herein refers to the mole fraction or molar fraction, which is the amount of an ingredient expressed in moles, divided by the total amount of monomer units present in the polysaccharide methacrylate or acrylate chain.

For the purpose of the invention, the term "intra-molecular crosslinking" refers to those bonds that link one methacrylate or acrylate reactive group of the polysaccharide with a crosslinkable group of the crosslinking agent by hydrolysable covalent bonding of a single-chain. This intra-molecular crosslinking bonds are responsible for generating the three-dimensional structure of the single-stranded nanoparticles. In the context of the invention, the term "intra-molecular crosslinking" does not encompasses the "interfacial crosslinking" bonds as defined herein below which are generated in the interfacial layer of the emulsion.

The single-chain polysaccharide methacrylate or acrylate-based nanoparticle is a single-chain dextran methacrylate or acrylate-based nanoparticle having a surface tension measured by Du Noüy Ring method equal to or lower than 63 mN/m, particularly a surface tension measured by Du Noüy Ring method equal to or lower than 60 mN/m; a degree of substitution of the methacrylate or acrylate groups from 1% to 98% of modified repeating units of the nanoparticles; and a percentage of intra-molecular crosslinking from 1 to 60 molar % of the total amount of monomer units present in the dextran methacrylate or acrylate chain; particularly from 1 to 50 molar %.

In an embodiment, the single-chain polysaccharide methacrylate or acrylate-based nanoparticle is a single-chain dextran methacrylate or acrylate-based nanoparticle comprising repeating units of formula (III)

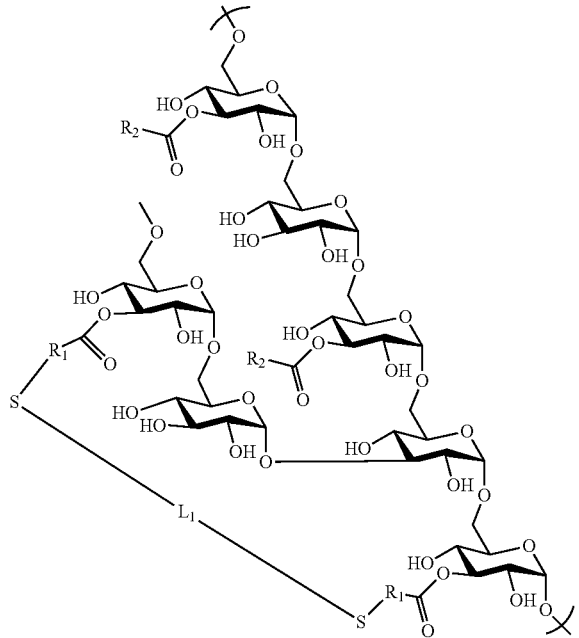

(III)

wherein:
$R_1$ is selected from the group consisting of —$CH_2$—$CH_2$— and —$CH_2$—$CH(CH_3)$—;
$R_2$ is selected from the group consisting of —$CH(=CH_2)$ and —$C(=CH_2)(CH_3)$,
$L_1$ is a biradical selected from the group consisting of —[$(CH_2)_r$—O]$_q$—$(CH_2)_r$— and —$(CH_2)_s$—;
q is an integer from 2 to 3;
r is an integer from 2 to 4;
s is an integer from 2 to 5; and
the nanoparticle has:
a degree of substitution of the methacrylate or acrylate groups from 1% to 98% of modified repeating units of the nanoparticles; and
a percentage of intra-molecular crosslinking from 1 to 60 molar % of the total amount of monomer units present in the dextran methacrylate or acrylate chain; particularly from 1 to 50 molar %.

In an embodiment, the single-chain polysaccharide methacrylate or methacrylate-based nanoparticle is a single-chain dextran methacrylate-based nanoparticle comprising repeating units of formula (III), wherein $R_1$ is —$CH_2$—$CH(CH_3)$— and $R_2$ is —$C(=CH_2)(CH_3)$.

In an embodiment, the single-chain polysaccharide acrylate or acrylate-based nanoparticle is a single-chain dextran acrylate-based nanoparticle comprising repeating units of formula (III), wherein $R_1$ is —$CH_2$—$CH_2$— and $R_2$ is —$CH(=CH_2)$.

In an embodiment, the single-chain polysaccharide methacrylate or single-chain polysaccharide acrylate-based nanoparticle is a single-chain dextran methacrylate or dextran acrylate-based nanoparticle comprising repeating units of formula (III), wherein $L_1$ is —[$(CH_2)_r$—O]$_q$—$(CH_2)_r$— and q and r are as defined in the present invention.

In an embodiment, the single-chain polysaccharide methacrylate or single-chain polysaccharide acrylate-based nanoparticle is a single-chain dextran methacrylate or dextran acrylate-based nanoparticle comprising repeating units of formula (III), wherein $L_1$ is —$(CH_2)_2$—O—$(CH_2)_2$—O—$(CH_2)_2$—.

In an embodiment, the single-chain polysaccharide methacrylate-based nanoparticle is a single-chain dextran methacrylate-based nanoparticle comprising repeating units of formula (III), wherein $R_1$ is —$CH_2$—$CH(CH_3)$—, $R_2$ is —$C(=CH_2)(CH_3)$ and $L_1$ is —$[(CH_2)_r$—$O]_q$—$(CH_2)_r$— and q and r are as defined in the present invention; particularly $L_1$ is —$(CH_2)_2$—O—$(CH_2)_2$—O—$(CH_2)_2$—.

In an embodiment, the single-chain polysaccharide acrylate-based nanoparticle is a single-chain dextran acrylate-based nanoparticle comprising repeating units of formula (III), wherein $R_1$ is —$CH_2$—$CH_2$—, $R_2$ is —$CH(=CH_2)$ and $L_1$ is —$[(CH_2)_r$—$O]_q$—$(CH_2)_r$— and q and r are as defined in the present invention; particularly $L_1$ is —$(CH_2)_2$—O—$(CH_2)_2$—O—$(CH_2)_2$—.

In an embodiment, the single-chain polysaccharide methacrylate or acrylate-based nanoparticle is a single-chain hyaluronic acid methacrylate or acrylate-based nanoparticle having a surface tension measured by Du Noüy Ring method equal to or lower than 63 mN/m, particularly a surface tension measured by Du Noüy Ring method equal to or lower than 60 mN/m; a degree of substitution of the methacrylate or acrylate groups from 1% to 98% of modified repeating units of the nanoparticles; and a percentage of intra-molecular crosslinking from 1 to 60 molar % of the total amount of monomer units present in the hyaluronic acid methacrylate or acrylate chain; particularly from 1 to 50 molar %.

In an embodiment, the single-chain polysaccharide methacrylate or acrylate-based nanoparticle is a single-chain hyaluronic acid methacrylate or acrylate-based nanoparticle comprising repeating units of formula (VI)

in the hyaluronic acid methacrylate or acrylate chain; particularly from 1 to 50 molar %.

In an embodiment, the single-chain polysaccharide methacrylate-based nanoparticle is a single-chain hyaluronic acid methacrylate-based nanoparticle comprising repeating units of formula (VI), wherein $R_1$ is —$CH_2$—$CH(CH_3)$— and $R_2$ is —$C(=CH_2)(CH_3)$.

In an embodiment, the single-chain polysaccharide acrylate-based nanoparticle is a single-chain hyaluronic acid acrylate-based nanoparticle comprising repeating units of formula (VI), wherein $R_1$ is —$CH_2$—$CH_2$— and $R_2$ is —$CH(=CH_2)$.

In an embodiment, the single-chain polysaccharide methacrylate or single-chain polysaccharide acrylate-based nanoparticle is a single-chain of hyaluronic acid methacrylate or hyaluronic acid acrylate-based nanoparticle comprising repeating units of formula (VI), wherein $L_1$ is —$[(CH_2)_r$—$O]_q$—$(CH_2)_r$— and q and r are as defined in the present invention.

In an embodiment, the single-chain polysaccharide methacrylate or single-chain polysaccharide acrylate-based nanoparticle is a single-chain hyaluronic acid methacrylate or hyaluronic acid acrylate-based nanoparticle comprising repeating units of formula (VI), wherein $L_1$ is —$(CH_2)_2$—O—$(CH_2)_2$—O—$(CH_2)_2$—.

In an embodiment, the single-chain polysaccharide methacrylate-based nanoparticle is a single-chain of hyaluronic acid methacrylate-based nanoparticle comprising repeating units of formula (VI), wherein $R_1$ is —$CH_2$—$CH(CH_3)$—, $R_2$ is —$C(=CH_2)(CH_3)$ and $L_1$ is —$[(CH_2)_r$—$O]_q(CH_2)_r$—

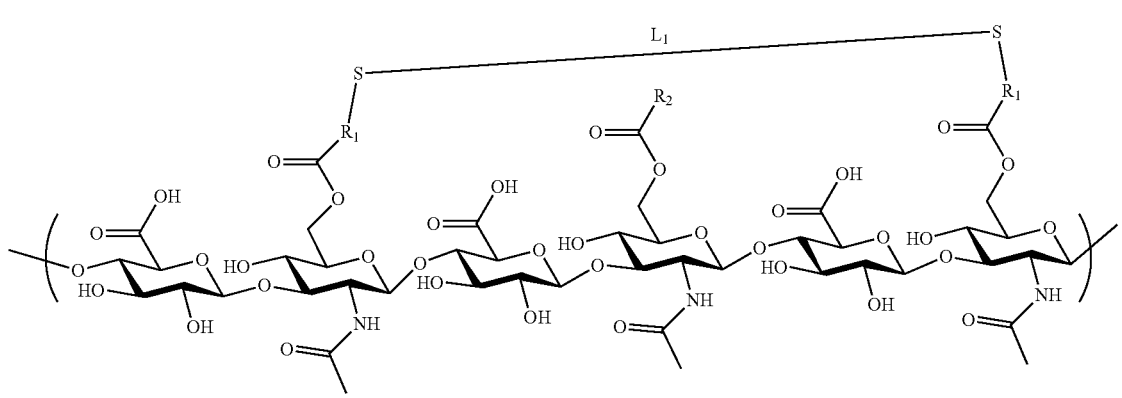

(VI)

wherein:
$R_1$ is selected from the group consisting of —$CH_2$—$CH_2$— and —$CH_2$—$CH(CH_3)$—;
$R_2$ is selected from the group consisting of —$CH(=CH_2)$ and —$C(=CH_2)(CH_3)$;
$L_1$ is a biradical selected from the group consisting of —$[(CH_2)_r$—$O]_q(CH_2)_r$— and —$(CH_2)_s$—;
q is an integer from 2 to 3;
r is an integer from 2 to 4;
s is an integer from 2 to 5; and
the nanoparticle has:
  a degree of substitution of the methacrylate or acrylate groups from 1% to 98% of modified repeating units of the nanoparticles; and
  a percentage of intra-molecular crosslinking from 1 to 60 molar % of the total amount of monomer units present and q and r are as defined in the present invention; particularly $L_1$ is —$(CH_2)_2$—O—$(CH_2)_2$—O—$(CH_2)_2$—.

In an embodiment, the single-chain polysaccharide acrylate-based nanoparticle is a single-chain of hyaluronic acid acrylate-based nanoparticle comprising repeating units of formula (VI), wherein $R_1$ is —$CH_2$—$CH_2$—, $R_2$ is —$CH(=CH_2)$ and $L_1$ is —$[(CH_2)_r$—$O]_q(CH_2)_r$— and q and r are as defined in the present invention; particularly $L_1$ is —$(CH_2)_2$—O—$(CH_2)_2$—O—$(CH_2)_2$—.

In an embodiment, the single-chain polysaccharide methacrylate or acrylate-based nanoparticle is a single-chain alginate methacrylate or acrylate-based nanoparticle having: a degree of substitution of the methacrylate or acrylate groups from 1% to 98% of modified repeating units of the nanoparticles; and a percentage of intra-molecular crosslinking from 1 to 60 molar % of the total amount of monomer units present in the alginate methacrylate or acrylate chain.

In an embodiment, the single-chain polysaccharide methacrylate or acrylate-based nanoparticle is a single-chain alginate methacrylate based nanoparticle having: a degree of substitution of the methacrylate groups from 1% to 98% of modified repeating units of the nanoparticles; and a percentage of intra-molecular crosslinking from 1 to 60 molar % of the total amount of monomer units present in the alginate methacrylate chain.

In an embodiment, the single-chain polysaccharide methacrylate or acrylate-based nanoparticle is a single-chain alginate acrylate-based nanoparticle having: a degree of substitution of the acrylate groups from 1% to 98% of modified repeating units of the nanoparticles; and a percentage of intra-molecular crosslinking from 1 to 60 molar % of the total amount of monomer units present in the alginate acrylate chain.

In an embodiment, the single-chain polysaccharide methacrylate or acrylate-based nanoparticle is a single-chain cellulose methacrylate or acrylate-based nanoparticle having: a degree of substitution of the methacrylate or acrylate groups from 1% to 98% of modified repeating units of the nanoparticles; and a percentage of intra-molecular crosslinking from 1 to 60 molar % of the total amount of monomer units present in the cellulose methacrylate or acrylate chain; particularly hydroxyethylcellulose and methylcellulose.

In an embodiment, the single-chain polysaccharide methacrylate or acrylate-based nanoparticle is a single-chain cellulose methacrylate-based nanoparticle having: a degree of substitution of the methacrylate groups from 1% to 98% of modified repeating units of the nanoparticles; and a percentage of intra-molecular crosslinking from 1 to 60 molar % of the total amount of monomer units present in the cellulose methacrylate chain; particularly hydroxyethylcellulose and methylcellulose.

In an embodiment, the single-chain polysaccharide methacrylate or acrylate-based nanoparticle is a single-chain cellulose acrylate-based nanoparticle having: a degree of substitution of the acrylate groups from 1% to 98% of modified repeating units of the nanoparticles; and a percentage of intra-molecular crosslinking from 1 to 60 molar % of the total amount of monomer units present in the cellulose acrylate chain, particularly hydroxyethylcellulose and methylcellulose.

In an embodiment, the single-chain polysaccharide methacrylate or acrylate-based nanoparticle is a single-chain glycogen methacrylate or acrylate-based nanoparticle having: a degree of substitution of the methacrylate or acrylate groups from 1% to 98% of modified repeating units of the nanoparticles; and a percentage of intra-molecular crosslinking from 1 to 60 molar % of the total amount of monomer units present in the glycogen methacrylate or acrylate chain.

In an embodiment, the single-chain polysaccharide methacrylate or acrylate-based nanoparticle is a single-chain glycogen methacrylate-based nanoparticle having: a degree of substitution of the methacrylate groups from 1% to 98% of modified repeating units of the nanoparticles; and a percentage of intra-molecular crosslinking from 1 to 60 molar % of the total amount of monomer units present in the glycogen methacrylate chain.

In an embodiment, the single-chain polysaccharide methacrylate or acrylate-based nanoparticle is a single-chain glycogen acrylate-based nanoparticle having: a degree of substitution of the acrylate groups from 1% to 98% of modified repeating units of the nanoparticles; and a percentage of intra-molecular crosslinking from 1 to 60 molar % of the total amount of monomer units present in the glycogen acrylate chain. In an embodiment, the single-chain polysaccharide methacrylate or acrylate-based nanoparticle is a single-chain chitosan methacrylate or acrylate-based nanoparticle having: a degree of substitution of the methacrylate or acrylate groups from 1% to 98% of modified repeating units of the nanoparticles; and a percentage of intra-molecular crosslinking from 1 to 60 molar % of the total amount of monomer units present in the chitosan methacrylate or acrylate chain.

In an embodiment, the single-chain polysaccharide methacrylate or acrylate-based nanoparticle is a single-chain chitosan methacrylate-based nanoparticle having: a degree of substitution of the methacrylate groups from 1% to 98% of modified repeating units of the nanoparticles; and a percentage of intra-molecular crosslinking from 1 to 60 molar % of the total amount of monomer units present in the chitosan methacrylate chain.

In an embodiment, the single-chain polysaccharide methacrylate or acrylate-based nanoparticle is a single-chain chitosan acrylate-based nanoparticle having: a degree of substitution of the acrylate groups from 1% to 98% of modified repeating units of the nanoparticles; and a percentage of intra-molecular crosslinking from 1 to 60 molar % of the total amount of monomer units present in the chitosan acrylate chain.

In an embodiment, the single-chain polysaccharide methacrylate or acrylate-based nanoparticle is a single-chain chitosan methacrylate or acrylate-based nanoparticle having a surface tension measured by Du Noüy Ring method equal to or lower than 63 mN/m, particularly a surface tension measured by Du Noüy Ring method equal to or lower than 60 mN/m; a degree of substitution of the methacrylate or acrylate groups from 1% to 98% of modified repeating units of the nanoparticles; and a percentage of intra-molecular crosslinking from 1 to 60 molar % of the total amount of monomer units present in the chitosan methacrylate or acrylate chain; particularly from 1 to 50 molar %.

In an embodiment, the single-chain polysaccharide methacrylate or acrylate-based nanoparticle is a single-chain chitosan methacrylate or acrylate-based nanoparticle comprising repeating units of formula (IX)

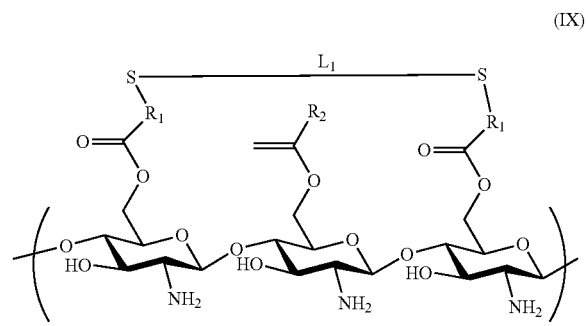

(IX)

wherein:
$R_1$ is selected from the group consisting of $-CH_2-CH_2-$ and $-CH_2-CH(CH_3)-$;
$R_2$ is selected from the group consisting of $-CH(=CH_2)$ and $-C(=CH_2)(CH_3)$;
$L_1$ is a biradical selected from the group consisting of $-[(CH_2)_r O]_q-(CH_2)_r-$ and $-(CH_2)_s-$;
q is an integer from 2 to 3;
r is an integer from 2 to 4;
s is an integer from 2 to 5; and the nanoparticle has:
  a degree of substitution of the methacrylate or acrylate groups from 1% to 98% of modified repeating units of the nanoparticles; and
  a percentage of intra-molecular crosslinking from 1 to 60 molar % of the total amount of monomer units present in the chitosan methacrylate or acrylate chain; particularly from 1 to 50 molar %.

In an embodiment, the single-chain polysaccharide methacrylate-based nanoparticle is a single-chain chitosan methacrylate-based nanoparticle comprising repeating units of formula (IX), wherein $R_1$ is —$CH_2$—$CH(CH_3)$— and $R_2$ is —$C(=CH_2)(CH_3)$.

In an embodiment, the single-chain polysaccharide acrylate-based nanoparticle is a single-chain chitosan acrylate-based nanoparticle comprising repeating units of formula (IX), wherein $R_1$ is —$CH_2$—$CH_2$— and $R_2$ is —$CH(=CH_2)$.

In an embodiment, the single-chain polysaccharide methacrylate or single-chain polysaccharide acrylate-based nanoparticle is a single-chain of chitosan methacrylate or hyaluronic acid acrylate-based nanoparticle comprising repeating units of formula (IX), wherein $L_1$ is —[$(CH_2)_r$—$O]_q$($CH_2)_r$— and q and r are as defined in the present invention.

In an embodiment, the single-chain polysaccharide methacrylate or single-chain polysaccharide acrylate-based nanoparticle is a single-chain chitosan methacrylate or hyaluronic acid acrylate-based nanoparticle comprising repeating units of formula (IX), wherein $L_1$ is —$(CH_2)_2$—O—$(CH_2)_2$—O—$(CH_2)_2$.

In an embodiment, the single-chain polysaccharide methacrylate-based nanoparticle is a single-chain of chitosan methacrylate-based nanoparticle comprising repeating units of formula (IX), wherein $R_1$ is —$CH_2$—$CH(CH_3)$—, $R_2$ is —$C(=CH_2)(CH_3)$ and $L_1$ is —[$(CH_2)_r$—$O]_q$($CH_2)_r$— and q and r are as defined in the present invention; particularly $L_1$ is —$(CH_2)_2$—O—$(CH_2)_2$—O—$(CH_2)_2$—.

In an embodiment, the single-chain polysaccharide acrylate-based nanoparticle is a single-chain of chitosan acrylate-based nanoparticle comprising repeating units of formula (IX), wherein $R_1$ is —$CH_2$—$CH_2$—, $R_2$ is —$CH(=CH_2)$ and $L_1$ is —[$(CH_2)_r$—$O]_q$—$(CH_2)_r$— and q and r are as defined in the present invention; particularly $L_1$ is —$(CH_2)_2$—O—$(CH_2)_2$—O—$(CH_2)_2$—.

The single-chain polysaccharide methacrylate or acrylate-based nanoparticles disclosed in the present application can be prepared by cross-linking a polysaccharide methacrylate or acrylate as defined in the present application with a homobifunctional crosslinking agent having crosslinkable groups; by a process comprising:
  (i) adding an aqueous solution of the polysaccharide methacrylate or acrylate as defined in the first aspect of the invention to an aqueous solution of the homobifunctional crosslinking agent; or alternatively,
  (ii) adding an aqueous solution of the homobifunctional crosslinking agent to an aqueous solution of the dextran methacrylate or acrylate as defined in the first aspect of the invention to an aqueous solution; or alternatively,
  (iii) mixing a solution of the homobifunctional crosslinking agent and an aqueous solution of the dextran methacrylate or acrylate as defined in the first aspect of the invention to an aqueous solution;
at a temperature from 20 to 25° C.
optionally in the present of a catalyst;

optionally the process further comprises an additional step of purifying the single-chain polysaccharide methacrylate or acrylate-based nanoparticle, and
optionally the process further comprises an additional step of drying the single-chain polysaccharide methacrylate or acrylate-based nanoparticle.

The single-chain polysaccharide methacrylate or acrylate-based nanoparticles disclosed in the present application can be prepared by cross-linking a polysaccharide methacrylate or acrylate as defined in the present application with a homobifunctional crosslinking agent having crosslinkable groups. The process for their preparation is disclosed in the state of the art (cf. PCT patent application WO2016071258).

As it is mentioned above, the second aspect of the invention relates to an oil-in-water emulsion stabilizer composition comprising: a methacrylate or acrylate modified polysaccharide; or alternatively, a single-chain polysaccharide methacrylate or acrylate-based nanoparticle as defined in the present application; and one or more appropriate excipients or carriers. These compositions are advantageous because in contact with an aqueous phase and an oily phase, a stable oil-in-water emulsion as defined in the present invention is obtained.

All the embodiment disclosed in the first aspect of the invention for the methacrylate or acrylate modified polysaccharide and a single-chain polysaccharide methacrylate or acrylate-based nanoparticle, also apply for the oil-in-water emulsion stabilizer composition of the second aspect of the invention.

The oil-in-water emulsion stabilizer composition of the present invention can be prepared according to methods well known in the state of the art. The appropriate excipients and/or carriers, and their amounts, can readily be determined by those skilled in the art according to the type of formulation being prepared.

The third aspect of the invention relates to an oil-in-water emulsion comprising:
  (a) the external water phase (W) comprising:
    (a1) a solvent selected from the group consisting of water, glycol and a mixture thereof; particularly water; and
    (a2) optionally, one or more hydrophilic compounds selected from the group consisting of: (a2') hydrophilic active agent and (a2") hydrophilic excipients or carriers;
  (b) the internal oily phase (O) comprising one or more lipophilic compounds selected from the group consisting of:
  (b1) lipophilic active agents, and
  (b2) lipophilic excipients or carriers;
  and
  (c) an interfacial layer (IL) between the external water phase (W) and the internal oily phase (O) comprising:
  (c1) one or more emulsion stabilizer selected from the group consisting of:
  (c1') methacrylate or acrylate modified polysaccharides as defined in the present invention;
  (c1") single-chain polysaccharide methacrylate or acrylate-based nanoparticles as defined in in the present invention;
  (c1''') interfacial crosslinked methacrylate or acrylate modified polysaccharides obtainable by reacting the methacrylate or acrylate modified polysaccharides as defined in in the present invention with an interfacial crosslinking agent, wherein the interfacial crosslinked methacrylate or acrylate modified polysaccharides has an interfacial crosslinking degree from 25 to 100% of the methacrylate or acrylate groups of the polysaccharide; or alternatively, (c1'''') interfacial crosslinked single-chain polysaccharide methacrylate or acrylate based nanoparticles obtainable by reacting the single-chain polysaccharide methacrylate or acrylate-based nanoparticles as defined in in the present invention with an interfacial crosslinking agent, wherein the interfacial crosslinked single-chain polysaccharide methacrylate or acrylate based nanoparticles has an interfacial crosslinking degree from 25 to 100% of the methacrylate or acrylate groups of the nanoparticles; and c2) optionally, one or more hydrophilic active agents.

As it is demonstrated in the experimental section of the present application, the oil-in-water emulsions of the present invention are stable in the manufacturing, storage and use conditions. Furthermore, they also have esterase enzyme response which allows their use as a delivery platform for active ingredients, even allowing the kinetic control of the delivery of the drug from the emulsion. It is also demonstrated that the emulsions comprising an interfacial crosslinked polysaccharide or nanoparticles of the present inventive in the interfacial phase of the oil-in-water emulsion have an improved stability but without compromising the esterase enzyme response.

The term "emulsion" refers to dispersed system comprising at least two immiscible phases, one phase dispersed in the other as droplets. When the aqueous phase is the dispersed phase and oil is the dispersion medium, the emulsion is termed a water-in-oil emulsion (w/o). When oil is dispersed as droplets throughout the aqueous phase, the emulsion is termed an oil-in-water emulsion (o/w). For the purpose of the invention the term "water-in-oil emulsion" encompasses emulsion having an external aqueous phase (or water phase) comprising a solvent selected from the group consisting of a solvent selected from the group consisting of water, glycol and a mixture thereof.

As it is mentioned above, the external water phase (W) comprises: (a1) a solvent selected from the group consisting of water, glycol and a mixture thereof; particularly water; and (a2) optionally, one or more hydrophilic compounds selected from the group consisting of: (a2') hydrophilic active agent and (a2'') hydrophilic excipients or carriers.

The term "glycol" refers to a straight or branched chain hydrocarbon having at least two hydroxyl substituents. Commonly the glycol has from about two to about twelve carbon atoms ($C_2$-$C_{12}$). As used herein, the term "glycol" also encompasses polymeric versions of the glycols described herein. Examples of polymeric glycols include ethylene glycol and polyethylene glycol. In an embodiment, the glycol is glycerine.

In an embodiment, the external water phase (W) consists of water (a1).

In an embodiment, the external water phase (W) consists of glycol (a1).

In an embodiment, the external water phase (W) consists of a mixture of water and glycol (a1).

In an embodiment, the external water phase (a) consists of water (a1) and one or more hydrophilic compounds (a2) selected from the group consisting of: (a2') hydrophilic active agent and (a2'') hydrophilic excipients or carriers.

In an embodiment, the external water phase (a) consists of glycol (a1) and one or more hydrophilic compounds (a2) selected from the group consisting of: (a2') hydrophilic active agent and (a2'') hydrophilic excipients or carriers.

In an embodiment, the external water phase (a) consists of a mixture of water and glycol (a1) and one or more hydrophilic compounds (a2) selected from the group consisting of: (a2') hydrophilic active agent and (a2'') hydrophilic excipients or carriers.

In an embodiment, the external water phase (a) comprises water (a1) and one or more hydrophilic compounds (a2) selected from the group consisting of: (a2') hydrophilic active agent and (a2'') hydrophilic excipients or carriers.

In an embodiment, the external water phase (a) comprises glycol (a1) and one or more hydrophilic compounds (a2) selected from the group consisting of: (a2') hydrophilic active agent and (a2'') hydrophilic excipients or carriers.

In an embodiment, the external water phase (a) comprises a mixture of water and glycol (a1) and one or more hydrophilic compounds (a2) selected from the group consisting of: (a2') hydrophilic active agent and (a2'') hydrophilic excipients or carriers.

In an embodiment, the one or more hydrophilic compound is one or more hydrophilic active agents (a2').

In an embodiment, the one or more hydrophilic compound is one or more hydrophilic excipients or carriers (a2'').

In an embodiment, the one or more hydrophilic compound is a mixture of one or more hydrophilic active agents (a2') and one or more hydrophilic excipients or carriers (a2'').

The terms "hydrophilic" and "polar" have the same meaning and are used interchangeable. They refer to a compound, active agent, excipients or carriers capable of creating hydrogen bonding, enabling them to be dissolved more readily in water, and in other polar solvents. The appropriate "hydrophilic excipients and/or carriers", and their amounts, can readily be determined by those skilled in the art according to the type of formulation being prepared.

In an embodiment, the one or more hydrophilic compound is one or more hydrophilic excipients or carriers (a2'') being one or more water-miscible organic solvents. The term "miscible organic solvent" refers to an organic solvent that, when combined, form a single phase, which means that the mixture thus obtained is "monophasic" under specified conditions of component concentrations and temperature among others. Further, the term "water-miscible organic solved" refers to an organic solvent that can form a monophasic solution with water at the temperature at which the reaction is carried out. As used herein, the term "monophasic" refers to a reaction medium that includes only one liquid phase, and also a method employing such a reaction medium. In an embodiment, the one or more hydrophilic compound is one or more water-miscible organic solvents selected from the group consisting of ($C_1$-$C_6$) alcohol, ($C_1$-$C_4$) alkyl-CO—($C_1$-$C_4$) alkyl, ($C_1$-$C_4$) alkyl-CO—O—($C_1$-$C_4$) alkyl and mixtures thereof. The term "alcohol" refers to an "alkane" wherein at least one hydrogen atom is substituted by a hydroxyl group and which contains the number of carbon atoms specified in the description or claims. Examples include glycerol, ethanol, n-propanol, iso-propanol, butanol, iso-butanol, and sec-butanol. The term "alkyl" refers to a saturated straight, or branched hydrocarbon chain which contains the number of carbon atoms specified in the description or claims. Examples include, among others, the group methyl, ethyl, propyl, isopropyl, butyl, isobutyl, sec-butyl, and tert-butyl.

As it is mentioned above, the internal oily phase (O) comprises one or more lipophilic compounds selected from the group consisting of: (b1) lipophilic active agents, and (b2) lipophilic excipients or carriers.

In an embodiment, the oily phase (O) consists of one or more lipophilic active agents (b1). In an embodiment, the oily phase (O) comprises one or more lipophilic active agents (b1). In an embodiment, the oily phase (O) consists of one or more lipophilic excipients or carriers (b2). In an embodiment, the oily phase (O) comprises one or more lipophilic excipients or carriers (b2). In an embodiment, the oily phase (O) consist of one or more lipophilic active agents (b1) and one or more lipophilic excipients or carriers (b2). In an embodiment, the oily phase (O) comprises one or more lipophilic active agents (b1) and one or more lipophilic excipients or carriers The terms "lipophilic", "hydrophobic" and "non-polar" have the same meaning and are used interchangeable. They refer to a compound, active agent, excipients or carriers which prefer other neutral molecules and non-polar solvents rather than water. Lipophilic molecules in water often can form aggregates than can only be redispersed in water but not dissolved. For the purpose of the invention the term "lipophilic excipients and/or carriers" encompasses "lipophilic" solvents that have little or no capacity to form hydrogen bonds, enabling them to be dissolved in fats, oils, lipids, and other non-polar solvents. Examples of "lipophilic" solvents include, without limitation, vegetable oils, mineral oils, animal fats, ($C_6$-$C_{20}$) alkanes, ($C_6$-$C_{20}$) halogen-alkanes and mixture thereof. The term "alkane" refers to a saturated, branched or linear hydrocarbon which contains the number of carbon atoms specified in the description or claims. Examples include n-pentane, n-hexane, n-octane, n-dodecane and a mixture thereof. The term "halogen-alkane" refers to an alkane in that at least one hydrogen atom is substituted by one or more halogen atoms and which contains the number of carbon atoms specified in the description or claims. Examples of halogen-alkane include chloroform, trichloroethane, dichloromethane and a mixture thereof.

In an embodiment, the "lipophilic" solvents are selected from the group consisting of vegetable oils, mineral oils, animal fats and a mixture thereof. In an embodiment, the "lipophilic" solvents are selected from the group consisting of ($C_6$-$C_{20}$) alkanes, ($C_6$-$C_{20}$) halogen-alkanes and a mixture thereof.

The appropriate "lipophilic excipients and/or carriers", and their amounts, can readily be determined by those skilled in the art according to the type of formulation being prepared.

As it is mentioned above, the interfacial layer (IL) between the external water phase (W) and the internal oily phase (O) comprising:

(c1) one or more emulsion stabilizer selected from the group consisting of:
(c1') methacrylate or acrylate modified polysaccharides as defined in the first aspect of the invention;
(c1") single-chain polysaccharide methacrylate or acrylate-based nanoparticles as defined in the first aspect of the invention;
(c1''') interfacial crosslinked methacrylate or acrylate modified polysaccharides obtainable by reacting the methacrylate or acrylate modified polysaccharides as defined in the first aspect of the invention with an interfacial crosslinking agent, wherein the interfacial crosslinked methacrylate or acrylate modified polysaccharides has an interfacial crosslinking degree from 25 to 100% of the methacrylate or acrylate groups of the polysaccharide; or alternatively,
(c1'''') interfacial crosslinked single-chain polysaccharide methacrylate or acrylate based nanoparticles obtainable by reacting the single-chain polysaccharide methacrylate or acrylate based nanoparticles as defined in as defined in the first aspect of the invention with an interfacial crosslinking agent, wherein the interfacial crosslinked single-chain polysaccharide methacrylate or acrylate based nanoparticles has an interfacial crosslinking degree from 25 to 100% of the methacrylate or acrylate groups of the nanoparticles;
and
(c2) optionally, one or more hydrophilic active agents.

In an embodiment, the interfacial layer (IL) between the external water phase (W) and the internal oily phase (O) comprising one or more methacrylate or acrylate modified polysaccharides as defined in the first aspect of the invention (c1') as emulsion stabilizer. In an embodiment, the interfacial layer (IL) between the external water phase (W) and the internal oily phase (O) consist of one or more methacrylate or acrylate modified polysaccharides as defined in the first aspect of the invention (c1') as emulsion stabilizer. In an embodiment, the interfacial layer (IL) between the external water phase (W) and the internal oily phase (O) comprising one or more single-chain polysaccharide methacrylate or acrylate-based nanoparticles as defined in the first aspect of the invention (c1") as emulsion stabilizer. In an embodiment, the interfacial layer (IL) between the external water phase (W) and the internal oily phase (O) consist of one or more single-chain polysaccharide methacrylate or acrylate-based nanoparticles as defined in the first aspect of the invention (c1") as emulsion stabilizer.

In an embodiment, the interfacial layer (IL) between the external water phase (W) and the internal oily phase (O) comprising one or more interfacial crosslinked methacrylate or acrylate modified polysaccharides obtainable by reacting the methacrylate or acrylate modified polysaccharides as defined in the first aspect of the invention with an interfacial crosslinking agent, wherein the interfacial crosslinked methacrylate or acrylate modified polysaccharides has an interfacial crosslinking degree from 25 to 100% of the methacrylate or acrylate groups of the polysaccharide (c1''') as emulsion stabilizer. In an embodiment, the interfacial layer (IL) between the external water phase (W) and the internal oily phase (O) consist of one or more interfacial crosslinked methacrylate or acrylate modified polysaccharides obtainable by reacting the methacrylate or acrylate modified polysaccharides as defined in the first aspect of the invention with an interfacial crosslinking agent, wherein the interfacial crosslinked methacrylate or acrylate modified polysaccharides has an interfacial crosslinking degree from 25 to 90% of the methacrylate or acrylate groups of the polysaccharide (c1''') as emulsion stabilizer. In an embodiment, the interfacial layer (IL) between the external water phase (W) and the internal oily phase (O) comprising one or more interfacial crosslinked single-chain polysaccharide methacrylate or acrylate based nanoparticles obtainable by reacting the single-chain polysaccharide methacrylate or acrylate based nanoparticles as defined in the first aspect of the invention with an interfacial crosslinking agent, wherein the interfacial crosslinked single-chain polysaccharide methacrylate or acrylate based nanoparticles has an interfacial crosslinking degree from 25 to 100% of the methacrylate or acrylate groups of the nanoparticles (c1'''') as emulsion stabilizer. In an embodiment, the interfacial layer (IL) between the external water phase (W) and the internal oily phase (O) consist of one or more interfacial crosslinked single-chain polysaccharide methacrylate or acrylate based nanoparticles obtainable by reacting the single-chain polysaccharide methacrylate or acrylate based nanoparticles as defined in as defined in the first aspect of the invention with an interfacial crosslinking agent, wherein the interfacial crosslinked single-chain polysaccharide methacrylate or acrylate based nanoparticles has an interfacial crosslinking degree from 25 to 90% of the methacrylate or acrylate groups of the nanoparticles (c1''') as emulsion stabilizer.

The expression "obtainable by" is used here to define each specific emulsion containing one or more interfacial crosslinked polysaccharide or interfacial crosslinked nanoparticles of the invention by the process for obtaining it and refers to the product obtainable by any of the corresponding processes disclosed herein. For the purposes of the invention the expressions "obtainable", "obtained" and equivalent expressions are used interchangeably and, in any case, the expression "obtainable" encompasses the expression "obtained".

In an embodiment, the interfacial layer (IL) comprising one or more emulsion stabilizer (c1) as defined above and one or more hydrophilic active agents (c2). It means that the hydrophilic active agent is in the external site of the surface of the interfacial layer which is in contact with the external water phase. In an embodiment, the hydrophilic active agents (c2) are covalently bonded to the emulsion stabilizer (c1).

In an embodiment, the interfacial crosslinker is a lipophilic dithiol-containing compound. In an embodiment, the interfacial crosslinked is 2,2'-(ethylenedioxy)diethanethiol [3,6-dioxa-1,8-octane]-dithiol.

For the purpose of the invention, the term "interfacial crosslinking agent" and "interfacial crosslinker" have the same meaning and are used interchangeable. They refer to those inter-molecular bonds that link one methacrylate or acrylate reactive group of the polysaccharide or single-chain nanoparticles with a crosslinkable group of the crosslinking agent by non-hydrolysable covalent bonding. This inter-molecular crosslinking bonds are responsible for generating the three-dimensional structure in the interfacial layer of the oil-in-water emulsion containing methacrylate or acrylate modified polysaccharides or nanoparticles of the present invention.

The term "interfacial crosslinking degree" refers to the percentage of methacrylate or acrylate groups of the polysaccharide or nanoparticles that reacts with an interfacial crosslinking agent to create a non-hydrolysable covalent bonding. For example, an emulsion of the present invention comprising an interfacial layer (IL) between the external water phase (W) and the internal oily phase (O) comprising one or more interfacial crosslinked single-chain polysaccharide methacrylate or acrylate-based nanoparticles; or alternatively one or more interfacial crosslinked methacrylate or acrylate modified polysaccharide having an interfacial crosslinking degree of 25% of the methacrylate or acrylate groups, means that the 25% of the free methacrylate or acrylate groups of the polysaccharide or nanoparticles are forming a non-hydrolysable covalent bond with the interfacial crosslinker.

In an embodiment, the interfacial layer (IL) between the external water phase (W) and the internal oily phase (O) comprising one or more interfacial crosslinked single-chain polysaccharide methacrylate or acrylate-based nanoparticles; or alternatively one or more interfacial crosslinked methacrylate or acrylate modified polysaccharide having an interfacial crosslinking degree from 25 to 90% of the methacrylate or acrylate groups of the nanoparticles or polysaccharide respectively.

As it is well known for the skilled person in the art, a parameter useful to determine whether a compound is hydrophilic or lipophilic is determining its partition coefficient (P). The partition (P) coefficient is the ratio of concentrations of a particular compound in a mixture of two immiscible phases at equilibrium. Normally one of the solvents chosen is water while the second is hydrophobic such as octanol. Hydrophobic active ingredients have high octanol/water partition coefficients, and hydrophilic compounds have low octanol/water partition coefficients. The log P value is also known as a measure of lipophilicity/hydrophilicity. The logarithm of the ratio of the concentrations of the un-ionized solute in the solvents, at a specific pH, is called log P: The log P value is also known as a measure of lipophilicity:

$$\log P_{oct/wat} = \log\left(\frac{[\text{solute}]_{octanol}}{[\text{solute}]_{water}^{un-ionized}}\right)$$

wherein the "solute" is the active ingredient.

For the purpose of the invention, a compound is considered "hydrophilic" wherein the log P values is lower than 0.1. On the contrary, a compound is considered "lipophilic" wherein the log P value is higher than 0.1.

In an embodiment, the "active agent" is selected from the group consisting of pharmaceutical active ingredient, diagnostic agent and cosmetic agent.

In an embodiment, the emulsion is a pharmaceutical emulsion, comprising: a therapeutically effective amount of at least one pharmaceutical active ingredient or a pharmaceutically acceptable salt thereof as an active agent, and the excipients and/or carriers are pharmaceutically acceptable. In terms of the present invention, "pharmaceutical" emulsion refers to any composition (emulsion) that is intended for use in the treatment of a disease or condition. The expression "therapeutically effective amount" as used herein, refers to the amount of active ingredients that, when administered, which is sufficient to prevent development of, or alleviate to some extent, one or more of the symptoms of the disease or condition. The particular dose of the active ingredients administered according to this invention will of course be determined by the skilled in the art regarding the particular circumstances surrounding the case, including the particular condition being treated, and the similar considerations. The term "pharmaceutically acceptable" refers to that salts, excipients or carriers suitable for use in the pharmaceutical technology for preparing compositions with medical use.

The active ingredient can be selected from hydrophilic or hydrophobic active ingredients, that can be included in the composition of the invention are, but not limited to, vasoactive agents; neuroactive agents; hormones; growth factors; cytokines; anaesthetics; steroids; anticoagulants (such as D-Phe-Pro-Arg chloromethyl keton, an RGD peptide-containing compound, a polylysine-containing compound, heparin, antithrombin compounds, platelet receptor antagonists, anti-thrombin, anti-platelet receptor antibodies, aspirin, prostaglandin inhibitors, platelet inhibitors and ticic antiplatelet peptides); anti-inflammatories (such as steroid nature (including dexamethasone, prednisolone, triamcinolone, fluorometholone, betamethasone, budesonide, hydrocortisone, clobetasone, beclometasone, desoximetasone, methylprednisolone), and non-steroid agents (AINE) (including dicoflenac, aceclofenac, benzydamine, dexketoprofen, etofenamate, fepradinol, ibuprofen, indomethacin, ketoprofen, piroxicam); immunomodulating agents; cytotoxic agents; prophylactic agents; antivirals; antigens, and antibodies; anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anaesthetic agents (such as lidocaine, bupivacaine, and ropivacaine); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms; radiopharmaceutical; analgesic drug; anorectic agent; anti-anaemia agent; anti-asthma agent; anti-diabetic agent; antihistamine (such as diphenydramine, dimetindene, and promethazine); antimuscarinic drug; cardiovascular drug; central nervous system stimulator; central nervous system depressant; anti-depressant; anti-epileptic; anxiolytic agent; hypnotic agent; sedative; beta blocker; homeostatic agent; hormone; vasodilator; vasoconstrictor; vitamin; chemotherapeutics including antivirals (such as acyclovir, penciclovir, valaciclovir, idoxuridine, tromantadine, imiquimod, and metronidazole; antibiotics (such as fusidic acid, mupirocin, gentamicin, neomycin, retapamulin, clindamycin, erythromycin, and chlortetracycline); antifungals (such as imidazole and triazole derivatives, including bifonazole, chlotrimazole, eberconazole, econazole, fenticonazole, flutrimazole, ketoconazole, miconazole, oxiconazole, sertaconazole, thioconazole); nistatin, Naftifine, terbinafine, tolnaftate, and ciclopirox; healing agents (such as *Arnica montana, Centella asiatica*, and becaplermin); local anesthetics (such as lidocaine, benzocaine, and tetracaine); anti-psoriatic agents (such as etanercept, adalimumab, ustekinumab, dithranol, calcipotriol, calcitriol, tacalcitol, and tazarotene); retinoid agents (such as tretinoin, isotretinoin, and adapalene); antiseptic and desinfectant agents (such as chlorhexidine, boric acid, triclosan); tacrolimus; hydroquinone; minoxidil; Finasteride; Gastro-intestinal; Antitussive agents; Expectorants; anti-spasmodics; diuretics; antihemorrhoidals; hypnotics, psychotropic; decongestants; laxant; and antiacid among others.

In an embodiment, the emulsion is a cosmetic emulsion, comprising: a cosmetically effective amount of at least one cosmetic active ingredient or a cosmetically acceptable salt thereof as an active agent, and the excipients and/or carriers are cosmetically acceptable. In terms of the present invention, "cosmetic" emulsion refers to any composition that is non-medical and non-pharmaceutical, hence, to a composition that is not intended for use in the treatment of a disease or condition, particularly to a skin disease or skin condition, or a hair disease or hair condition. The cosmetic compositions according to the present invention are therefore referring in particular to the treatment of the skin or hair in terms of care without intending to treat a disease condition aiming at the healing of said disease. Hence, "cosmetic" emulsion refers to a composition that has an effect on skin or hair care, such as the appearance and comfort of skin or hair without being used as a pharmaceutical or medicament. It means that, the cosmetic emulsion disclosed in the present invention are designed to apply to the body to improve its appearance or to beautify, preserve, condition, cleanse, colour or protect the skin, nails or hair (cf. Academic press Dictionary of Science and Technology, 1992, pp. 531; A terminological Dictionary of the Pharmaceutical Sciences. 2007, pp. 190). Therefore, the above cosmetic emulsions are adjectivally used for a non-medical application. The term used herein "cosmetically effective amount" refers to an amount enough to accomplish efficacies on cosmetic improvements in skin or hair conditions described hereinabove. The particular dose of the active ingredients administered according to this invention will of course be determined by the skilled in the art regarding the particular circumstances surrounding the case, including the particular condition being treated, and the similar considerations. The term "cosmetically acceptable" refers to that salts, excipients or carriers appropriate for use in human skin or hair contact without toxicity, incompatibility, instability, inappropriate allergic response, among others.

In an embodiment, the emulsion is a diagnostic emulsion, comprising: a diagnostically effective amount of at least one diagnostic active ingredient; particularly one or more diagnostic imaging agents, or a diagnostically acceptable salt thereof as an active agent, and the excipients and/or carriers are diagnostically acceptable; particularly diagnostically imaging acceptable.

The term "imaging agent" refers to any substance that is used as a label or enhances specific structures in any imaging technique. In an embodiment, the imaging agent is selected from the group consisting of fluorescent agent, contrast agent and radioimaging agent. Examples of imaging agents appropriate for the present invention include, but are not limited to, transition metals and radioactive transition metals chelated to chelating agents, for instance DTPA (diethylene triamine pentaacetic acid), DOTA (1,4,7,10-Tetraazacyclododecane-1,4,7,10-tetraacetic acid) or NOTA (1,4,7-Triazacyclononane-1,4,7-triacetic acid), fluorescein, rhodamine, and cyane 5,5. In an embodiment, the imaging agent is a "contrast aged". The term "contrast agent" refers to agents that accentuate certain structures that would otherwise be hard to see by usual techniques.

In terms of the present invention, "diagnostic" emulsion refers to any composition (emulsion) that is intended for diagnostic purposes; particularly for imaging diagnostic purposes, in a detection assay where the present or an amount of a target agent can be correlated with a specific disease or condition. The expression "diagnostically effective amount" as used herein, refers to the amount of active ingredients that, when administered, is sufficient to correlate the target agent with a specific disease or condition. The particular dose of the diagnostic or diagnostic imaging active ingredients administered according to this invention will of course be determined by the skilled in the art regarding the particular circumstances surrounding the case, including the particular condition being treated, and the similar considerations. The term "diagnostically acceptable" refers to those salts, excipients or carriers suitable for use in the diagnostic technology for preparing compositions with diagnostic use. In particular, the term "diagnostically imaging acceptable" refers to excipients or carriers suitable for use in the imaging diagnostic technology for preparing compositions with imaging diagnostic use.

In an embodiment, the emulsion comprises an internal oily phase (O) comprising one or more lipophilic agents; particularly one or more pharmaceutically active ingredients.

In an embodiment, the emulsion comprises an external water phase (W) comprising one or more hydrophilic agents; particularly one or more pharmaceutically active ingredients.

In an embodiment, the emulsion comprises an interfacial layer (IL) comprising one or more hydrophilic agents; one or more diagnostic (imaging) active agents.

In an embodiment, the emulsion comprises:
- an internal oily phase (O) comprising one or more lipophilic agents; particularly one or more pharmaceutically active ingredients; and
- an external water phase (W) comprising one or more hydrophilic agents; particularly one or more pharmaceutically active ingredients.

In an embodiment, the emulsion comprises:
- an internal oily phase (O) comprising one or more lipophilic agents; particularly one or more pharmaceutically active ingredients; and
- an interfacial layer (IL) comprising one or more hydrophilic agents; one or more diagnostic (imaging) active agents.

In an embodiment, the emulsion comprises:
- an external water phase (W) comprising one or more hydrophilic agents; particularly one or more pharmaceutically active ingredients; and
- an interfacial layer (IL) comprising one or more hydrophilic agents; one or more diagnostic (imaging) active agents.

In an embodiment, the emulsion comprises:
- an internal oily phase (O) comprising one or more lipophilic agents; particularly one or more pharmaceutically active ingredients;
- an external water phase (W) comprising one or more hydrophilic agents; particularly one or more pharmaceutically active ingredients; and
- an interfacial layer (IL) comprising one or more hydrophilic agents; one or more diagnostic (imaging) active agents.

All the embodiment disclosed in the first aspect of the invention for the methacrylate or acrylate modified polysaccharide and a single-chain polysaccharide methacrylate or acrylate-based nanoparticle, also apply for the oil-in-water emulsion of the third aspect of the invention.

It is also part of the invention a process for the preparation of the oil-in-water emulsion of the present invention.

The process for the preparation of an emulsion of the invention comprising (c1') methacrylate or acrylate modified polysaccharides; or alternatively (c1") single-chain polysaccharide methacrylate or acrylate-based nanoparticles in the interfacial layer (IL) comprises:
(i) Preparing the aqueous phase by mixing the methacrylate or acrylate modified polysaccharide; or alternatively, the single-chain polysaccharide methacrylate or acrylate-based nanoparticle, in water and optionally the one or more hydrophilic compounds (a2);
(ii) Preparing the oily phase by mixing the one or more lipophilic compounds;
(iii) Adding the oily phase of step (ii) on the aqueous phase of step (i); and
(iv) Emulsifying the resulting mixture of step (iii) under such conditions of shear to obtain the emulsion of the present invention.

In an embodiment, step (iv) is performed using high energy process such as ultraturrax, sonication or high-pressure homogenizer) at a temperature from 0 to 95° C.; particularly about 0° C. without stirring.

The process for the preparation of an emulsion of the invention comprising (c1''') interfacial crosslinked methacrylate or acrylate modified polysaccharides obtainable by reacting the methacrylate or acrylate modified polysaccharides as defined in the first aspect of the invention with an interfacial crosslinking agent, wherein the interfacial crosslinked methacrylate or acrylate modified polysaccharides has an interfacial crosslinking degree from 25 to 100% of the methacrylate or acrylate groups of the polysaccharide; or alternatively, (c1'''') interfacial crosslinked single-chain polysaccharide methacrylate or acrylate based nanoparticles obtainable by reacting the single-chain polysaccharide methacrylate or acrylate based nanoparticles as defined in as defined in the first aspect of the invention with an interfacial crosslinking agent, wherein the interfacial crosslinked single-chain polysaccharide methacrylate or acrylate based nanoparticles has an interfacial crosslinking degree from 25 to 100% of the methacrylate or acrylate groups of the nanoparticles in the interfacial layer (IL) comprises:
performing steps (i), (ii), (iii) and (iv) as defined above; and
(v) adding an interfacial crosslinking agent to the resulting emulsion obtained in step (ii) to obtain the interfacial crosslinking emulsion of the invention.

In an embodiment, step (v) is performed by dissolving the interfacial cross-linking agent by simple mixing.

The process for the preparation of an emulsion of the invention comprising one or more hydrophilic active agents (c2) in the interfacial layer (IL) comprises:
performing steps (i), (ii), (iii) and (iv); and
optionally step (v) as defined above, and
(vi) contacting the emulsion obtained in step (iv) or alternatively step (v) with the hydrophilic active agent.

In an embodiment, step (vi) is performed under such reaction conditions which do not involve a destabilization of the emulsion. In an embodiment, step (vi) is performed at a temperature from 10 to 60° C. at pH from 2 and 12.

The fourth aspect of the invention relates to the use of the oil-in-water emulsion according to the third aspect of the invention, which do not comprise active agents as a carrier; particularly to drug (pharmaceutical active ingredient) delivery system. As it is demonstrated in the experimental section, the oil-in-water emulsion of the present invention can comprises one or more active ingredients, which can also be delivered from the emulsion in a controlled/modified way by the esterase enzyme response.

The fifth aspect of the invention relates to the uses of the oil-in-water emulsion according to the third aspect of the invention.

It is part of the invention, a pharmaceutical emulsion as defined in the present application for use in therapy.

It is part of the invention, the use of a cosmetic emulsion as defined in the present application for the skin or hair care. In an embodiment, the cosmetic emulsion of the present invention is used for the skin and hair care, where the skin or hair care comprises ameliorating at least one of the following symptoms: roughness, flakiness, dehydration, tightness, chapping, and lack of elasticity.

It is part of the invention, the diagnostic emulsion as defined in the present application for use in diagnosis. In an embodiment, the diagnostic emulsion is a diagnostic imaging emulsion for use as imaging agent.

In an embodiment, the diagnostic emulsion is used as an imaging agent in detection assays. An appropriate detection assay can comprise: (a) putting into contact diagnostic emulsion of the invention having an diagnostic active agent, which is capable of specifically binding to a target agent with the target agent present in a sample to be tested for an appropriate period of time that allows the binding; and optionally (b) identifying and/or quantifying the target agent. Suitable test samples for the present invention can be serum, plasma, urine, and cephaloraquideum liquid. In a particular embodiment the identification and/or quantification of the target agent is carried out by methods well known in the art. Suitable methods for identification and/or quantification can be fluorescence, surface plasmon resonance, positron electron tomography, single photon emission computed tomography and colorimetry.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Materials

Dextran from Leuconostoc spp. (DXT-40, Mr~40 kDa), glycidyl methacrylate (GMA) (97%), dimethyl sulfoxide (DMSO) (98%), 3-mercaptopropionic acid (≥99%), acryloyl chloride (99%) and 2,2'-(ethylenedioxy)diethanethiol [3,6-dioxa-1,8-octane-dithiol (DODT)] (95%) were purchased from Aldrich and used as received. Phosphate-buffered saline (PBS) and dichloromethane was purchased from Scharlab and used as received. 4-(Dimethylamino)pyridine (DMAP) was purchased from Acros-Organics. Water ($H_2O$) used in the syntheses, unless otherwise stated, was deionized water from a MilliQ A10 Gradient equipment (Millipore). DHA rich oil (>95 wt %) extracted from fish oil was kindly provided by SENDABIO S.L. Hyaluronic acid (50,000 g $mol^{-1}$) was provided by Evonik and Hyaluronic acid (2.28× $10^6$ g $mol^{-1}$) was provided by Contipro. Low viscosity Chitosan from shrimp shells was acquired from Sigma Aldrich.

Characterization Methods

Dynamic Light Scattering (DLS): DLS analyses were conducted using a Zetasizer Nano ZS, ZEN3600 Model (Malvern Instruments Ltd). All measurements were performed in disposable sizing cuvettes at a laser wavelength of 633 nm and a scattering angle of 173°, while the zeta-potential measurements were performed in disposable zeta potential cells (pH 7.4, 25° C.). Before the measurement, DXT functionalized samples were dispersed in saline solution (0.9 wt % NaCl for size measurements and 1 mM NaCl for zeta-potential measurements) at a concentration of 1 mg/mL. Emulsion samples were dispersed in deionized water at a concentration of 2 mg oil/mL. Each measurement was repeated for three runs per sample at 25° C. Hyaluronic functionalized emulsions were dispersed in deionized water at a concentration of 2 mg oil/mL Nuclear magnetic resonance ($^1$H NMR): NMR spectra were recorded on a Bruker AVANCE III spectrometer at 500 MHz and 25° C. Chemical shifts (δ) are given in ppm relative to the residual signal of the solvent. Splitting patterns: b, broad; s, singlet; d, doublet; t, triplet; q, quartet; m, multiplet.

Laser diffraction (LD): LD analyses were conducted using Mastersizer 3000 laser diffraction system (Malvern Instruments Ltd). All measurements were performed at a laser wavelength of 430 nm using 600 mL of deionized water in a glass beaker. Each measurement was repeated for five runs per sample and 5 seconds per run at 25° C. following Mie dispersion model.

Transmission Electron Microscopy (TEM): TEM analyses were performed in a TECNAI G2 20 TWIN microscope (FEI, Eindhoven, The Netherlands), operating at an accelerating voltage of 200 KeV in a bright-field image mode. One drop of the sample dispersion in water (~3 μL, 0.035 mg/mL) was deposited on a carbon film supported on a copper grid (300 mesh), hydrophilized by a glow discharge process just prior to use. After staining for 20 seconds with a uranyl acetate aqueous solution (1% w/v), the sample was rotated at high speed in order to dry at room temperature quickly by spinning process. Number-average diameter was calculated by ImageJ platform analysis using a Gaussian curve fitting after counting about 300 nanoparticles.

Determination of the degree of substitution (DS expressed as percent of modified repeating unit, via one of its hydroxyl group, of the polysaccharide): For methacrylate or acrylate modified DXT and dextran SCPN methacrylate or acrylate, DS was calculated by $^1$H NMR through integration of the proton signal of the double bond of the methacrylate or acrylate (integration reference 1.0) with respect to the signals at 3.3-4.2 ppm corresponding to the protons of the glucose (Glc) moiety (6H for unsubstituted Glc and 5H for substituted Glc) except the anomeric protons and the substituted positions (mainly position 3). For the acrylate modified HA, the DS was calculated by $^1$H NMR through integration of the methyl group of HA (integration reference 3.0 at 2.2 ppm) with respect to the acrylate proton signals at 5.4-6.6 ppm. For methacrylate modified CHI, the DS was calculated by $^1$H NMR through integration of the proton signals from the double bond with respect to the broad signal at 2.8-3.2 ppm (integration reference 200) corresponding to the protons of the hydroxyl pendant group (—CH—$CH_2$—O—) group.

Surface Tension (ST): Surface tension measurements were performed in KSV Sigma 700 Force tensiometer by Ring Method using a Standard Ring (R-ring=9.58 mm, R-wire=0.185 mm). Automatic measurements of the "critical micellar concentration (CMC)" were performed by solving 1 g of DXT-poly-MA in 200 mL of water reaching the concentration of 2.5 g/L (final concentration) for the automatic addition. After each addition sample was stirred for 60 seconds and kept in rest during 120 seconds. Description of the experimental setup: Standard Vessel (diameter=66 mm, max. volume=110 mL), heavy phase (water) and light phase (air). Individual surface tension measurements were performed using "Surface Tension" program at the concentration of 5 g/L. Each sample was measured without stirring until surface tension stabilization (stabilization criteria: 4 runs repeating the first decimal digit). Description of the experimental setup: Small Vessel (diameter=50 mm, max. volume=70 mL), heavy phase (water) and light phase (air). The accuracy of the Du Noüy ring method is about 0.1 mN/m (cf. Table 2 page 3159 of J. Drelich et al. "Measurement of interfacial tension in fluid-fluid systems", Encyclopaedia of Surface and colloid Science, 2002, page 3152-3166).

Digital picture acquisition: for each dextran or hyaluronic polymer was dissolved in water at the concentration of 5 g/L and mixtures were shaken vigorously during 20 seconds and keeping in rest for another 10 additional seconds before digital picture acquisition.

Example 1. Synthesis of Methacrylate-Based Dextran Polymer Having DS=1-70% (DXT-Poly-MA)

Dextran (DXT-40, 1 g) was dissolved in 30 mL of dimethyl sulfoxide (DMSO) under a nitrogen atmosphere, to this solution 200 mg of 4-(N,N-dimethylamino)pyridine (DMAP, 1.6 mmol) was added. Then, 1 mL of glycidyl methacrylate (GMA, 1.2 mmol) was added and the mixture was stirred at room temperature until reaching the appropriate substitution degree (DS, percent of modified hydroxyl groups per repeating unit). Time required for each DS is summarized in Table 1 and other DS can be obtained following the kinetic curve described in FIG. 1. The reaction was stopped by adding an equimolar amount of concentrated HCl solution (37% v/v, 1.6 mmol, 0.132 mL) to neutralize DMAP. The modified dextran solution was purified by dialysis against distilled water (MWCO 3,500 Da) at room temperature until reaching deionized water conductivity values<1 µS (9 days, refreshing with 4 L of deionized water twice per day).

TABLE 1

Summary of the reaction time needed to reach a certain percentage of substitution (DS) and surface tension (ST) of an aqueous solution of DXT-poly-MA at 0.5 g/L.

| Name | DS (%) * | ST (mN/m) | Time (hours) |
|---|---|---|---|
| Comp. D0 (un-modified DXT) | 0 | 68.02 | |
| Comp. D2 | 8 | 65.62 | 7 |
| D3 | 10 | 58.53 | 15 |
| D4 | 13 | N/A | 16 |
| D5 | 15 | 58.61 | 16 |
| D6 | 19 | N/A | 16 |
| D7 | 24 | N/A | 16 |
| D8 | 28 | N/A | 24 |
| D9 | 36 | 54.02 | 31 |
| D10 | 45 | N/A | 48 |
| D11 | 50 | 46.82 | 55 |
| D12 | 52 | N/A | 66 |
| D13 | 55 | 44.30 | 72 |
| D14 | 70 | N/A | 104 |

* DS variability for early reaction times 10 < hours < 30 is ±5%; "N/A": data not available.

Example 2. Synthesis of Single-Chain Dextran Methacrylate-Based Nanoparticle D15 (DXT-SCNP-MA)

In a standard procedure, 0.37 mL of a previously prepared 0.15 M solution (2 mL, MeOH/PBS, 1:1, v/v, pH=9.5) of cross-linker DODT (0.06 mmol, 49 µL) was added dropwise using a syringe pump (0.04 mL/h) over a 0.02 M solution of DXT-Poly-MA (D12) (100 mg, 0.024 mmol, 13 mL PBS, pH=9.5) during 8 h at room temperature and under stirring. After addition, the reaction was maintained stirred at room temperature for 12 h. Further characterization studies were carried out after purification of 5 mL sample from the reaction mixture by dialysis against distilled water (MWCO 3,500 Da) until reaching deionized water conductivity values<1 µS (5 days, refreshing with 4 L of deionized water twice per day). Finally, the resulting aqueous solution was freeze-dried to obtain D15 as a white solid. Yield>90%. $^1$H NMR (500 MHz, D2O) δ ppm: 6.34-6.12 (m, 1H, methacrylic-CH), 5.94-5.70 (m, 1H, methacrylic-CH), 5.55-4.85 (5.5H, including H-1 and H-2/3 MA-substituted), 4.34-3.28 (28H, m, rest of Glc and 2×CH$_2$O of cross-linker), 3.06-2.53 (5H, m, CH(CH$_3$)CH$_2$S, CH$_2$S of cross-linker), 1.98 (s, 3H, methacrylic-CH$_3$), 1.29 (s, 3H, cross-linker-CH$_3$). Dh (DLS)=13±8 nm; PDI 0.2.

Example 3. Synthesis of Comparative Single-Chain Dextran Based Nanoparticle D16 by Functionalization of DXT-SCPN-MA of the Present Invention with 3-Mercaptopropionic Acid (DXT-SCPN-F)

In a standard procedure, 2 mL of an aqueous solution of 3-mercaptopropionic acid adding slowly 2 mL (61.4 µL, 7.5 µmol, pH=9.5) was slowly added to the reaction flask in the previously reported synthesis of the DXT-SCPN-MA D15. The reaction was stirred for 24 h and the excess acid was removed by dialysis against distilled water (MWCO 3,500 Da) until reaching deionized water conductivity values<1 µS (5 days, refreshing with 4 L of deionized water twice per day). The resulting aqueous solution was freeze-dried to obtain comparative DXT-SCPN-F D16 as a white solid. Yield>90%. $^1$H NMR (500 MHz, D$_2$O) δ ppm: 5.45-4.90 (6H, including H-1 and H-2/3 MA-substituted), 4.13-3.41 (31H, m, rest of Glc and 2×CH$_2$O of cross-linker), 3.02-2.71 (8H, m, 2×CH(CH$_3$)CH$_2$S, CH$_2$S of cross-linker and MPA), 2.70-2.49 (2H, m, CH$_2$COOH of MPA), 1.29 (s, 5.4H, cross-linker- and MPA-CH$_3$) Mw (GPC)=38 KDa, Mw/Mn=1.7; Dh (DLS)=15±4 nm; PDI 0.2, Zeta potential (pH=7.2, 25° C.)=−20 mV±5. TEM (uranyl acetate staining): 13±3 nm.

Example 4. Synthesis of Comparative Dextran Polymer D17 by Functionalization of DXT-Poly-MA of the Present Invention with 3-Mercaptopropionic Acid (DXT-Poly-F)

In a standard procedure, an aqueous solution of 3-mercaptopropionic acid (430 µL, 5 mL H$_2$O, pH=9.5) was slowly added to the previously prepared solution of DXT-poly-MA D12 (350 mg, 20 mL H$_2$O, pH=9.5). The reaction was maintained under constant stirring for 12 h and then purified by dialysis against distilled water (MWCO 3,500 Da). The resulting aqueous solution was freeze-dried to obtain the resulting quenched comparative polymer DXT-poly-F D17 as a white solid. Mw (GPC)=47 KDa, Mw/Mn=1.7. Zeta potential (pH=7.2)=−12 mV±7.

Example 5. Synthesis of O/W Emulsions Based on Methacrylate Dextran Polymer and Methacrylate Modified Dextran Nanoparticles Method M1: DXT-R (DXT-poly-MA, DXT-SCNP-MA, DXT-poly-F and DXT-SCNP-F) (z mg, Z % wt. based on the oil phase) was dissolved in deionized water (x g, X % wt., aqueous phase) in an 8 mL glass vial, to this solution an oil (y g, Y % wt.), were added raising 2 g of total mass. Then, emulsion was formed using an UP400S (Hielscher) system at 100% of amplitude and pulse during 4 minutes (400 W) with a H3 sonotrode tip (3 mm diameter, 100 mm length). Sonication step was carried out at 0° C., using an ice bath, and without stirring. Following this procedure M1 the emulsions thus obtained were disclosed in Table 2.

Method M2: DXT-poly-MA or DXT-SCNP-MA (20 mg, 5% wt. based on the oil phase) was dissolved in 3.6 mL of deionized water (aqueous phase, 90% wt.) in an 8 mL glass vial, to this solution 0.4 g of oil phase (10% wt.) were added. Then, emulsion was formed using an UP400S (Hielscher) system at 100% of amplitude and pulse during 4 minutes (400 W) with a H3 sonotrode tip (3 mm diameter, 100 mm length). Sonication step was carried out at 0° C., using an ice bath, and under magnetic stirring. Following this procedure M2 the emulsions thus obtained were disclosed in Table 2.

Table 2. Experimental conditions for emulsion formation and their characterization following the methods M1 and M2. Weight percentages (% wt.) are based on the whole emulsion except in the case of the stabilizer, (*): % wt. based on the oil phase. Size distribution values in Intensity (DLS: Dynamic Light Scattering) and Volume (LD: Laser Diffraction). "N/A": data not available.

TABLE 2

| Name | Oil phase(x, X) Class | % wt. | mass (g) | Water (y, Y) % wt. | mass (g) | Stabilizer (z, Z) Type | % wt.* | mass (mg) | Method |
|---|---|---|---|---|---|---|---|---|---|
| Comp. E0 | Dodecane | 50 | 1 | 50 | 1 | Comp. D0[(1)] | 1 | 10 | M1 |
| E1 | Dodecane | 50 | 1 | 50 | 1 | D12 | 1 | 10 | M1 |
| Comp. E2 | Dodecane | 50 | 1 | 50 | 1 | Comp. D17 | 1 | 10 | M1 |
| E3 | Dodecane | 50 | 1 | 50 | 1 | D15 | 1 | 10 | M1 |
| Comp. E4 | Dodecane | 50 | 1 | 50 | 1 | Comp. D16 | 1 | 10 | M1 |
| Comp. E5 | Olive | 50 | 1 | 50 | 1 | Comp. D17 | 1 | 10 | M1 |
| Comp. E6 | Olive | 40 | 0.8 | 60 | 1.2 | Comp. D17 | 1 | 8 | M1 |
| Comp. E7 | Olive | 30 | 0.6 | 70 | 1.4 | Comp. D17 | 1 | 6 | M1 |
| Comp. E8 | Olive | 20 | 0.4 | 80 | 1.6 | Comp. D17 | 1 | 4 | M1 |
| Comp. E9 | Olive | 10 | 0.2 | 90 | 1.8 | Comp. D17 | 1 | 2 | M1 |
| Comp. E10 | Sunflower | 50 | 1 | 50 | 1 | Comp. D17 | 1 | 10 | M1 |
| Comp. E11 | Sunflower | 40 | 0.8 | 60 | 1.2 | Comp. D17 | 1 | 8 | M1 |
| Comp. E12 | Sunflower | 30 | 0.6 | 70 | 1.4 | Comp. D17 | 1 | 6 | M1 |
| Comp. E13 | Sunflower | 20 | 0.4 | 80 | 1.6 | Comp. D17 | 1 | 4 | M1 |
| Comp. E14 | Sunflower | 10 | 0.2 | 90 | 1.8 | Comp. D17 | 1 | 2 | M1 |
| Comp. E15 | Olive | 30 | 0.6 | 70 | 1.4 | Comp. D16 | 1 | 2 | M1 |
| Comp. E16 | Olive | 20 | 0.4 | 80 | 1.6 | Comp. D16 | 1 | 2 | M1 |
| Comp. E17 | Olive | 10 | 0.2 | 90 | 1.8 | Comp. D16 | 1 | 2 | M1 |
| Comp. E18 | Sunflower | 30 | 0.6 | 70 | 1.4 | Comp. D16 | 1 | 2 | M1 |
| Comp. E19 | Sunflower | 20 | 0.4 | 80 | 1.6 | Comp. D16 | 1 | 2 | M1 |
| Comp. E20 | Sunflower | 10 | 0.2 | 90 | 1.8 | Comp. D16 | 1 | 2 | M1 |
| Comp. E21 | Eucalyptus | 30 | 0.6 | 70 | 1.4 | Comp. D16 | 1 | 2 | M1 |
| Comp. E22 | Eucalyptus | 20 | 0.4 | 80 | 1.6 | Comp. D16 | 1 | 2 | M1 |
| Comp. E23 | Eucalyptus | 10 | 0.2 | 90 | 1.8 | Comp. D16 | 1 | 2 | M1 |
| E24 | Olive | 30 | 0.6 | 70 | 1.4 | D15 | 1 | 2 | M1 |
| E25 | Olive | 20 | 0.4 | 80 | 1.6 | D15 | 1 | 2 | M1 |
| E26 | Olive | 10 | 0.2 | 90 | 1.8 | D15 | 1 | 2 | M1 |
| E27 | Sunflower | 30 | 0.6 | 70 | 1.4 | D15 | 1 | 2 | M1 |
| E28 | Sunflower | 20 | 0.4 | 80 | 1.6 | D15 | 1 | 2 | M1 |
| E29 | Sunflower | 10 | 0.2 | 90 | 1.8 | D15 | 1 | 2 | M1 |
| E30 | Peppermint | 30 | 0.6 | 70 | 1.4 | D15 | 1 | 2 | M1 |
| E31 | Peppermint | 20 | 0.4 | 80 | 1.6 | D15 | 1 | 2 | M1 |
| E32 | Peppermint | 10 | 0.2 | 90 | 1.8 | D15 | 1 | 2 | M1 |
| E33 | Eucalyptus | 30 | 0.6 | 70 | 1.4 | D15 | 1 | 2 | M1 |
| E34 | Eucalyptus | 20 | 0.4 | 80 | 1.6 | D15 | 1 | 2 | M1 |
| E35 | Eucalyptus | 10 | 0.2 | 90 | 1.8 | D15 | 1 | 2 | M1 |
| Comp. E36 | Olive | 10 | 0.2 | 90 | 1.8 | Comp. D17 | 1 | 2 | M1 |
| E37 | Olive | 10 | 0.2 | 90 | 1.8 | D12 | 1 | 2 | M1 |
| Comp. E38 | Olive | 10 | 0.2 | 90 | 1.8 | Comp. D16 | 1 | 2 | M1 |
| E39 | Olive | 10 | 0.2 | 90 | 1.8 | D15 | 1 | 2 | M1 |
| Comp. E40 | Olive | 10 | 0.2 | 90 | 1.8 | Comp. D17 | 2 | 4 | M1 |
| E41 | Olive | 10 | 0.2 | 90 | 1.8 | D12 | 2 | 4 | M1 |
| Comp. E42 | Olive | 10 | 0.2 | 90 | 1.8 | Comp. D16 | 2 | 4 | M1 |
| E43 | Olive | 10 | 0.2 | 90 | 1.8 | D15 | 2 | 4 | M1 |
| Comp. E44 | Olive | 10 | 0.2 | 90 | 1.8 | Comp. D17 | 5 | 10 | M1 |
| E45 | Olive | 10 | 0.2 | 90 | 1.8 | D12 | 5 | 10 | M1 |
| Comp. E46 | Olive | 10 | 0.2 | 90 | 1.8 | Comp. D16 | 5 | 10 | M1 |
| E47 | Olive | 10 | 0.2 | 90 | 1.8 | D15 | 5 | 10 | M1 |
| Comp. E48 | Sunflower | 10 | 0.2 | 90 | 1.8 | Comp. D17 | 1 | 2 | M1 |
| E49 | Sunflower | 10 | 0.2 | 90 | 1.8 | D12 | 1 | 2 | M1 |
| Comp. E50 | Sunflower | 10 | 0.2 | 90 | 1.8 | Comp. D16 | 1 | 2 | M1 |
| E51 | Sunflower | 10 | 0.2 | 90 | 1.8 | D15 | 1 | 2 | M1 |
| Comp. E52 | Sunflower | 10 | 0.2 | 90 | 1.8 | Comp. D17 | 2 | 4 | M1 |
| E53 | Sunflower | 10 | 0.2 | 90 | 1.8 | D12 | 2 | 4 | M1 |
| Comp. E54 | Sunflower | 10 | 0.2 | 90 | 1.8 | Comp. D16 | 2 | 4 | M1 |
| E55 | Sunflower | 10 | 0.2 | 90 | 1.8 | D15 | 2 | 4 | M1 |
| Comp. E56 | Sunflower | 10 | 0.2 | 90 | 1.8 | Comp. D17 | 5 | 10 | M1 |
| E57 | Sunflower | 10 | 0.2 | 90 | 1.8 | D12 | 5 | 10 | M1 |
| Comp. E58 | Sunflower | 10 | 0.2 | 90 | 1.8 | Comp. D16 | 5 | 10 | M1 |
| E59 | Sunflower | 10 | 0.2 | 90 | 1.8 | D15 | 5 | 10 | M1 |
| E60 | Fish | 10 | 0.2 | 90 | 1.8 | D12 | 1 | 2 | M1 |
| E61 | Fish | 10 | 0.2 | 90 | 1.8 | D12 | 2 | 4 | M1 |

TABLE 2-continued

| Name | | | | | | | | | |
|---|---|---|---|---|---|---|---|---|---|
| E62 | Fish | 10 | 0.2 | 90 | 1.8 | D12 | 5 | 10 | M1 |
| E63 | Fish | 10 | 0.4 | 90 | 3.6 | D1 | 5 | 20 | M2 |
| Comp. E64 | Fish | 10 | 0.4 | 90 | 3.6 | Comp. D2 | 5 | 20 | M2 |
| E65 | Fish | 10 | 0.4 | 90 | 3.6 | D5 | 5 | 20 | M2 |
| E66 | Fish | 10 | 0.4 | 90 | 3.6 | D6 | 5 | 20 | M2 |
| E67 | Fish | 10 | 0.4 | 90 | 3.6 | D8 | 5 | 20 | M2 |
| E68 | Fish | 10 | 0.4 | 90 | 3.6 | D9 | 5 | 20 | M2 |
| E69 | Fish | 10 | 0.4 | 90 | 3.6 | D11 | 5 | 20 | M2 |
| E70 | Sunflower | 10 | 0.4 | 90 | 3.6 | D4 | 5 | 20 | M2 |
| E71 | Sunflower | 10 | 0.4 | 90 | 3.6 | D9 | 5 | 20 | M2 |
| E72 | Sunflower | 10 | 0.4 | 90 | 3.6 | D11 | 5 | 20 | M2 |
| E73 | Sunflower | 10 | 0.4 | 90 | 3.6 | D14 | 5 | 20 | M2 |
| E74 | Fish | 10 | 0.4 | 90 | 3.6 | D7 | 5 | 20 | M2 |
| E75 | Fish | 10 | 0.4 | 90 | 3.6 | D7 | 5 | 20 | M2 |
| E81 | Fish | 10 | 0.4 | 90 | 3.6 | D7 | 5 | 20 | M1 |
| E83 | Sunflower | 10 | 0.4 | 90 | 3.6 | D7 | 5 | 20 | M2 |
| E88 | Sunflower | 10 | 0.4 | 90 | 3.6 | D7 | 5 | 20 | M2 |
| E89 | Sunflower | 10 | 0.4 | 90 | 3.6 | D7 | 5 | 20 | M2 |
| E90 | Sunflower | 40 | 0.8 | 60 | 1.2 | D15 | 5 | 40 | M1 |
| E92 | Fish | 10 | 0.4 | 90 | 3.6 | D7 | 5 | 20 | M2 |

| | DLS characterization | | LD characterization | |
|---|---|---|---|---|
| Name | Z-Average (d · nm) | PDI | Volume-average (d · μm) | Uniformity |
| Comp. E0 | N/A | N/A | N/A | N/A |
| E1 | 3100 | 0.31 | 7.3 | 2.56 |
| Comp. E2 | 2070 | 0.14 | 14.2 | 1.8 |
| E3 | 1740 | 0.33 | 6.4 | 0.75 |
| Comp. E4 | 1640 | 0.53 | 19.2 | 1.4 |
| Comp. E5 | 1470 | 0.78 | 50.8 | 6.8 |
| Comp. E6 | 390 | 0.45 | 17.7 | 2.7 |
| Comp. E7 | 340 | 0.65 | 75.2 | 4.6 |
| Comp. E8 | 430 | 0.73 | 17.0 | 5.8 |
| Comp. E9 | 300 | 0.45 | 11.9 | 1.3 |
| Comp. | 960 | 0.63 | 45.5 | 7.2 |
| Comp. E11 | 540 | 0.69 | 65.2 | 16.7 |
| Comp. E12 | 330 | 0.50 | 6.1 | 1.0 |
| Comp. E13 | 350 | 0.87 | 3.4 | 5.4 |
| Comp. E14 | 410 | 0.48 | 7.6 | 3.5 |
| Comp. E15 | 300 | 0.66 | 19.4 | 0.6 |
| Comp. E16 | 410 | 0.74 | 55.4 | 1.2 |
| Comp. E17 | 430 | 0.64 | 8.1 | 2.1 |
| Comp. E18 | 340 | 0.48 | 9.0 | 7.4 |
| Comp. E19 | 370 | 0.78 | 1.4 | 1.2 |
| Comp. | 480 | 0.65 | 2.5 | 1.2 |
| Comp. E21 | 193 | 0.69 | N/A | N/A |
| Comp. E22 | 1220 | 0.77 | N/A | N/A |
| Comp. E23 | 470 | 0.14 | N/A | N/A |
| E24 | 1430 | 0.88 | 17.8 | 4.7 |
| E25 | 1050 | 0.82 | 6.2 | 1.7 |
| E26 | 390 | 0.76 | 2.0 | 3.4 |
| E27 | 830 | 0.65 | 4.0 | 1.2 |
| E28 | 680 | 0.65 | 17.4 | 0.7 |
| E29 | 380 | 0.69 | 1.6 | 2.3 |
| E30 | 3180 | 0.33 | N/A | N/A |
| E31 | 1160 | 0.49 | N/A | N/A |
| E32 | 400 | 0.34 | N/A | N/A |
| E33 | 1420 | 0.34 | N/A | N/A |
| E34 | 990 | 0.32 | N/A | N/A |
| E35 | 600 | 0.21 | N/A | N/A |
| Comp. E36 | 300 | 0.45 | 11.9 | 1.3 |
| E37 | 860 | 0.69 | 3.2 | 0.8 |
| Comp. E38 | 430 | 0.73 | 8.1 | 2.1 |
| E39 | 190 | 0.62 | 2.0 | 3.4 |
| Comp. E40 | 270 | 0.57 | 2.5 | 3.3 |
| E41 | 1400 | 0.44 | 1.5 | 0.5 |
| Comp. E42 | 1050 | 0.79 | 3.4 | 0.8 |
| E43 | 770 | 0.68 | 3.8 | 0.9 |
| Comp. E44 | 300 | 0.42 | 2.3 | 2.1 |
| E45 | 460 | 0.50 | 1.0 | 0.7 |
| Comp. E46 | 530 | 0.50 | 0.9 | 1.3 |
| E47 | 1180 | 0.72 | 4.3 | 0.8 |
| Comp. E48 | 410 | 0.48 | 7.6 | 3.5 |
| E49 | 840 | 0.77 | 2.8 | 0.7 |
| Comp. E50 | 480 | 0.78 | 2.5 | 1.2 |
| E51 | 380 | 0.63 | 1.6 | 2.3 |
| Comp. E52 | 310 | 0.46 | 14.2 | 6.8 |
| E53 | 510 | 0.54 | 1.3 | 0.6 |

TABLE 2-continued

| | | | | |
|---|---|---|---|---|
| Comp. E54 | 370 | 0.61 | 1.9 | 1.0 |
| E55 | 530 | 0.56 | 9.8 | 2.7 |
| Comp. E56 | 220 | 0.34 | 5.6 | 4.6 |
| E57 | 380 | 0.42 | 1 | 0.6 |
| Comp. E58 | 310 | 0.46 | 1.5 | 0.9 |
| E59 | 1620 | 0.52 | 1.9 | 1.3 |
| E60 | 530 | 0.58 | 1.4 | 0.8 |
| E61 | 420 | 0.44 | 1.1 | 0.7 |
| E62 | 460 | 0.46 | 0.8 | 0.7 |
| E63 | 700 | 0.54 | 1.9 | 0.6 |
| Comp. E64 | 250 | 0.25 | 0.8 | 1.6 |
| E65 | 280 | 0.22 | 0.6 | 0.7 |
| E66 | 340 | 0.36 | 1.1 | 2.7 |
| E67 | 460 | 0.42 | 0.5 | 0.7 |
| E68 | 550 | 0.38 | 0.6 | 0.6 |
| E69 | 420 | 0.44 | 0.8 | 0.7 |
| E70 | N/A | N/A | 0.99 | 2.0 |
| E71 | N/A | N/A | 0.82 | 0.5 |
| E72 | N/A | N/A | 0.97 | 0.6 |
| E73 | N/A | N/A | 1.21 | 0.6 |
| E74 | 305 | 0.27 | 0.38 | 0.5 |
| E75 | N/A | N/A | 0.43 | 0.6 |
| E81 | 300 | 0.24 | 0.55 | 0.5 |
| E83 | 290 | 0.3 | N/A | N/A |
| E88 | 320 | 0.35 | N/A | N/A |
| E89 | 370 | 0.32 | N/A | N/A |
| E90 | 1090 | 0.62 | 1.72 | 1.32 |
| E92 | N/A | N/A | 0.51 | 0.51 |

[1]Comp. D0 = unmodified commercial dextran

Example 6. Synthesis of Interfacial Crosslinked O/W Emulsions Based on Methacrylate Dextran Polymer and Methacrylate Dextran Nanoparticles Method M3: DXT-poly-MA or DXT-SCPN-MA can be successfully crosslinked at the O/W interface. Different crosslinker (DODT) amounts, from 0.25 to 1.5 thiol equivalents related to methacrylate groups present in the polymer or nanoparticle, can be used to this purpose as defined above in Table 3.

TABLE 3

Reaction conditions for different amounts of interfacial crosslinker (DODT), their thiol (SH) molar equivalents related to the number of MA groups presented in DXT-poly-MA (D7 from Table 1) (DS ~24%) and the volume of NaOH (1M) required to reach pH = 9 in each case.

| Emulsion | DXT-poly-MA | SH eq. | DODT (μL) | NaOH 1M (μL) |
|---|---|---|---|---|
| E75 [1] | D7 | 0 | 0 | 1 |
| E76 | D7 | 0.25 | 0.5 | 2 |
| E77 | D7 | 0.50 | 1.0 | 3 |
| E78 | D7 | 0.75 | 1.5 | 5 |
| E79 | D7 | 1 | 2.0 | 8 |
| E80 | D7 | 1.5 | 3.0 | 11 |

[1] E75 is an interface non-crosslinked emulsion of the present invention

Here, a crosslinked emulsion (E77) based on DXT-poly-MA (D7) with 0.5 thiol (—SH) equivalents is described as example. D7 (20 mg, 5% wt. related to oil phase) was dissolved in 3.6 mL of deionized water (aqueous phase, 90% wt.) in a 8 mL glass vial, to this solution 0.4 g of fish oil (oil phase, 10% wt.) were added. Then, 1 μL DODT (0.5 SH eq.) was carefully added over the oil phase and the volume of NaOH (1M) up to pH=9 (required for fast thio-michael addition, hence cross-linking at the interface) was added inside the aqueous phase, and quickly moved on to the sonication step, avoiding basic hydrolysis of the ester groups presented in D7. Emulsion E77 was formed using an UP400S (Hielscher) system at 100% of amplitude and pulse during 4 minutes (400 W) with a H3 sonotrode tip (3 mm diameter, 100 mm length). Sonication step was carried out at 0° C., using an ice bath, and under magnetic stirring.

Emulsions E76, E78, E79 and E80 were analogously prepared following the process as disclosed for emulsion E77 but using the equivalents of SH, thus the amount of crosslinker and NaOH disclosed in Table 3. As a comparative interface non-crosslinked emulsion for control experiment, E75 was also prepared wherein no amount of crosslinker was added.

Successful cross-linking was assessed by a DMSO/Dioxane (70:30, v/v) challenge, whereby 1.5 mL of each crosslinked emulsion was diluted in 30 mL (Dil. 1:20) of the previous DMSO/dioxane solution (which is a solvent for both phases, aqueous and oil). As example, emulsion with 0.5 thiol equivalents (E77) was dissolved overnight, at room temperature and under magnetic stirring. Then, oil phase was removed after liquid-liquid extraction with hexane (3×80 mL). Aqueous phase (DMSO, water and D7) was collected and purified by Dialysis against distilled water (MWCO 3,500 Da) during 4 days, refreshing with 4 L of deionized water twice per day). The resulting aqueous solution was freeze-dried to obtain the crosslinked polymer (D7-CL) as a white solid. Oil traces were removed via solid-liquid extraction with hexane. D7-CL was immersed in 1 mL of hexane and triturated using a vortex. After 3 centrifugation cycles (14,000 rpm, 5 min, Minispin), whereby solid dextran was centrifuged and the supernatant was removed, the resulting D7-CL polymer was obtained.

The new degree of substitution was calculated as described in the synthesis of methacrylated dextran and the degree of crosslinking by integrating the peaks between 3.06-2.58 relative to the linker DODT. $^1$H NMR (500 MHz, $D_2O$) δ ppm: 6.38-6.08 (m, 1H, methacrylic-CH), 5.95-5.67 (m, 1H, methacrylic-CH), 5.55-4.85 (8.2H, including H-1 and H-2/3 MA-substituted), 4.38-3.25 (40H, m, rest of Glc and 2×$CH_2O$ of cross-linker), 3.06-2.58 (3.3H, m, $CH(CH_3)$ $CH_2S$, $CH_2S$ of cross-linker), 1.98 (s, 3.7H, methacrylic-$CH_3$), 1.36-1.12 (b, 1.7H, cross-linker-$CH_3$).

TABLE 4

$^1$H NMR(D$_2$O, 500 MHz) of emulsions based on D7 (DS = 24% before crosslinking at the O/W interface) after crosslinking with different thiol equivalents of DODT linker (0-1.5 eq. SH) based on the number of MA groups assuming that all the diblock copolymer is located at the oil/water interface.

| Emulsions based on D7 | E75 (0 eq.) | E76 (0.25 eq.) | E77 (0.5 eq.) | E78 (0.75 eq.) | E79 (1 eq.) | E80 (1.5 eq.) |
|---|---|---|---|---|---|---|
| DS (Glc unmodified) | 79 | 75 | 75 | 80 | 76 | 73 |
| DS (Glc-MA) | 21 | 19 | 16 | 8 | 7 | 6 |
| DS (Glc-DODT) | 0 | 6 | 9 | 12 | 17 | 21 |
| DS Final (Glc-MA + Glc-DODT) | 21 | 25 | 25 | 20 | 24 | 27 |
| % initial MA reacted | 0 | 25 | 39 | 60 | 72 | 88 |

The interfacial crosslinked O/W emulsions of the present invention prepared following Method M3 are disclosed below in Table 5.

Table 5. Experimental conditions for emulsion formation and their characterization. Weight percentages (% wt.) are based on the whole emulsion except in the case of the stabilizer, (*): % wt. based on the oil phase. Size distribution values in Intensity (DLS: Dynamic Light Scattering) and Volume (LD: Laser Diffraction). "N/A": data not available.

TABLE 5

| | | Oil phase(x, X) | | Water (y, Y) | | Stabilizer (z, Z) | | |
|---|---|---|---|---|---|---|---|---|
| Name | Class | % wt. | mass (g) | % wt. | mass (g) | Type | % wt.* | mass (mg) |
| E76 | Fish | 10 | 0.4 | 90 | 3.6 | D7 | 5 | 20 |
| E77 | Fish | 10 | 0.4 | 90 | 3.6 | D7 | 5 | 20 |
| E78 | Fish | 10 | 0.4 | 90 | 3.6 | D7 | 5 | 20 |
| E79 | Fish | 10 | 0.4 | 90 | 3.6 | D7 | 5 | 20 |
| E80 | Fish | 10 | 0.4 | 90 | 3.6 | D7 | 5 | 20 |
| E82 | Fish | 10 | 0.4 | 90 | 3.6 | D7 | 5 | 20 |
| E84 | Sunflower | 10 | 0.4 | 90 | 3.6 | D7 | 5 | 20 |
| E85 | Fish | 10 | 0.4 | 90 | 3.6 | D7 | 5 | 20 |
| E86 | Fish | 10 | 0.4 | 90 | 3.6 | D7 | 5 | 20 |
| E87 | Fish | 10 | 0.4 | 90 | 3.6 | D7 | 5 | 20 |
| E91 | Fish | 10 | 0.4 | 90 | 3.6 | D7 | 5 | 20 |

| | DLS characterization | | LD characterization | |
|---|---|---|---|---|
| Name | Z-Average (d · nm) | PDI | Volume-average (d · μm) | Uniformity |
| E76 | N/A | N/A | 0.44 | 0.6 |
| E77 | N/A | N/A | 0.38 | 0.6 |
| E78 | N/A | N/A | 0.38 | 0.7 |
| E79 | N/A | N/A | 0.39 | 0.8 |
| E80 | N/A | N/A | 0.47 | 1.1 |
| E82 | 300 | 0.24 | 0.51 | 0.5 |
| E84 | 280 | 0.3 | N/A | N/A |
| E85 | 290 | 0.22 | 0.37 | 0.6 |
| E86 | 260 | 0.19 | 0.38 | 0.5 |
| E87 | 330 | 0.26 | 0.38 | 0.7 |
| E91 | N/A | N/A | 0.53 | 0.61 |

Example 7. Methacrylate-Modified Dextran Polymer Conjugate of Methacrylate Dextran Based Polymers and Nanoparticles Method Encapsulation of Lipophilic Active Agents Active agent was dissolved in the oil phase and stirred overnight until total dissolution. Compound solubility determines the maximum concentration at the dispersed phase (oil phase) which must be below saturation. Once the active agent is totally solved, the protocol for the production of non-interfacial crosslinked (o/w)-emulsions (M2) or interfacial crosslinked (o/w)-emulsions (M3) are carried out considering the final mass of the oil solution (Active agent-oil) as the mass of the oil phase. The encapsulation of o-carborane (C1) and 16α-fluoroestradiol (C2) as active agents (i.e. pharmaceutical active ingredients-API) and PERFECTA® as diagnostic agent for Magnetic Resonance Imaging (MRI) of Fluor are described in Table 7 as examples.

Surface Functionalization of Hydrophilic Active Agents

Once emulsion is produced, hydrophilic active agents such as targeting agent, which functional groups are susceptible to react with others present at the o/w interface, can react through the water continuous phase at mild conditions (pH: 4.5-13) preventing hydrolysis or colloidal destabilization. It consists in adding the hydrophilic active agent directly into the emulsion and the subsequent adjustment of the reaction conditions (pH, temperature and time). Purification is performed via Size Exclusion Chromatography (SEC) using a PD-10 column.

This process of surface functionalization can be performed by two different procedures depending on the type of starting material being used. On one hand, single Conjugation consists in the surface functionalization of a free-lipophilic-Active agent emulsion (C3, Table 7). On the other hand, double conjugation consists in the surface functionalization after the lipophilic active agent emulsion obtained in previous step of "Encapsulation of a lipophilic Active agents" (Examples C4 and C5 in Table 7).

It means that for a double conjugation, a first step comprising the encapsulation of the lipophilic Active agent is performed is performed followed by the surface functionalization with hydrophilic active agents.

Conjugates: Following the above disclosed method, the methacrylate-modified dextran polymer conjugate thus obtained were disclosed in Table 7.

Table 7. The emulsion, emulsifier, oil used for the preparation of the conjugates of the present invention, as well as the active ingredient and its position in the composition are herein below disclosed.

TABLE 7

| | | | | Active ingredient | |
|---|---|---|---|---|---|
| Name | Emulsion | Emulsifier | oil | Name | Position |
| C1 | E85 | D7 | Fish | o-carborane | Oil phase |
| C2 | E86 | D7 | Fish | 16α- | Oil phase |

TABLE 7-continued

| Name | Emulsion | Emulsifier | oil | Active ingredient Name | Position |
|---|---|---|---|---|---|
| C3 | E87 | D7 | Fish | fluoroestradiol (FES) DOTA/ $^{64}$Cu | Interface layer |
| C4 | E88 | D7 | Sunflower | PERFECTA ® DOTA/ Gd$^{3+}$ | Oil phase Interface layer |
| C5 | E89 | D7 | Sunflower | Nile red Fluorescein | Oil phase Interface layer |

Results

The conjugates disclosed above which contain the methacrylate modified DXT of the present invention are stable. In fact, the reaction conditions used for the surface functionalization of the droplet did not induce destabilization of the O/W emulsions.

On the other hand, the presence of the methacrylate group at the surface of the droplet, which can be further stabilised by the introduction of interfacial crosslinking, are useful as targeting delivery system. In particular, conjugate C3 was administered to healthy rats via intravenous and intratracheal, resulting in a longer retained time of the methacrylate modified DXT polymer (D7) of the invention in the lungs. This fact is advantageous because a more sustained release could be achieved reducing the number of intakes of the active ingredient and increasing the compliance of the treatment.

Example 8. Stability Tests of Methacrylate Dextran Based Polymers and Nanoparticles For the purpose of the invention, an emulsion is stable when no phase separation of the oil phase above the aqueous phase is observed by visual inspection independently of the increase in droplet size, meaning that the modified polysaccharide according to the present invention maintain the whole oil phase encapsulated and redispersed in water. On the other hand, the appearance of an oil layer above the aqueous phase or the presence of oil droplet at the surface of the aqueous phase indicates the lack of stability of the emulsion.

Therefore, for the purpose of the invention an emulsion is considered stable when phase separation is not observed for one month even if increase in droplet diameter is observed.
Crosslinking Assessment by PBS Challenge Medium stability studies were carried out by diluting (Dil. 1:2) the interfacial crosslinked O/W emulsions of the present invention (E76, E77, E78, E79 and E80) or the interface non-crosslinked O/W emulsion of the present invention (E75) with deionized water or phosphate buffered saline (PBS, 10 mM phosphate). All samples were stored at 4° C. in darkness for 48 h. Then, size distribution was measured by LD.
Long-Term Stability at Different Storing Conditions An interfacial crosslinked O/W emulsion of the present invention (E82) with 0.5 thiol equivalents and an interface non-crosslinked O/W emulsion of the present invention (E81) emulsion based on 10 wt. % of fish oil and 0.5 wt. % of DXT-poly-MA (D5) of the invention were performed by storing 1 mL of each at 4 different conditions (A: light at r.t., B: dark at r.t., C: dark at 5° C. and D: dark at 40° C.) during 3 months. Emulsion stability was subsequently evaluated by visual inspection, as well as determination of their hydrodynamic diameter by DLS and volume average diameter by LD at 3 different time points (1 month, 2 months and 3 months).

In particular, E81 demonstrates to be stable for 1 month; despite, an increase of size and subsequent creaming effect phenomena in all storage conditions, no phase separation was observed, confirming the stability of the emulsion. After 1 month, any storage condition was able to maintain emulsion stability where visual inspection and LD confirmed the presence of a colloidal system. At months 2 and 3 measurements are only performed on LD because the droplet size was too large to be measured by DLS, but no phase separation was observed. As conclusion, DS=15% can stabilize emulsions, for 1 month at least, despite a slight increase in droplet diameter. On the other hand, E82 which was stabilized with the same DXT-poly-MA (D5) have been demonstrated to be also stable for 3 months in all the storage conditions. Moreover, crosslinking at the o/w interface have proved to maintain unaltered size distribution in all storage conditions with the exception of "D" (dark at 40° C.). It is important to mention that fish oil is very sensitive to light and temperature which explains the presence of large droplet populations produced in condition "D" at increasing time. However, this is not happening at room temperature even in case "A", where room temperature is combined with light, until the third month. Altogether the results confirm the stability of the non-interfacial crosslinked and interface cross-linked emulsion of the present invention in different conditions with no change in droplet diameter for the latter one.
Long-Term Stability at Different Media Time stability studies were carried out on an example of non-interfacial crosslinked O/W emulsion of the present invention (E83) and interfacial crosslinked O/W emulsion of the present invention (E82) deionized water or phosphate buffered saline (PBS, 10 mM phosphate). All samples were stored at 4° C. in darkness for 48 h. Then, size distribution was measured by LD.
Results of the Stability Test On one hand, unmodified dextran polymer (DXT) did not show any interfacial activity as a clear phase separation. On the other hand, O/W type emulsion was obtained when DXT-poly-MA of the invention, DXT-SCPN-MA of the invention, comparative DXT-SCPN-F and comparative DXT-poly-F were used as stabilizer wherein the ST is equal to or lower than 60 mN/m. Actually, it is worth mentioning that it was quite surprising to observe that a decrease of only 10-12 mN/m compared to the surface tension of deionised water, was sufficient to confer interfacial activity to the modified dextran and offer the possibility to produce stable emulsions. In particular, the smaller droplet sizes were obtained when the emulsifier contained methacrylate groups (i.e. DXT-poly-MA and DXT-SCPN-MA) compared to large droplets when the functional group on the dextran derivative was a carboxylate anion (i.e. comparative DXT-SCPN-F and DXT-poly-F). Such difference could be explained by the hydrophobicity of the methacrylate group (which correlates with the ST values), increasing its affinity with the hydrophobic oil, compared to the hydrophilic carboxylate group. Thus, the creaming effect observed for DXT-poly-F and DXT-SCPN-F was in good agreement with the larger droplet size obtained. Finally, the interface cross-linked emulsions containing the MA-modified DXT of the present invention (DXT-poly-MA or DXT-SCPN-MA) allow the droplet diameter to be maintained with time compared to the non-interfacial crosslinked DXT-poly-MA or DXT-SCNP-MA), while both emulsion appeared to be stable as no phase separation occurred.

Example 9. Enzyme-Responsiveness Analysis of Methacrylate Dextran Based Polymers and Nanoparticles The emulsion E90 (containing the DXT-poly-MA D15 and sunflower oil) of the present invention was put in the presence of the following lipase enzymes that cleave ester bonds:
Candida Antarctica Lipase B (CALB)
Rhizomucor miehei lipase (RML)
Rhizopus oryzae Lipase (ROL)
By Visual Inspection Fractions of 100 μL of the emulsion E90 of the present invention were mixed with 100 μL of each one of the above-mentioned lipases (CALB, RML, ROL; 20 mg/mL) in an HPLC glass vials. Mixtures were kept resting for 40 hrs at room temperature before digital pictures acquisition.

As judged by visual inspection, the addition of CALB, RML and ROL enzymes affected the stability of the emulsion after 40 hrs with a clear creaming effect observed and the presence of an oil layer at the surface of the emulsion. On the other hand, after the same time the emulsion E90 of the present invention alone appeared stable.
By Laser Diffraction (LD)

Fractions of 100 μL of the emulsion E90 of the present invention were mixed with 100 μL of each one of the above-mentioned lipases (CALB, RML, ROL or TLL; 20 mg/mL) in an HPLC glass vials. Mixtures were kept resting for 40 hrs at room temperature.

The destabilisation of the emulsion E90 of the present invention in the presence of the lipases was monitored by laser diffraction for 16 hours. Thus, when CALB enzyme was added to the emulsion, the main droplet size population decreased with time while larger droplets appeared with the appearance of oil droplet at the surface of the water in the sample container, confirming the lack of stability of the emulsion in the presence of the CALB enzyme. This decrease of the intensity of the main population indicates the destruction of the oil droplet and that the enzyme provokes the hydrolysis of the methacrylate groups which result in the desorption of the polysaccharide from the interface and the demulsification of the system, thus confirming that the emulsions of the present invention is responsive to the presence of esterase enzymes. As control experiments, the emulsion E90 was also monitored during 16 hrs without the addition of enzyme. After that time, it was observed that the main droplet size population remained mostly constant during the 16 hrs experiments.

Similarly, enzyme responsiveness was also studied for E92 which is an interface non-crosslinked emulsion containing fish oil emulsion at 10 wt % stabilized with 0.5 wt % of DXT-poly-MA (D7) and the corresponding interfacial crosslinked emulsion E91.

Firstly, it is worth mentioning that both emulsions are stable without any enzyme.

Secondly, after the addition of CALB Lipase, a clear decrease of the main droplet size population was observed for both type of emulsion (E91 and E92). Those results indicate that the methacrylate modified dextran of the present invention (DXT-poly-MA; D7) both crosslinked or not at the interface of the droplets act as an enzyme-responsive emulsifier. More interestingly, a clear difference in the kinetics of destabilization can be observed depending on the cross-linking of the stabilizer. It appears that the demulsification, hence the release of the encapsulated phase, is much faster for the interface non-crosslinked emulsion with full demulsification observed after 16 hrs. On the other hand, more than half of the interface cross-linked emulsion stabilized with DXT-poly-MA remained stable after 16 hrs. This difference is caused by the enhanced stability conferred by the interface cross-linking step.

Conclusion

Due to the presence of ester bonds induced during the introduction of the methacrylate groups in the DXT polymer, the stability of the emulsion would be triggered in the presence of enzymes specifically adapted to hydrolyse ester bonds.

However, the above-disclosed results show that only the emulsions containing the methacrylate modified DXT polymers or nanoparticles of the present invention (being or not crosslinked) are susceptible to be hydrolysed by some esterase. It is advantageous because they can be useful as targeting delivery system. Thus, the active ingredient included in the O/W emulsion of the present invention is delivery to the target site without being degraded and only in the target site, the emulsion is hydrolysed by the corresponding esterase enzymes delivering the active ingredient in its active form.

Furthermore, these results also demonstrate that the release kinetic of an active ingredient from the emulsions of the present invention can be adjusted. It is advantageous because the destabilisation of the emulsion by enzyme responsiveness can be adjust/modify/adapt to the requirements of each specific case (i.e. disease, patients, active ingredient, amount and posology).

Example 10. Synthesis of Acrylate-Based Hyaluronic Acid Polymer Having DS=36-70% (HA-Poly-A)

HA (100 mg, 2280 kDa) was dissolved in 20 mL of distilled water at pH=8-9 and low temperature using an ice bath. Then, a previously prepared solution of acryloyl chloride (643 μL, 30 eq.) in 20 mL of dichloromethane was added dropwise to HA solution during 1 hour. Reaction pH was maintained at pH=8-9 by adding NaOH 1M during the whole process. After addition, reaction was cooling down for 1 h in an ice bath. The modified hyaluronic acid solution was purified by dialysis against distilled water (MWCO 3,500 Da) at room temperature until reaching deionized water conductivity values<1 μS (9 days, refreshing with 4 L of deionized water twice per day) to obtain HA2.

The modified hyaluronic acid HA1 were prepared following the above-mentioned process using as a starting material HA 50 kDa.

TABLE 8

Summary of the hyaluronic modified of the present invention and the comparative unmodified hyaluronic acid falling outside the scope of the present invention

| Name | Hyaluronic acid MW (Da) | DS (%) * |
|---|---|---|
| HA1 | 50,000 | 36 |
| HA2 | 2.280.000 | 70 |

TABLE 8-continued

Summary of the hyaluronic modified of the present invention and the comparative unmodified hyaluronic acid falling outside the scope of the present invention

| Name | Hyaluronic acid MW (Da) | DS (%) * |
|---|---|---|
| Comp. HA3** | 50.000 | 0 |
| Comp. HA4** | 2.280.000 | 0 |

* DS variability for early reaction times 10 < hours < 30 is ±5%
**Comp HA3 and Comp HA4 are commercially available

Example 11. General Procedure for the Preparation of Single-Chain Methacrylate or Acrylate-Modified Hyaluronic Acid Nanoparticle (HA-SCNP-A or HA-SCNP-MA)

Single-chain methacrylate or acrylate-modified hyaluronic acid nanoparticles were prepared following the process as defined above for the single-chain methacrylate or acrylate-modified dextran nanoparticles using the methacrylate or acrylate modified hyaluronic acid polysaccharide instead of methacrylate or acrylate modified dextran polysaccharide.

Example 12. Synthesis of O/W Emulsions of Acrylate-Based Hyaluronic Acid Polymer and Single-Chain Nanoparticles Method M1: HA-A (z mg, Z % wt. based on the oil phase) was dissolved in deionized water (x g, X % wt., aqueous phase) in an 8 mL glass vial, to this solution an oil (y g, Y % wt., oil phase: triglyceride or small organic molecule), were added raising 2 g of total mass. Then, emulsion was formed using an UP400S (Hielscher) system at 100% of amplitude and pulse during 4 minutes (400 W) with a H3 sonotrode tip (3 mm diameter, 100 mm length). Sonication step was carried out at 0° C., using an ice bath, and without stirring. Following this procedure A the emulsions thus obtained were disclosed in Table 2.

Method M2: HA-A (20 mg, 5% wt. based on the oil phase) was dissolved in 3.6 mL of deionized water (aqueous phase, 90% wt.) in an 8 mL glass vial, to this solution 0.4 g of triglyceride based oil (oil phase, 10% wt.) were added. Then, emulsion was formed using an UP400S (Hielscher) system at 100% of amplitude and pulse during 4 minutes (400 W) with a H3 sonotrode tip (3 mm diameter, 100 mm length). Sonication step was realized at 0° C., using an ice bath, and under magnetic stirring. Following this procedure B the emulsions thus obtained were disclosed in Table 2.

TABLE 9

Experimental conditions for emulsion formation and their characterization following the methods M1 and M2.

| | | Oil phase(x, X) | | Water (y, Y) | | Stabilizer (z, Z) | | | |
|---|---|---|---|---|---|---|---|---|---|
| Name | Class | % wt. | mass (g) | % wt. | mass (g) | Type | % wt.* | mass (mg) | Method |
| E93 | Fish | 10 | 0.4 | 90 | 3.6 | HA1 | 5 | 20 | M2 |
| E94 | Fish | 10 | 0.4 | 90 | 3.6 | HA2 | 5 | 20 | M2 |

Weight percentages (% wt.) are based on the whole emulsion except in the case of the stabilizer,
*% wt. based on the oil phase.
Size distribution values in Intensity (DLS: Dynamic Light Scattering) and Volume (LD: Laser Diffraction).
"N/A": data not available.

As comparative assay, the process for the preparation of O/W emulsions as defined above were performed using unmodified Hyaluronic acids (comp. HA3 and HA4) instead of acrylate modified hyaluronic acid of the present invention. However, emulsions were not formed. Therefore, it is demonstrated that the unmodified hyaluronic acid (HA) did not show any interfacial activity as a clear phase separation.

Example 13. Synthesis of Interfacial Crosslinked O/W Emulsions of Acrylate-Based Hyaluronic Acid Polymer and Single-Chain Nanoparticles Crosslinked emulsion of HA1 with 0.5 thiol (—SH) equivalents is described as example. HA1 (20 mg, 5% wt. related to oil phase) was dissolved in 3.6 mL of deionized water (aqueous phase, 90% wt.) in an 8 mL glass vial, to this solution 0.4 g of fish oil (oil phase, 10% wt.) were added. Then, 1.6 µL DODT (0.5 SH eq.) was carefully added over the oil phase and the volume of NaOH (1M) up to pH=9 (needful for thio-michael addition) was added inside the aqueous phase, and quickly moved on to the sonication step, avoiding basic hydrolysis of the ester groups presented in HA1. Emulsion production is performed using a UP400S (Hielscher) system at 100% of amplitude and pulse during 4 minutes (400 W) with a H3 sonotrode tip (3 mm diameter, 100 mm length). Sonication step was realized at 0° C., using an ice bath, and under magnetic stirring.

Successful cross-linking was assessed by a DMSO/Dioxane (70:30, v/v) challenge, whereby 1.5 mL of crosslinked emulsion was diluted in 30 mL (Dil. 1:20) of the previous DMSO/dioxane solution (which is a solvent for both the water and oil phases). As example, emulsion with 0.5 thiol equivalents was dissolved overnight, at room temperature and under magnetic stirring. Then, oil phase was removed after liquid-liquid extraction with hexane (3×80 mL). Aqueous phase (DMSO, water and HA1-CL) was collected and purified by Dialysis against distilled water (MWCO 3,500 Da) during 4 days, refreshing with 4 L of deionized water twice per day). The resulting aqueous solution was freeze-dried to obtain the crosslinked polymer (HA1-CL) as a white solid. Oil traces were removed via solid-liquid extraction with hexane. HA1-CL was immersed in 1 mL of hexane and triturated using a vortex. After 3 centrifugation cycles (14000 rpm, 5 min, Minispin), whereby solid dextran was centrifuged and the supernatant was removed, the resulting HA1-CL polymer was obtained.

Example 14. Stability Test of O/W Emulsions of Acrylate Modified Hyaluronic Acid of the Present Invention As it is mentioned above, for the purpose of the present invention, an emulsion is considered stable when phase separation is not observed within one month even if increase in droplet diameter is observed.

By Visual Inspection

The emulsions E93 and E94 of the present invention as disclosed above, were prepared and kept resting for 25 days at room temperature. Digital pictures of the oil-in-water emulsions at the beginning and after 25 days were made. As control experiments, pictures of respective unmodified hyaluronic acid (Comp. HA 3 and Comp. HA 4) at the beginning and after 25 days were made.

As judged by visual inspection, the pictures showed that the above disclosed emulsions (E93 and E94) are stables, at least after 25 days stored in the dark at 4° C., because despite a slight increase in droplet as it is shown in Table 10, no phase separation could be observed during this period. it is demonstrated that the acrylate modified hyaluronic acid of the present invention has stabilization capability of emulsions and then are useful as oil-in-water emulsifier, such as for example fish oil droplets in water. However, the unmodified HA did not have any interfacial activity as a clear phase separation.

TABLE 10

Long-term Stability of E93 by Laser Diffraction (LD).

| Time | Volume-Average (d · μm) | Uniformity | Dv10 | Dv50 | Dv90 |
|---|---|---|---|---|---|
| 1 h | 23.9 | 3.2 | 0.93 | 6.43 | 95.5 |
| 2 weeks | 16.2 | 0.89 | 2.01 | 11.2 | 30.5 |
| 2 months | 63.3 | 0.77 | 6.3 | 50.1 | 133 |

Example 15. Enzyme-Responsiveness Analysis of Acrylate Hyaluronic Acid Based Polymers The emulsion E93 (containing the HA-poly-A HA1 and fish oil) of the present invention was put in the presence of the following lipase enzymes that cleave ester bonds:
  *Candida Antarctica* Lipase B (CALB)
  Pancreatic lipase (LP)
By Visual Inspection
  Fractions of 100 μL of the emulsion E93 of the present invention were mixed with 100 μL of each one of the above-mentioned lipases (CALB and LP; 20 mg/mL) in an HPLC glass vials. Mixtures were kept resting for 40 hrs at room temperature before digital pictures acquisition.
  As control experiments, the emulsion E93 was also monitored without the presence of enzymes during 40 hrs. After that time, it was observed a creaming effect due to the relatively large droplet size of the emulsion, but the droplet size remained constant. The emulsion proved to be stable in the absence of enzyme as phase separation or the presence of oil droplets could not be observed on the top of the aqueous phase.
  As judged by visual inspection, the addition of CALB or LP enzymes affected the stability of the emulsion with the appearance of an oil layer at the surface of the emulsion.
  Therefore, these results demonstrated that the enzyme responsiveness of acrylate modified hyaluronic acid of the present invention is comparable with the enzyme responsiveness observed by the methacrylate modified dextran polymers and nanoparticles of the present invention. Then, as it is mentioned above for the methacrylate modified dextran, it is advantageous because the methacrylate or acrylate modified hyaluronic acid of the present invention can be also useful as targeting delivery system. Thus, an active ingredient dissolved in the oil phase of these emulsion can be delivered to the target site without being degraded and only be released in the target site. Particularly, the O/W emulsions comprising the methacrylate or acrylate modified hyaluronic acid of the present invention are hydrolysed by the corresponding esterase enzymes delivering the active ingredient in its active form. Furthermore, the release kinetic of an active ingredient from these emulsions can be also adjusted. Finally, the possibility of cross-linking at the interface of the O/W emulsion allows enhancing the droplet size to be maintained while the release kinetic can also be adjusted, as it is demonstrated by the methacrylate dextran polymers and single-chain nanoparticles.

Example 16. Synthesis of Methacrylate-Based Chitosan Polymer DS=13-30% (CHI-poly-MA)

Chitosan (CHI, 1.5 g) was dissolved in 100 mL of dimethyl sulfoxide (DMSO) under a nitrogen atmosphere, to this solution 1.2 g of p-toluenesulfonic acid (PTSA) and 500 mg of 4-(N,N-dimethylamino)pyridine (DMAP, 1.6 mmol) were added. This mixture was stirred at 50° C. for 2 h. Then, 7 mL of glycidyl methacrylate (GMA, 8.4 mmol) were added and the mixture was stirred at 35° C. for 4 days. The reaction was stopped by adding an equimolar amount of concentrated PTSA (0.98 g, 50 mL water solution) to neutralize DMAP. The modified chitosan solution was purified by dialysis against distilled water (MWCO 3,500 Da) at room temperature until reaching deionized water conductivity values<1 μS (9 days, refreshing with 4 L of deionized water twice per day) to finally obtain CHI2.
  The modified hyaluronic acid CHI1 were prepared following the above-mentioned process but adding the GMA and stirring the resulting mixture at 35° C. for 2 days.

TABLE 11

Summary of the chitosan modified of the present invention and the comparative unmodified chitosan falling outside the scope of the present invention

| Name | DS (%) * |
|---|---|
| CHI1 | 13 |
| CHI2 | 30 |
| Comp. CHI3** | 0 |

* DS variability is ±15%
**Comp CHI3 is commercially available

Example 17. General Procedure for the Preparation of Single-Chain Methacrylate or Acrylate-Modified Chitosan Nanoparticle (CHI-SCNP-MA or CHI-SCNP-A)

Single-chain methacrylate or acrylate-modified chitosan nanoparticles were prepared following the process as defined above for the single-chain methacrylate or acrylate-modified dextran nanoparticles using the methacrylate or acrylate modified chitosan polysaccharide instead of methacrylate or acrylate modified dextran polysaccharide.

Example 18. Synthesis of O/W Emulsions of Methacrylate-Based Chitosan Polymer The O/W emulsions of methacrylate-based chitosan were prepared following the process M2 as defined above for the O/W emulsions of methacrylate-based hyaluronic acid using the methacrylate modified chitosan instead of methacrylate modified hyaluronic acid.
  As comparative assay, the process M2 for the preparation of O/W emulsions as defined above were performed using unmodified chitosan (comp. CHI3) instead of methacrylate modified chitosan of the present invention. However, emulsions were not formed. Therefore, it is demonstrated that the unmodified chitosan did not show any interfacial activity as a clear phase separation.

TABLE 12

Experimental conditions for emulsion formation and their characterization.

| Name | Oil phase(x, X) | | | Water (y, Y) | | Stabilizer (z, Z) | | | |
|---|---|---|---|---|---|---|---|---|---|
| | Class | % wt. | mass (g) | % wt. | mass (g) | Type | % wt.* | mass (mg) | Method |
| Comp. E95 | Fish | 10 | 0.4 | 90 | 3.6 | Comp. CHI3 | 5 | 20 | M2 |
| E96 | Fish | 10 | 0.4 | 90 | 3.6 | CHI1 | 5 | 20 | M2 |
| E97 | Fish | 10 | 0.4 | 90 | 3.6 | CHI2 | 5 | 20 | M2 |

Weight percentages (% wt.) are based on the whole emulsion except in the case of the stabilizer,
*% wt. based on the oil phase.
Size distribution values in Intensity (DLS: Dynamic Light Scattering) and Volume (LD: Laser Diffraction).
"N/A": data not available.

Example 19. Stability Test of O/W Emulsions of Methacrylate Modified Chitosan of the Present Invention As it is mentioned above, for the purpose of the present invention, an emulsion is considered stable when phase separation is not observed within one month even if increase in droplet diameter is observed.

By Visual Inspection

The emulsions E96 and E97 of the present invention as disclosed above, were prepared and kept resting for 10 days at room temperature. Digital pictures of the oil-in-water emulsions at the beginning and after 10 days were made. As control experiments, pictures of respective unmodified chitosan (Comp.CHI3) at the beginning and after 10 days were made.

As judged by visual inspection, the pictures showed that the above disclosed emulsions (E96 and E97) are stables, at least after 10 days stored in the dark at 4° C., because despite a slight increase in droplet as it is shown in Tables 13 and 14, no phase separation could be observed during this period. it is demonstrated that the methacrylate modified chitosan of the present invention has stabilization capability of emulsions and then are useful as oil-in-water emulsifier, such as for example fish oil droplets in water. However, the unmodified CHI did not have any interfacial activity as a clear phase separation.

TABLE 13

Long-term Stability of E96 by Laser Diffraction (LD).

| Time | Volume-Average (d · μm) | Uniformity | Dv10 | Dv50 | Dv90 |
|---|---|---|---|---|---|
| 1 h | 7.59 | 4.01 | 0.59 | 1.62 | 12 |
| 10 days | 3.48 | 2.65 | 0.46 | 1.06 | 2.24 |

TABLE 14

Long-term Stability of E97 by Laser Diffraction (LD).

| Time | Volume-Average (d · μm) | Uniformity | Dv10 | Dv50 | Dv90 |
|---|---|---|---|---|---|
| 1 h | 1.41 | 0.490 | 0.49 | 1.28 | 2.55 |
| 10 days | 186 | 0.79 | 0.58 | 195 | 495 |

Example 20. General Procedure for the Preparation of Acrylate or Methacrylate-Based Chitosan Single-Chain Nanoparticles Emulsions based on methacrylate or acrylate based chitosan single-chain nanoparticles were prepared following the process as defined above for the methacrylate or acrylate based dextran single-chain nanoparticles using the methacrylate or acrylate modified chitosan instead of methacrylate or acrylate modified dextran polysaccharide.

Example 21. General Procedure for the Synthesis of Interfacial Crosslinked O/W Emulsions of Methacrylate or Acrylate-Based Chitosan Polymer and Single-Chain Nanoparticles Interfacial crosslinked O/W emulsions based on methacrylate or acrylate based chitosan polymer and single-chain nanoparticles were prepared following the process as defined above for the methacrylate or acrylate based dextran polymer and single-chain nanoparticles using the methacrylate or acrylate modified chitosan polymer or single-chain.

Therefore, these results demonstrated that the methacrylate or acrylate modified chitosan polymer and single-chain nanoparticles of the present invention are comparable with the results obtained with the methacrylate or acrylate hyaluronic acid or dextran polymers and single-chain nanoparticles of the present invention. Then, as it is mentioned above for the methacrylate modified dextran, it is advantageous because the methacrylate or acrylate modified hyaluronic acid of the present invention can be also useful as oil-in-water emulsion stabilizer and also as targeting delivery system.

Example 22. Reproduction of the Comparative N-Acrylchitosan (NAC) Prepolymer Disclosed in Xiantao Shen et al. (Cf. "Bacterial Imprinting at Pickering Emulsion Interfaces". Angewandte Chemie, International Edition. 2014, Vol. 53, No. 11, Pages 10687-10690)

Preparation Process of Comparative N-Acrylchitosan (NAC) Prepolymer

The process for the preparation of the N-acrylchitosan (NAC) prepolymer disclosed in Xiantao Shen et al. is disclosed herein below which corresponds to the FIG. S1 of the supplement information of Xiantao Shen et al.

Two separate solutions were first prepared: A) (solution A) 1.61 g of chitosan was dispersed in a mixture of N,N-Dimethylacetamide (DMAC) (40 mL) and triethylamine (2 mL). B) (solution B) 161 μL of acryloyl chloride was added into 5 mL of DMAC. Solution A was deoxygenated by nitrogen bubbling for 10 min at 0° C. Solution B was then added dropwise into solution A. The mixture was then stirred at 0° C. for 4 h followed by stirring at 25° C. for 20 h. After successive washes in DMAC and methanol, the comparative N-acrylchitosan (NAC) powder was recovered by filtration and purified by dialysis against ultrapure water (MWCO 3,500 Da) at room temperature for 2 days. Finally, dialyzed compound was dried in a vacuum chamber.

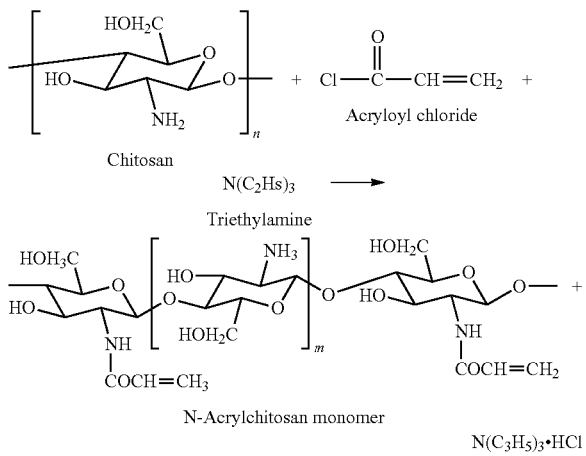

FIG. S1. Synthesis of the comparative N-acrylchitosan pre-polymer. The molar ratio between the amino groups in chitosan and acryloyl chloride was 5:1.

Determination of the Surface Tension (ST)

The measurement of the surface tension of the comparative N-acrylchitosan pre-polymer disclosed in Xiantao Shen et al. was performed by the Du Noüy Ring method defined in the present application (cf. characterization methods of the experimental section).

The obtained value of the surface tension for the comparative N-acrylchitosan pre-polymer disclosed in Xiantao Shen et al., was 64.85±0.1 mN/m (at pH), being outside the claimed range (equal to or lower than 63 mN/m).

Conclusion

As it is shown in the experimental section, only the polysaccharides or nanoparticles of the present invention which have the claimed surface tension have interfacial activity and also esterase enzyme responsive.

In fact, as it is already disclosed by Xiantao Shen et al., the comparative N-acrylchitosan pre-polymer having a surface tension (about 64.9 mN/m) higher than the claimed range (equal to or lower than 63 mN/m) does not show any interfacial activity as phase separation stabilizer. Xiantao Shen et al. already mentioned that only the bacteria-pre-polymer complex (cf. scheme 1 of Xiantao Shen et al.) obtained by the assembly of the positively charged comparative N-acrylchitosan pre-polymer with the negatively charged bacteria has particle stabilizer properties (cf. last paragraph of page 10687).

In particular, Xiantao Shen et al. discloses that no stable emulsion was obtained when the bacteria or the comparative N-acrylchitosan pre-polymer were used separately without being forming part of a complex (cf. second paragraph of page 10688). Thus, it is concluded that the assembly of the bacteria with the chitosan is required for achieving the emulsion stabilizer effect.

CITATION LIST

1. Qin et al., Polym. Chem. 2014, vol. 5, pp. 6523-6533.
2. Rudolph Macy, J. Chem. Educ. 1935, vol. 12(12), pp. 573.
3. van Dijk-Wolthuis et al., Biomolecular Engineering, 2007, vol. 24, pp. 496-504.
4. L. Ferreira et al., Biomaterials, 2002, vol. 23, pp. 3957-3967.
5. Academic press Dictionary of Science and Technology, 1992, pp. 531.
6. A terminological Dictionary of the Pharmaceutical Sciences. 2007, pp. 190.
7. Xiantao Shen et al. "Bacterial imprinting at Pickering emulsion interfaces". Angewandte Chemie, International Edition. 2014, vol. 53, no. 11, pages 10687-10690.
8. J. Drelich et al. "Measurement of interfacial tension in fluid-fluid systems", Encyclopedia of Surface and colloid Science, 2002, page 3152-3166).

For reasons of completeness, various aspects of the invention are set out in the following numbered clauses:

Clause 1. Use of a methacrylate or acrylate modified polysaccharide; or alternatively, a single-chain polysaccharide methacrylate or acrylate-based nanoparticle, having a surface tension measured by Du Noüy Ring method equal to or lower than 63 mN/m, as oil-in-water emulsion stabilizer.

Clause 2. The use according to clause 1, wherein the polysaccharide is selected from dextran, hyaluronic acid, alginate, gellan gum, cellulose and derivative thereof, glycogen, and chitosan.

Clause 3. The use according to any of the clauses 1 or 2, wherein:
the degree of substitution of the polysaccharide with the methacrylate or acrylate groups is from 1 to 100% of modified repeating units of the polysaccharide; or alternatively,
the degree of substitution of the nanoparticles with methacrylate or acrylate groups is from 1% to 98% of modified repeating units of the nanoparticles.

Clause 4. The use according to any of the clauses 1-3, wherein the carbon atom of the group —CO— of the methacrylate or acrylate moiety is covalently bond to the oxygen atom of the OH— moiety of the polysaccharide.

Clause 5. The use according to any of the clauses 1-4, wherein the methacrylate or acrylate modified polysaccharide is selected from the group consisting of a methacrylate modified dextran having a degree of substitution of the methacrylate groups from 1% to 100% of modified repeating units of the dextran and comprising repeating units of formula (I)

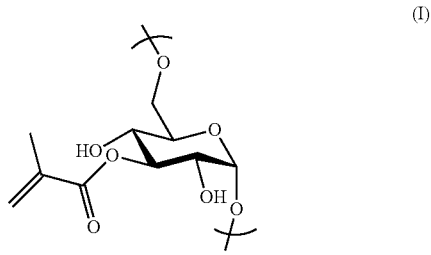

and an acrylate modified dextran having a degree of substitution of the acrylate groups from 1% to 100% of modified repeating units of the dextran and comprising repeating units of formula (II);

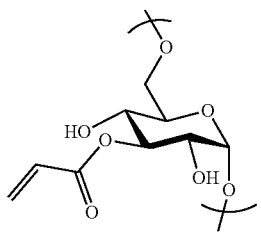
(II)

Clause 6. The use according to any of the clauses 1-4, wherein the a single-chain polysaccharide methacrylate or acrylate-based nanoparticle is a single-chain dextran methacrylate or acrylate-based nanoparticle having:
  a degree of substitution of the dextran with methacrylate or acrylate groups from 1% to 98% of modified repeating units of the nanoparticles; and
  a percentage of intra-molecular crosslinking from 1 to 60 molar % of the total amount of monomer units present in the dextran methacrylate or acrylate chain.

Clause 7. The use according to any of the clauses 1-4, wherein the methacrylate or acrylate modified polysaccharide is selected from the group consisting of a methacrylate modified hyaluronic acid having a degree of substitution of the methacrylate groups from 1% to 100% of modified repeating units of the hyaluronic acid and comprising repeating units of formula (IV)

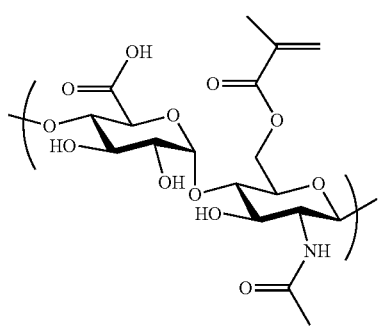
(IV)

and an acrylate modified hyaluronic acid having a degree of substitution of the acrylate groups from 1% to 100% of modified repeating units of the hyaluronic acid and comprising repeating units of formula (V)

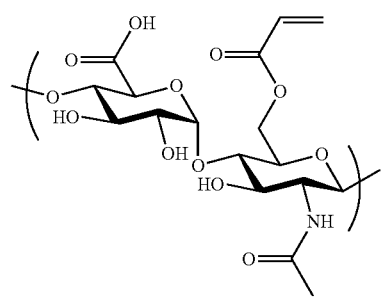
(V)

or alternatively, wherein the a single-chain polysaccharide methacrylate or acrylate-based nanoparticle is a single-chain hyaluronic acid methacrylate or acrylate-based nanoparticle having:
  a degree of substitution of the hyaluronic acid with methacrylate or acrylate groups from 1% to 98% of modified repeating units of the nanoparticles; and
  a percentage of intra-molecular crosslinking from 1 to 60 molar % of the total amount of monomer units present in the hyaluronic acid methacrylate or acrylate chain.

Clause 8. The use of according to any of the clauses 1-4, wherein the methacrylate or acrylate modified polysaccharide is selected from the group consisting of a methacrylate modified chitosan having a degree of substitution of the methacrylate groups from 1% to 100% of the repeating units of chitosan and comprising repeating units of formula (VII)

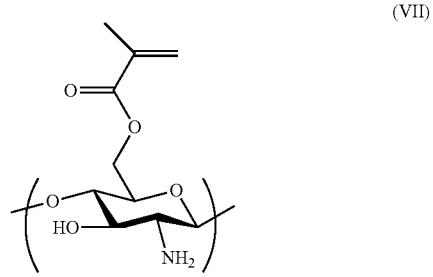
(VII)

and an acrylate modified chitosan having a degree of substitution of the chitosan with acrylate groups from 1% to 100% of the repeating units of chitosan and comprising repeating units of formula (VIII)

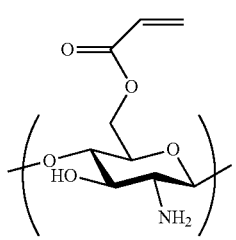
(VIII)

or alternatively, wherein the a single-chain polysaccharide methacrylate or acrylate-based nanoparticle is a single-chain chitosan methacrylate or acrylate-based nanoparticle having:
a degree of substitution of the chitosan with methacrylate or acrylate groups from 1% to 98% of modified repeating units of the nanoparticles; and
a percentage of intra-molecular crosslinking from 1 to 60 molar % of the total amount of monomer units present in the chitosan methacrylate or acrylate chain.

Clause 9. An oil-in-water emulsion stabilizer composition comprising:
  a methacrylate or acrylate modified polysaccharide as defined in any of the clauses 1-8; or alternatively, a single-chain polysaccharide methacrylate or acrylate-based nanoparticle as defined in any of the clauses 1-8; and
  one or more appropriate excipients or carriers.

Clause 10. An oil-in-water emulsion comprising:
  (a) the external water phase (W) comprising:
    (a1) a solvent selected from the group consisting water, glycol and a mixture thereof; and
    (a2) optionally, one or more hydrophilic compounds selected from the group consisting of: (a2') hydrophilic active agent and (a2") hydrophilic excipients or carriers;

(b) the internal oily phase (O) comprising one or more lipophilic compounds selected from the group consisting of:
  (b1) lipophilic active agents, and
  (b2) lipophilic excipients or carriers;
and
(c) an interfacial layer (IL) between the external water phase (W) and the internal oily phase (O) comprising:
  (c1) one or more emulsion stabilizer selected from the group consisting of:
    (c1') methacrylate or acrylate modified polysaccharides as defined in any of the clauses 1-8;
    (c1") single-chain polysaccharide methacrylate or acrylate-based nanoparticles as defined in any of the clauses 1-8;
    (c1''') interfacial crosslinked methacrylate or acrylate modified polysaccharides obtainable by reacting the methacrylate or acrylate modified polysaccharides as defined in any of the clauses 1-8 with an interfacial crosslinking agent, wherein the interfacial crosslinked methacrylate or acrylate modified polysaccharides has an interfacial crosslinking degree from 25 to 100% of the methacrylate or acrylate groups of the polysaccharide; or alternatively,
    (c1'''') interfacial crosslinked single-chain polysaccharide methacrylate or acrylate based nanoparticles obtainable by reacting the single-chain polysaccharide methacrylate or acrylate-based nanoparticles as defined in any of the clauses 1-8 with an interfacial crosslinking agent, wherein the interfacial crosslinked single-chain polysaccharide methacrylate or acrylate based nanoparticles has an interfacial crosslinking degree from 25 to 100% of the methacrylate or acrylate groups of the nanoparticles; and
  c2) optionally, one or more hydrophilic active agents.

Clause 11. The oil-in-water emulsion according to clause 10, wherein the active agent is selected from the group consisting of a pharmaceutical active ingredient, a diagnostic agent and a cosmetic agent.

Clause 12. Use of an oil-in-water emulsion according to any of the clauses 10 or 11, wherein the emulsion is absent of active agents, as a carrier.

Clause 13. An oil-in-water emulsion according to any of the clauses 10 or 11, wherein the emulsion is a pharmaceutical emulsion comprising one or more pharmaceutical active ingredient as active agent, for use in therapy.

Clause 14. The use of an oil-in-water according to any of the clauses 10 or 11, wherein the emulsion is a cosmetic emulsion comprising one or more cosmetic agent, as a skin or hair care agent.

Clause 15. An oil-in-water emulsion according to any of the clauses 10 or 11, wherein the emulsion is a diagnostic emulsion comprising one or more diagnostic agent, for use in diagnosis.

The invention claimed is:
1. An oil-in-water emulsion comprising:
  (a) an external water phase (W) comprising:
    (a1) a solvent selected from the group consisting of water, glycol, and a mixture thereof; and
    (a2) optionally, one or more hydrophilic compounds selected from the group consisting of: (a2') hydrophilic active agent and (a2") hydrophilic excipients or carriers;
  (b) the internal oily phase (O) comprising one or more lipophilic compounds selected from the group consisting of:
    (b1) lipophilic active agents, and
    (b2) lipophilic excipients or carriers;
  and
  (c) an interfacial layer (IL) between the external water phase (W) and the internal oily phase (O) comprising:
    (c1) one or more emulsion stabilizer selected from the group consisting of:
      (c1') methacrylate or acrylate modified polysaccharides having a surface tension measured by Du Noüy Ring method equal to or lower than 63 mN/m;
      (c1") single-chain polysaccharide methacrylate or acrylate-based nanoparticles having a surface tension measured by Du Noüy Ring method equal to or lower than 63 mN/m;
      (c1''') interfacial crosslinked methacrylate or acrylate modified polysaccharides obtainable by reacting the methacrylate or acrylate modified polysaccharides as defined in (c1') with an interfacial crosslinking agent, wherein the interfacial crosslinked methacrylate or acrylate modified polysaccharides has an interfacial crosslinking degree from 25 to 100% of the methacrylate or acrylate groups of the polysaccharide; or alternatively,
      (c1'''') interfacial crosslinked single-chain polysaccharide methacrylate or acrylate based nanoparticles obtainable by reacting the single-chain polysaccharide methacrylate or acrylate-based nanoparticles as defined in (c1") with an interfacial crosslinking agent, wherein the interfacial crosslinked single-chain polysaccharide methacrylate or acrylate based nanoparticles has an interfacial crosslinking degree from 25 to 100% of the methacrylate or acrylate groups of the nanoparticles;
    wherein the carbon atom of the group —CO— of the methacrylate or acrylate moiety is covalently bonded to the oxygen atom of the OH— moiety of the polysaccharide; and
    c2) optionally, one or more hydrophilic active agents.

2. The oil-in-water emulsion according to claim 1, wherein the active agent is selected from the group consisting of a pharmaceutical active ingredient, a diagnostic agent and a cosmetic agent.

3. The oil-in-water emulsion according to claim 1, wherein the emulsion is absent of active agents, as a carrier.

4. A method of therapy, the method comprising:
  using an oil-in-water emulsion according to claim 1, wherein the emulsion is a pharmaceutical emulsion comprising one or more pharmaceutical active ingredients as the active agent.

5. The method according to claim 4, wherein the emulsion is a pharmaceutical emulsion comprising one or more pharmaceutical active ingredients as the active agent selected from the group consisting of: vasoactive agents; neuroactive agents; hormones; growth factors; cytokines; anaesthetics; steroids; anticoagulants, D-Phe-Pro-Arg chloromethyl keton, an RGD peptide-containing compound, a polylysine-containing compound, heparin, antithrombin compounds, platelet receptor antagonists, anti-thrombin, anti-platelet receptor antibodies, aspirin, prostaglandin inhibitors, platelet inhibitors, and ticlc antiplatelet peptides; anti-inflammatories, steroids, dexamethasone, prednisolone, triamcinolone, fluorometholone, betamethasone, budesonide, hydrocortisone, clobetasone, beclometasone, desoximetasone, methylprednisolone, non-steroid agents (AINE), dicoflenac, aceclofenac, benzydamine, dexketoprofen, etofenamate, fepradinol, ibuprofen, indomethacin, ketoprofen, and piroxicam; immunomodulating agents; cytotoxic agents; prophylactic agents; antivirals; antigens; antibodies; anti-thrombogenic agents, heparin, heparin derivatives, urokinase, and PPack (dextrophenylalanine proline arginine chloromethylketone); anti-proliferative agents, enoxaprin, angiopeptin, monoclonal antibodies capable of blocking smooth muscle cell proliferation, hirudin, and acetylsalicylic acid); antineoplastic/antiproliferative/anti-miotic agents, paclitaxel, 5-fluorouracil, cisplatin, vinblastine, vincristine, epothilones, endostatin, angiostatin, and thymidine kinase inhibitors; anaesthetic agents, lidocaine, bupivacaine, and ropivacaine; vascular cell growth promoters, growth factor inhibitors, growth factor receptor antagonists, transcriptional activators, and translational promoters; vascular cell growth inhibitors, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms; radiopharmaceutical; analgesic drugs; anorectic agents; anti-anaemia agents; anti-asthma agents; anti-diabetic agents; antihistamine, diphenydramine, dimetindene, and promethazine; antimuscarinic drugs; cardiovascular drugs; central nervous system stimulator; central nervous system depressant; anti-depressant; anti-epileptic; anxiolytic agents; hypnotic agents; sedative; beta blocker; homeostatic agents; hormone; vasodilator; vasoconstrictor; vitamin; chemotherapeutics including antivirals, acyclovir, penciclovir, valaciclovir, idoxuridine, tromantadine, imiquimod, and metronidazole; antibiotics, fusidic acid, mupirocin, gentamicin, neomycin, retapamulin, clindamycin, erythromycin, and chlortetracycline; antifungals, imidazole and triazole derivatives, bifonazole, chlotrimazole, eberconazole, econazole, fenticonazole, flutrimazole, ketoconazole, miconazole, oxiconazole, sertaconazole, thioconazole; nistatin, Naftifine, terbinafine, tolnaftate, and ciclopirox; healing agents, *Arnica montana, Centella asiatica*, and becaplermin; local anesthetics, lidocaine, benzocaine, and tetracaine; anti-psoriatic agents, etanercept, adalimumab, ustekinumab, dithranol, calcipotriol, calcitriol, tacalcitol, and tazarotene; retinoid agents, tretinoin, isotretinoin, and adapalene; antiseptic and desinfectant agents, chlorhexidine, boric acid, and triclosan; tacrolimus; hydroquinone; minoxidil; Finasteride; Gastrointestinal; Antitussive agents; Expectorants; anti-spasmodics; diuretics; antihemorrhoidals; hypnotics, psychotropic; decongestants; laxant; and antiacid.

6. The oil-in-water emulsion according to claim 1, wherein the emulsion is a cosmetic emulsion comprising one or more cosmetic agent, as a skin or hair care agent.

7. The oil-in-water emulsion according to claim 1, wherein the emulsion is a diagnostic emulsion comprising one or more diagnostic agent, for use in diagnosis.

8. The oil-in-water emulsion according to claim 7, wherein the diagnostic agent is a diagnostically imaging acceptable agent selected from the group consisting of fluorescent agent, contrast agent, and radioimaging agent.

9. The oil-in-water emulsion according to claim 1, wherein the diagnostic agent is a diagnostically imaging acceptable selected from the group consisting of diethylene triamine pentaacetic acid (DTPA), 1,4,7,10-tetraazacyclododecane-1,4,7,10-tetraacetic acid (DOTA), 1,4,7-triazacyclononane-1,4,7-triacetic acid (NOTA), fluorescein, rhodamine, and cyane 5,5.

10. The oil in water emulsion according to claim 1, wherein the methacrylate or acrylate modified polysaccharide has a surface tension measured by Du Noüy Ring method equal to or lower than 60 mN/m.

11. The oil in water emulsion according to claim 1, wherein the polysaccharide is selected from dextran, hyaluronic acid, alginate, gellan gum, cellulose and a derivative thereof, glycogen, and chitosan.

12. The oil in water emulsion according to claim 1, wherein the polysaccharide is selected from dextran, hyaluronic acid, and chitosan.

13. The oil in water emulsion according to claim 1, wherein the degree of substitution of the polysaccharide with the methacrylate or acrylate groups is from 1 to 100% of modified repeating units of the polysaccharide.

14. The oil in water emulsion according to claim 1, the degree of substitution of the nanoparticles with methacrylate or acrylate groups is from 1% to 98% of modified repeating units of the nanoparticles.

15. The oil in water emulsion according to claim 1), wherein the methacrylate or acrylate modified polysaccharide is selected from the group consisting of a methacrylate modified dextran having a degree of substitution of the methacrylate groups from 1% to 100% of modified repeating units of the dextran and comprising repeating units of formula (I):

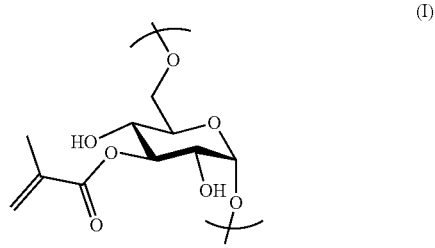

and an acrylate modified dextran having a degree of substitution of the acrylate groups from 1% to 100% of modified repeating units of the dextran and comprising repeating units of formula (II):

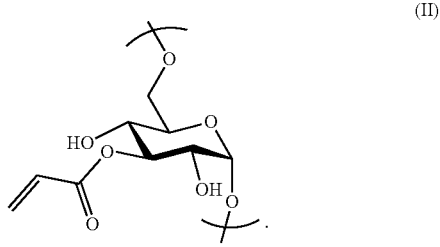

16. The oil in water emulsion according to claim 1, wherein the single-chain polysaccharide methacrylate or acrylate-based nanoparticle is a single-chain dextran methacrylate or acrylate-based nanoparticle having:
  a degree of substitution of the dextran with methacrylate or acrylate groups from 1% to 98% of modified repeating units of the nanoparticles; and a percentage of intra-molecular crosslinking from 1 to 60 molar % of the total amount of monomer units present in the dextran methacrylate or acrylate chain.

17. The oil in water emulsion according to claim 1, wherein the methacrylate or acrylate modified polysaccharide is selected from the group consisting of a methacrylate modified hyaluronic acid having a degree of substitution of the methacrylate groups from 1% to 100% of modified repeating units of the hyaluronic acid and comprising repeating units of formula (IV):

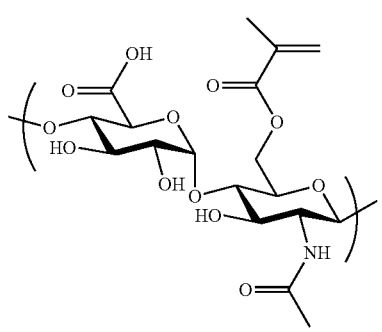

(IV)

and an acrylate modified hyaluronic acid having a degree of substitution of the acrylate groups from 1% to 100% of modified repeating units of the hyaluronic acid and comprising repeating units of formula (V):

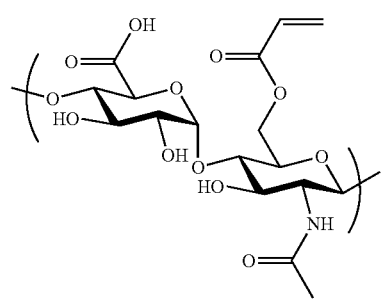

(V)

or alternatively, wherein the single-chain polysaccharide methacrylate or acrylate-based nanoparticle is a single-chain hyaluronic acid methacrylate or acrylate-based nanoparticle having:
a degree of substitution of the hyaluronic acid with methacrylate or acrylate groups from 1% to 98% of modified repeating units of the nanoparticles; and
a percentage of intra-molecular crosslinking from 1 to 60 molar % of the total amount of monomer units present in the hyaluronic acid methacrylate or acrylate chain.

18. The oil in water emulsion according to claim 1, wherein the methacrylate or acrylate modified polysaccharide is selected from the group consisting of a methacrylate modified chitosan having a degree of substitution of the methacrylate groups from 1% to 100% of the repeating units of chitosan and comprising repeating units of formula (VII):

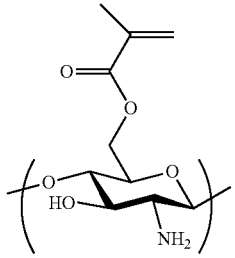

(VII)

and an acrylate modified chitosan having a degree of substitution of the chitosan with acrylate groups from 1% to 100% of the repeating units of chitosan and comprising repeating units of formula (VIII):

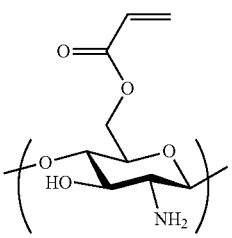

(VIII)

or alternatively, wherein the single-chain polysaccharide methacrylate or acrylate-based nanoparticle is a single-chain chitosan methacrylate or acrylate-based nanoparticle having:
a degree of substitution of the chitosan with methacrylate or acrylate groups from 1% to 98% of modified repeating units of the nanoparticles; and
a percentage of intra-molecular crosslinking from 1 to 60 molar % of the total amount of monomer units present in the chitosan methacrylate or acrylate chain.

* * * * *